(12) United States Patent
Farrell et al.

(10) Patent No.: US 10,905,858 B2
(45) Date of Patent: Feb. 2, 2021

(54) SAFETY NEEDLE SYSTEM OPERABLE WITH A MEDICAL DEVICE

(71) Applicant: Tangent Medical Technologies, Inc., San Clemente, CA (US)

(72) Inventors: Nathan Farrell, Ann Arbor, MI (US); Adrienne Rose Harris, Ann Arbor, MI (US); Steven B. White, Ann Arbor, MI (US); Ronald Dean Duis, Ann Arbor, MI (US); Henry J. H. Brown, Ann Arbor, MI (US)

(73) Assignee: Tangent Medical Technologies, Inc., San Clemente, CA (US)

(*) Notice: Subject to any disclaimer, the term of this patent is extended or adjusted under 35 U.S.C. 154(b) by 0 days.

(21) Appl. No.: 16/219,606

(22) Filed: Dec. 13, 2018

(65) Prior Publication Data
US 2019/0282784 A1    Sep. 19, 2019

Related U.S. Application Data

(63) Continuation of application No. 14/299,872, filed on Jun. 9, 2014, now Pat. No. 10,159,818, which is a
(Continued)

(51) Int. Cl.
*A61M 25/06* (2006.01)
*A61M 5/32* (2006.01)
*A61M 5/162* (2006.01)

(52) U.S. Cl.
CPC ...... *A61M 25/0631* (2013.01); *A61M 5/1626* (2013.01); *A61M 5/3204* (2013.01);
(Continued)

(58) Field of Classification Search
CPC .. A61M 5/326; A61M 5/1626; A61M 5/3204; A61M 5/162; A61M 25/0631;
(Continued)

(56) References Cited

U.S. PATENT DOCUMENTS 2,868,200 A    1/1959    Gewecke
3,561,429 A    2/1971    Jewett
(Continued)

FOREIGN PATENT DOCUMENTS

CN    101466431 A    6/2009
EP    0 576 302    12/1993
(Continued)

OTHER PUBLICATIONS

U.S. Appl. No. 15/427,714, filed Feb. 8, 2017, White et al.
(Continued)

*Primary Examiner* — Nilay J Shah
(74) *Attorney, Agent, or Firm* — Knobbe Martens Olson & Bear, LLP

(57) ABSTRACT

A safety needle system operable with a medical device includes: a housing with a needle mount having a needle; and a sheath telescopically engaged with the housing and surrounding the needle such that the sheath operates in a retracted position, in which the sheath exposes the needle, and an extended position, in which the sheath surrounds the needle. The sheath is coupleable to the medical device such that removal of the needle from the medical device draws the sheath over the needle, transitioning the sheath from the retracted position to the extended position. The system can include a slider engaged with the sheath and/or housing and including a restraint that engages and disengages the sheath to respectively reinforce and weaken the coupling of the sheath and medical device. The sheath can include a longitudinal track that slidingly engages a setting of the housing between sheath positions.

25 Claims, 26 Drawing Sheets

Related U.S. Application Data continuation of application No. 13/111,716, filed on May 19, 2011, now Pat. No. 8,814,833.

(60) Provisional application No. 61/352,220, filed on Jun. 7, 2010, provisional application No. 61/407,777, filed on Oct. 28, 2010, provisional application No. 61/448,132, filed on Mar. 1, 2011, provisional application No. 61/346,292, filed on May 19, 2010, provisional application No. 61/407,797, filed on Oct. 28, 2010, provisional application No. 61/418,354, filed on Nov. 30, 2010, provisional application No. 61/438,781, filed on Feb. 2, 2011, provisional application No. 61/442,456, filed on Feb. 14, 2011.

(52) U.S. Cl.
CPC ......... *A61M 5/326* (2013.01); *A61M 25/0606* (2013.01); *A61M 25/0618* (2013.01); *A61M 25/0693* (2013.01)

(58) Field of Classification Search
CPC .......... A61M 25/0618; A61M 25/0693; A61M 25/0612; A61M 25/0606
See application file for complete search history.

(56) References Cited

U.S. PATENT DOCUMENTS

| | | |
|---|---|---|
| 3,729,031 A | 4/1973 | Baldwin |
| 4,013,080 A | 3/1977 | Froning |
| 4,160,450 A | 7/1979 | Doherty |
| 4,316,461 A | 2/1982 | Marais et al. |
| 4,380,234 A | 4/1983 | Kamen |
| 4,397,641 A | 8/1983 | Jacobs |
| 4,424,833 A | 1/1984 | Spector et al. |
| 4,430,073 A | 2/1984 | Bemis et al. |
| 4,432,752 A | 2/1984 | Marlon |
| 4,435,173 A | 3/1984 | Siposs et al. |
| 4,436,519 A | 3/1984 | O'Neill |
| 4,576,589 A | 3/1986 | Krause et al. |
| 4,591,356 A | 5/1986 | Christie |
| 4,605,011 A | 8/1986 | Näslund |
| 4,681,567 A | 7/1987 | Masters et al. |
| 4,695,274 A | 9/1987 | Fox |
| 4,755,170 A | 7/1988 | Golden |
| 4,776,841 A | 10/1988 | Catalano |
| 4,798,594 A | 1/1989 | Hillstead |
| 4,799,494 A | 1/1989 | Wang |
| 4,801,295 A | 1/1989 | Spencer |
| 4,834,271 A | 5/1989 | Litwin |
| 4,834,718 A | 5/1989 | McDonald |
| 4,846,796 A | 7/1989 | Carrell et al. |
| 4,890,626 A | 1/1990 | Wang |
| 4,898,587 A | 2/1990 | Mera |
| 4,909,798 A | 3/1990 | Fleischhacker et al. |
| 4,935,010 A | 6/1990 | Cox et al. |
| 4,936,830 A | 6/1990 | Verlier |
| 4,941,883 A | 7/1990 | Venturini |
| 4,944,725 A | 7/1990 | McDonald |
| 4,944,728 A | 7/1990 | Carrell et al. |
| 4,952,207 A | 8/1990 | Lemieux |
| 4,964,854 A * | 10/1990 | Luther .............. A61M 5/3273 604/166.01 |
| 4,976,698 A | 12/1990 | Stokley |
| 5,000,740 A | 3/1991 | Ducharme et al. |
| 5,049,136 A | 9/1991 | Johnson |
| 5,084,023 A | 1/1992 | Lemieux |
| 5,084,026 A | 1/1992 | Shapiro |
| 5,085,648 A | 2/1992 | Purdy et al. |
| 5,092,845 A | 3/1992 | Chang |
| 5,098,048 A | 3/1992 | Chen |
| 5,116,324 A | 5/1992 | Brierley et al. |
| 5,129,884 A | 7/1992 | Dysarz |
| 5,135,504 A | 8/1992 | Mclees |
| 5,147,327 A | 9/1992 | Johnson |
| 5,147,333 A | 9/1992 | Raines |
| 5,147,375 A | 9/1992 | Sullivan et al. |
| 5,171,234 A | 12/1992 | Jepson et al. |
| 5,192,275 A | 3/1993 | Burns |
| 5,199,948 A | 4/1993 | McPhee |
| 5,201,717 A | 4/1993 | Wyatt et al. |
| 5,207,647 A | 5/1993 | Phelps |
| 5,211,634 A | 5/1993 | Vaillancourt |
| 5,215,525 A | 6/1993 | Sturman |
| 5,215,528 A | 6/1993 | Purdy et al. |
| 5,215,537 A | 6/1993 | Lynn et al. |
| 5,232,010 A | 8/1993 | Rozenblatt et al. |
| 5,238,010 A | 8/1993 | Grabenkort et al. |
| 5,254,097 A | 10/1993 | Schock et al. |
| 5,269,771 A | 12/1993 | Thomas et al. |
| 5,295,970 A | 3/1994 | Clinton et al. |
| 5,295,977 A | 3/1994 | Cohen et al. |
| 5,300,034 A | 4/1994 | Behnke et al. |
| 5,312,368 A | 5/1994 | Haynes |
| 5,314,411 A | 5/1994 | Bierman et al. |
| 5,351,383 A | 5/1994 | Behnke et al. |
| 5,330,438 A | 7/1994 | Gollobin et al. |
| 5,352,205 A | 10/1994 | Dales et al. |
| 5,354,275 A | 10/1994 | Behnke et al. |
| 5,354,282 A | 10/1994 | Bierman |
| 5,356,390 A | 10/1994 | Erskine |
| 5,360,408 A | 11/1994 | Vaillancourt |
| 5,364,368 A | 11/1994 | Kauffman et al. |
| 5,368,801 A | 11/1994 | Vaillancourt |
| 5,375,589 A | 12/1994 | Bhatta |
| 5,376,071 A | 12/1994 | Henderson |
| 5,376,082 A | 12/1994 | Phelps |
| 5,400,500 A | 3/1995 | Behnke et al. |
| 5,405,331 A | 4/1995 | Behnke et al. |
| 5,413,562 A | 5/1995 | Swauger |
| 5,425,465 A | 6/1995 | Healy |
| 5,425,721 A | 6/1995 | Malenchek |
| 5,439,451 A | 8/1995 | Collinson et al. |
| 5,445,623 A | 8/1995 | Richmond |
| 5,456,668 A | 10/1995 | Ogle, II |
| 5,458,658 A | 10/1995 | Sircom |
| 5,462,255 A | 10/1995 | Rosen et al. |
| 5,472,430 A | 12/1995 | Vaillancourt et al. |
| 5,474,544 A | 12/1995 | Lynn |
| 5,476,452 A | 12/1995 | Thompson |
| 5,487,728 A | 1/1996 | Vaillancourt |
| 5,487,734 A | 1/1996 | Thorne et al. |
| 5,498,247 A | 3/1996 | Brimhall |
| 5,501,674 A | 3/1996 | Trombley, III et al. |
| 5,509,912 A | 4/1996 | Vaillancourt et al. |
| 5,514,111 A | 5/1996 | Phelps |
| 5,514,116 A | 5/1996 | Vaillancourt et al. |
| 5,522,804 A | 6/1996 | Lynn |
| 5,545,146 A | 8/1996 | Ishak |
| 5,549,651 A | 8/1996 | Lynn |
| 5,558,651 A | 9/1996 | Crawford et al. |
| 5,562,631 A | 10/1996 | Bogert |
| 5,575,769 A | 11/1996 | Vaillancourt |
| 5,575,777 A | 11/1996 | Cover et al. |
| 5,591,138 A | 1/1997 | Vaillancourt |
| 5,601,536 A | 2/1997 | Crawford et al. |
| 5,643,216 A | 7/1997 | White |
| 5,669,891 A | 9/1997 | Vaillancourt |
| 5,676,656 A | 10/1997 | Brimhall |
| 5,676,658 A | 10/1997 | Erskine |
| 5,688,253 A | 11/1997 | Paradis |
| 5,697,914 A | 12/1997 | Brimhall |
| 5,697,915 A | 12/1997 | Lynn |
| 5,702,367 A | 12/1997 | Cover et al. |
| 5,702,371 A | 12/1997 | Bierman |
| 5,704,914 A | 1/1998 | Stocking et al. |
| 5,713,876 A | 2/1998 | Bogert et al. |
| 5,725,499 A | 3/1998 | Silverstein et al. |
| 5,727,770 A | 3/1998 | Dennis |
| 5,735,826 A | 4/1998 | Richmond |
| 5,735,827 A | 4/1998 | Adwers et al. |
| 5,740,810 A | 4/1998 | Johnson et al. |
| 5,743,884 A | 4/1998 | Hasson et al. |

(56) References Cited

U.S. PATENT DOCUMENTS

| | | |
|---|---|---|
| 5,746,727 A | 5/1998 | Graves et al. |
| 5,749,857 A | 5/1998 | Cuppy |
| 5,755,709 A | 5/1998 | Cuppy |
| 5,769,825 A | 6/1998 | Lynn |
| 5,788,675 A | 8/1998 | Mayer |
| 5,810,780 A | 9/1998 | Brimhall |
| 5,827,221 A | 10/1998 | Phelps |
| 5,830,184 A | 11/1998 | Basta |
| 5,833,662 A | 11/1998 | Stevens |
| 5,846,227 A | 12/1998 | Osterlind |
| 5,879,330 A | 3/1999 | Bell |
| 5,902,274 A | 5/1999 | Yamamoto et al. |
| 5,911,705 A | 6/1999 | Howell |
| 5,913,845 A | 6/1999 | Brimhall |
| 5,916,199 A | 6/1999 | Miles |
| 5,935,110 A | 8/1999 | Brimhall |
| 5,954,698 A | 9/1999 | Pike |
| 5,957,887 A | 9/1999 | Oesterlind et al. |
| 5,989,220 A | 11/1999 | Shaw et al. |
| 5,997,504 A | 12/1999 | Bell |
| 6,001,080 A | 12/1999 | Kuracina et al. |
| 6,004,294 A | 12/1999 | Brimhall et al. |
| 6,022,339 A | 2/2000 | Fowles et al. |
| 6,027,480 A | 2/2000 | Davis et al. |
| 6,033,382 A | 3/2000 | Basta |
| 6,056,718 A | 5/2000 | Funerburk et al. |
| 6,077,244 A | 6/2000 | Botich et al. |
| 6,077,248 A | 6/2000 | Zumschlinge |
| 6,086,564 A | 7/2000 | McLaughlin |
| 6,142,981 A | 11/2000 | Heck et al. |
| 6,149,632 A | 11/2000 | Landuyt |
| 6,152,913 A | 11/2000 | Feith et al. |
| 6,162,206 A | 12/2000 | Bindokas et al. |
| 6,168,137 B1 | 1/2001 | Paradis |
| 6,171,287 B1 | 1/2001 | Lynn et al. |
| 6,197,007 B1 | 3/2001 | Thorne et al. |
| 6,210,624 B1 | 4/2001 | Mayer |
| 6,213,978 B1 | 4/2001 | Voyten |
| 6,221,048 B1 | 4/2001 | Phelps |
| 6,228,065 B1 | 5/2001 | Lynn |
| 6,261,259 B1 | 7/2001 | Bell |
| 6,261,268 B1 | 7/2001 | Mayer |
| 6,273,869 B1 | 8/2001 | Vaillancourt |
| 6,273,871 B1 | 8/2001 | Davis et al. |
| RE37,357 E | 9/2001 | Lynn |
| 6,299,602 B1 | 10/2001 | Miller et al. |
| 6,302,866 B1 | 10/2001 | Marggi |
| 6,342,120 B1 | 1/2002 | Basta |
| 6,375,639 B1 | 4/2002 | Duplessie et al. |
| 6,379,333 B1 | 4/2002 | Brimhall et al. |
| 6,379,337 B1 | 4/2002 | Mohammad |
| 6,443,929 B1 | 9/2002 | Kuracina et al. |
| 6,506,181 B2 | 1/2003 | Meng et al. |
| 6,520,938 B1 | 2/2003 | Funderburk et al. |
| 6,569,120 B1 | 5/2003 | Green et al. |
| RE38,145 E | 6/2003 | Lynn |
| 6,572,586 B1 | 6/2003 | Wojcik |
| 6,572,588 B1 | 6/2003 | Bierman |
| 6,572,591 B2 | 6/2003 | Mayer |
| 6,595,955 B2 | 7/2003 | Ferguson et al. |
| 6,623,461 B1 | 9/2003 | Wilkinson et al. |
| 6,638,252 B2 | 10/2003 | Moulton et al. |
| 6,652,490 B2 | 11/2003 | Howell |
| 6,663,599 B2 | 12/2003 | Osborne et al. |
| 6,673,046 B2 | 1/2004 | Bierman et al. |
| 6,692,468 B1 | 2/2004 | Waldenburg |
| 6,699,221 B2 | 3/2004 | Vaillancourt |
| 6,712,790 B2 | 3/2004 | Prestidge et al. |
| 6,719,726 B2 | 4/2004 | Meng et al. |
| 6,719,727 B2 | 4/2004 | Brimhall et al. |
| 6,730,096 B2 | 5/2004 | Basta |
| 6,740,277 B2 | 5/2004 | Howell et al. |
| 6,749,588 B1 | 6/2004 | Howell et al. |
| 6,761,706 B2 | 7/2004 | Vaillancourt |
| 6,776,775 B1 | 8/2004 | Mohammad |
| 6,805,860 B1 | 10/2004 | Alt |
| 6,811,545 B2 | 11/2004 | Vaillancourt |
| 6,837,875 B1 | 1/2005 | Bierman |
| 6,849,051 B2 | 2/2005 | Sramek et al. |
| 6,902,546 B2 * | 6/2005 | Ferguson ............ A61M 5/3273 128/919 |
| 6,905,483 B2 | 6/2005 | Newby et al. |
| 6,908,459 B2 | 6/2005 | Harding et al. |
| 6,921,391 B1 | 7/2005 | Barker et al. |
| 6,926,721 B2 | 8/2005 | Basta |
| 6,953,448 B2 | 10/2005 | Moulton et al. |
| 6,955,659 B1 | 10/2005 | Carter |
| 6,972,002 B2 | 12/2005 | Thorne |
| 6,981,965 B2 | 1/2006 | Luther et al. |
| 6,981,966 B2 | 1/2006 | Green et al. |
| 6,984,223 B2 | 1/2006 | Newby et al. |
| RE38,996 E | 2/2006 | Crawford et al. |
| 6,997,902 B2 | 2/2006 | Thorne et al. |
| 6,997,913 B2 | 2/2006 | Wilkinson |
| 6,997,917 B2 | 2/2006 | Niedospial, Jr. et al. |
| 7,004,934 B2 | 2/2006 | Vaillancourt |
| 7,008,406 B2 | 3/2006 | Mayer |
| 7,022,111 B2 | 4/2006 | Duplessie et al. |
| 7,033,339 B1 | 4/2006 | Lynn |
| 7,060,055 B2 | 6/2006 | Wilkinson et al. |
| 7,060,060 B1 | 6/2006 | Simpson et al. |
| 7,090,660 B2 | 8/2006 | Roberts et al. |
| 7,090,661 B2 | 8/2006 | Morris et al. |
| 7,112,191 B2 | 9/2006 | Daga |
| RE39,334 E | 10/2006 | Lynn |
| 7,125,398 B2 | 10/2006 | Garcia, Jr. |
| 7,141,040 B2 | 11/2006 | Lichtenberg |
| 7,147,622 B2 | 12/2006 | Gutierrez |
| 7,220,249 B2 | 5/2007 | Hwang et al. |
| 7,258,680 B2 | 8/2007 | Mogensen et al. |
| 7,344,516 B2 | 3/2008 | Erskine |
| 7,347,842 B2 | 3/2008 | Thorne et al. |
| 7,351,230 B2 | 4/2008 | Smith et al. |
| 7,354,422 B2 | 4/2008 | Riesenberger et al. |
| 7,396,346 B2 | 7/2008 | Nakajima |
| 7,413,562 B2 | 8/2008 | Ferguson et al. |
| 7,435,238 B2 | 10/2008 | Reid |
| 7,445,611 B2 | 11/2008 | Osborne et al. |
| 7,470,261 B2 | 12/2008 | Lynn |
| 7,481,797 B2 | 1/2009 | Mahurkar |
| 7,507,222 B2 | 3/2009 | Cindrich et al. |
| 7,569,033 B2 | 8/2009 | Greene et al. |
| 7,604,616 B2 | 10/2009 | Thoresen et al. |
| 7,611,499 B2 | 11/2009 | Woehr et al. |
| 7,615,033 B2 | 11/2009 | Leong |
| 7,618,395 B2 | 11/2009 | Ferguson |
| 7,625,360 B2 | 12/2009 | Woehr et al. |
| 7,635,357 B2 | 12/2009 | Mayer |
| 7,651,481 B2 | 1/2010 | Raybuck |
| 7,654,988 B2 | 2/2010 | Moulton et al. |
| 7,658,725 B2 | 2/2010 | Bialecki et al. |
| 7,666,166 B1 | 2/2010 | Emmert et al. |
| 7,670,299 B2 | 3/2010 | Beckman et al. |
| 7,670,317 B2 | 3/2010 | Cindrich et al. |
| 7,682,339 B2 | 3/2010 | Fujii |
| 7,694,403 B2 | 4/2010 | Moulton |
| 7,699,814 B2 | 4/2010 | Lande |
| 7,713,243 B2 | 5/2010 | Hillman |
| 7,713,250 B2 | 5/2010 | Harding et al. |
| 7,717,882 B2 | 5/2010 | Harding |
| 7,722,569 B2 | 5/2010 | Söederholm et al. |
| 7,736,332 B2 | 6/2010 | Carlyon et al. |
| 7,736,337 B2 | 6/2010 | Diep et al. |
| 7,736,342 B2 | 6/2010 | Abriles et al. |
| 7,740,615 B2 | 6/2010 | Shaw et al. |
| 7,744,572 B2 | 6/2010 | Bierman |
| 7,749,254 B2 | 7/2010 | Sobelman et al. |
| 7,762,993 B2 | 7/2010 | Perez |
| 7,763,199 B2 | 7/2010 | Fangrow, Jr. |
| 7,766,879 B2 | 8/2010 | Tan et al. |
| 7,766,897 B2 | 8/2010 | Ramsey et al. |
| 7,771,412 B2 | 8/2010 | Anderson et al. |
| 7,776,017 B2 | 8/2010 | Ponzi et al. |
| 7,798,991 B2 | 9/2010 | Insignares |

(56) References Cited

U.S. PATENT DOCUMENTS

| | | |
|---|---|---|
| 7,798,994 B2 | 9/2010 | Brimhall |
| 7,799,000 B2 | 9/2010 | Silich |
| 7,806,869 B2 | 10/2010 | Nilsson et al. |
| 7,833,201 B2 | 11/2010 | Carlyon et al. |
| 7,862,547 B2 | 1/2011 | Ferguson et al. |
| 7,887,515 B2 | 2/2011 | Bierman |
| 7,892,216 B2 | 2/2011 | Fangrow, Jr. |
| 7,918,828 B2 | 4/2011 | Lundgaard et al. |
| 7,931,615 B2 | 4/2011 | Fangrow, Jr. |
| 7,959,613 B2 | 6/2011 | Rhad et al. |
| 7,972,313 B2 | 7/2011 | Woehr et al. |
| 8,012,145 B2 | 9/2011 | Cawley |
| 8,025,644 B2 | 9/2011 | Chong et al. |
| 8,042,689 B2 | 10/2011 | Fröjd et al. |
| 8,043,265 B2 | 10/2011 | Abe et al. |
| 8,048,031 B2 | 11/2011 | Shaw et al. |
| 8,062,262 B2 | 11/2011 | Christensen et al. |
| 8,066,669 B2 | 11/2011 | Christensen et al. |
| 8,066,670 B2 | 11/2011 | Cluff et al. |
| 8,066,675 B2 | 11/2011 | Cindrich et al. |
| 8,066,678 B2 | 11/2011 | Vaillancourt et al. |
| 8,070,725 B2 | 12/2011 | Christensen |
| 8,079,979 B2 | 12/2011 | Moorehead |
| 8,083,728 B2 | 12/2011 | Rome |
| 8,092,435 B2 | 1/2012 | Beling et al. |
| 8,105,286 B2 | 1/2012 | Anderson et al. |
| 8,105,288 B2 | 1/2012 | Keyser et al. |
| 8,122,923 B2 | 2/2012 | Krause et al. |
| 8,123,738 B2 | 2/2012 | Vaillancourt |
| 8,133,202 B2 | 3/2012 | Marsh |
| 8,133,206 B2 | 3/2012 | Greene et al. |
| 8,147,455 B2 | 4/2012 | Butts et al. |
| 8,147,465 B2 | 4/2012 | Kern |
| 8,157,770 B2 | 4/2012 | Elwell et al. |
| 8,162,882 B2 | 4/2012 | Rubinstein et al. |
| 8,162,896 B2 | 4/2012 | Tan |
| 8,162,914 B2 | 4/2012 | Kraushaar et al. |
| 8,163,237 B2 | 4/2012 | Crawford et al. |
| 8,172,803 B2 | 5/2012 | Morrissey et al. |
| 8,172,825 B2 | 5/2012 | Solomon et al. |
| 8,177,745 B2 | 5/2012 | Brechbuehler et al. |
| 8,177,753 B2 | 5/2012 | Vitullo et al. |
| 8,177,754 B2 | 5/2012 | Barnes |
| 8,177,755 B2 | 5/2012 | Berry et al. |
| 8,177,760 B2 | 5/2012 | Rome et al. |
| 8,177,762 B2 | 5/2012 | Beasley et al. |
| 8,177,772 B2 | 5/2012 | Christensen et al. |
| 8,182,448 B2 | 5/2012 | Emmert et al. |
| 8,197,452 B2 | 6/2012 | Harding et al. |
| 8,197,466 B2 | 6/2012 | Yokota et al. |
| 8,211,070 B2 | 7/2012 | Woehr et al. |
| 8,226,612 B2 | 7/2012 | Nakajima |
| 8,251,950 B2 | 8/2012 | Albert et al. |
| 8,273,056 B2 | 9/2012 | Kuracina et al. |
| 8,277,424 B2 | 10/2012 | Pan |
| 8,287,518 B2 | 10/2012 | Kitani et al. |
| 8,298,195 B2 | 10/2012 | Peppel |
| 8,313,459 B2 | 11/2012 | Kiehne |
| 8,313,469 B2 | 11/2012 | Fiser |
| 8,323,249 B2 | 12/2012 | White et al. |
| 8,337,471 B2 | 12/2012 | Baid |
| 8,337,483 B2 | 12/2012 | Harding et al. |
| 8,357,121 B2 | 1/2013 | Burkholz |
| 8,361,408 B2 | 1/2013 | Lynn |
| 8,366,676 B2 | 2/2013 | Harding et al. |
| 8,377,010 B2 | 2/2013 | Harding et al. |
| 8,377,040 B2 | 2/2013 | Burkholz et al. |
| 8,382,718 B2 | 2/2013 | Woehr |
| 8,382,721 B2 | 2/2013 | Woehr et al. |
| 8,398,597 B2 | 3/2013 | Brimhall |
| 8,398,598 B2 | 3/2013 | Carlyon et al. |
| 8,403,894 B2 | 3/2013 | Lynn et al. |
| 8,403,905 B2 | 3/2013 | Yow |
| 8,408,226 B2 | 4/2013 | Raines et al. |
| 8,409,165 B2 | 4/2013 | Niedospial, Jr. et al. |
| 8,419,688 B2 | 4/2013 | Woehr et al. |
| 8,430,850 B2 | 4/2013 | Gyrn et al. |
| 8,439,877 B2 | 5/2013 | Burkholz |
| 8,439,891 B1 | 5/2013 | Milligan |
| 8,444,605 B2 | 5/2013 | Kuracina et al. |
| 8,460,247 B2 | 6/2013 | Woehr et al. |
| 8,465,441 B2 | 6/2013 | Srivatsa et al. |
| 8,511,352 B2 | 8/2013 | Krause et al. |
| 8,529,524 B2 | 9/2013 | Newton et al. |
| 8,545,454 B2 | 10/2013 | Kuracina et al. |
| 8,556,854 B2 | 10/2013 | Zivkovic et al. |
| 8,556,855 B2 | 10/2013 | Zivkovic et al. |
| 8,568,372 B2 | 10/2013 | Woehr et al. |
| 8,591,469 B2 | 11/2013 | Keyser et al. |
| 8,622,967 B2 | 1/2014 | Davis et al. |
| 8,628,497 B2 | 1/2014 | Finnestad et al. |
| 8,636,697 B2 | 1/2014 | Scheurer et al. |
| 8,647,301 B2 | 2/2014 | Bialecki et al. |
| 8,652,104 B2 | 2/2014 | Goral et al. |
| 8,657,788 B2 | 2/2014 | Fangrow, Jr. |
| 8,657,790 B2 | 2/2014 | Tal et al. |
| 8,663,169 B2 | 3/2014 | Emmert et al. |
| 8,668,674 B2 | 3/2014 | White et al. |
| 8,671,964 B2 | 3/2014 | Py |
| 8,684,994 B2 | 4/2014 | Lev et al. |
| 8,702,675 B2 | 4/2014 | Imai |
| 8,715,222 B2 | 5/2014 | Truitt et al. |
| 8,715,247 B2 | 5/2014 | Mansour et al. |
| 8,715,250 B2 | 5/2014 | Tremblay |
| 8,721,627 B2 | 5/2014 | Alpert |
| 8,728,035 B2 | 5/2014 | Warring et al. |
| 8,771,230 B2 | 7/2014 | White et al. |
| 8,784,387 B2 | 7/2014 | Woehr |
| 8,790,310 B2 | 7/2014 | White et al. |
| 8,801,678 B2 | 8/2014 | Panian et al. |
| 8,814,833 B2 | 8/2014 | Farrell et al. |
| 8,827,965 B2 | 9/2014 | Woehr et al. |
| 8,834,422 B2 | 9/2014 | Walker et al. |
| 8,834,432 B2 | 9/2014 | Winsor et al. |
| 8,840,577 B1 | 9/2014 | Zollinger et al. |
| 8,858,503 B2 | 10/2014 | Burkholz et al. |
| 8,870,835 B2 | 10/2014 | Baid |
| 8,870,846 B2 | 10/2014 | Davis et al. |
| 8,876,784 B2 | 11/2014 | Coete, Sr. et al. |
| 8,882,742 B2 | 11/2014 | Dikeman et al. |
| 8,900,192 B2 | 12/2014 | Anderson et al. |
| 8,900,199 B2 | 12/2014 | Kawai et al. |
| 8,910,919 B2 | 12/2014 | Bonnal et al. |
| 8,915,891 B2 | 12/2014 | Bornhoft |
| 8,932,259 B2 | 1/2015 | Stout et al. |
| 8,951,233 B2 | 2/2015 | Mansour |
| 8,956,328 B2 | 2/2015 | Antonucci |
| 8,956,330 B2 | 2/2015 | Fangrow, Jr. |
| 8,968,252 B2 | 3/2015 | White et al. |
| 8,968,261 B2 | 3/2015 | Kimball et al. |
| 8,968,271 B2 | 3/2015 | Guala |
| 8,974,425 B2 | 3/2015 | Tachizaki et al. |
| 8,979,795 B2 | 3/2015 | Bokelman et al. |
| 8,979,804 B2 | 3/2015 | Ho et al. |
| 8,986,227 B2 | 3/2015 | Belson |
| 8,998,851 B2 | 4/2015 | Constantineau et al. |
| 9,011,382 B2 | 4/2015 | Nilsson et al. |
| 9,017,288 B1 | 4/2015 | Starnes |
| 9,017,295 B2 | 4/2015 | Pan |
| 9,032,997 B2 | 5/2015 | Abura et al. |
| 9,033,927 B2 | 5/2015 | Maan et al. |
| 9,033,952 B2 | 5/2015 | Chen |
| 9,039,047 B2 | 5/2015 | Imai |
| 9,044,552 B2 | 6/2015 | Schraga |
| 9,044,585 B2 | 6/2015 | Masuda et al. |
| 9,050,128 B2 | 6/2015 | Ros |
| 9,056,188 B2 | 6/2015 | Hager et al. |
| 9,061,130 B2 | 6/2015 | Truitt et al. |
| 9,067,049 B2 | 6/2015 | Panian et al. |
| 9,089,680 B2 | 7/2015 | Ueda et al. |
| 9,089,681 B2 | 7/2015 | Ueda et al. |
| 9,089,682 B2 | 7/2015 | Yeh et al. |
| 9,095,679 B2 | 8/2015 | Nishimura et al. |
| 9,095,683 B2 | 8/2015 | Hall et al. |

(56) References Cited

U.S. PATENT DOCUMENTS

| | | |
|---|---|---|
| 9,114,231 B2 | 8/2015 | Woehr et al. |
| 9,114,241 B2 | 8/2015 | Stout et al. |
| 9,114,244 B2 | 8/2015 | Yeh et al. |
| 9,119,950 B2 | 9/2015 | Mansour et al. |
| 9,126,017 B2 | 9/2015 | Albert et al. |
| 9,138,572 B2 | 9/2015 | Zeytoonian et al. |
| 9,144,672 B2 | 9/2015 | Mansour et al. |
| 9,162,029 B2 | 10/2015 | Zollinger |
| 9,162,037 B2 | 10/2015 | Belson et al. |
| 9,198,831 B2 | 12/2015 | Rogers |
| 9,199,062 B2 | 12/2015 | Liska et al. |
| 9,199,063 B2 | 12/2015 | Baid |
| 9,212,772 B2 | 12/2015 | Ho et al. |
| 9,220,871 B2 | 12/2015 | Thörne et al. |
| 9,227,038 B2 | 1/2016 | Woehr |
| 9,233,229 B2 | 1/2016 | Emmert et al. |
| 9,234,616 B2 | 1/2016 | Carrez et al. |
| 9,238,128 B2 | 1/2016 | Yamaguchi et al. |
| 9,238,130 B2 | 1/2016 | Mouri |
| 9,259,533 B2 | 2/2016 | Weilbacher et al. |
| 9,259,537 B2 | 2/2016 | Baney et al. |
| 9,265,882 B2 | 2/2016 | Ito |
| 9,271,668 B2 | 3/2016 | Crawford et al. |
| 9,278,180 B2 | 3/2016 | Wong |
| 9,278,195 B2 | 3/2016 | Erskine |
| 9,278,205 B2 | 3/2016 | Quach et al. |
| 9,289,237 B2 | 3/2016 | Woehr et al. |
| 9,289,588 B2 | 3/2016 | Chen |
| 9,308,352 B2 | 4/2016 | Teoh et al. |
| 9,308,353 B2 | 4/2016 | Shaw et al. |
| 9,308,354 B2 | 4/2016 | Farrell et al. |
| 9,314,604 B2 | 4/2016 | Bonnal et al. |
| 9,320,469 B2 | 4/2016 | Shaw et al. |
| 9,320,858 B2 | 4/2016 | Grimm et al. |
| 9,320,859 B2 | 4/2016 | Grimm et al. |
| 9,320,860 B2 | 4/2016 | Grimm et al. |
| 9,345,641 B2 | 5/2016 | Krause et al. |
| 9,352,127 B2 | 5/2016 | Yeh et al. |
| 9,370,466 B2 | 6/2016 | Garfield et al. |
| 9,370,641 B2 | 6/2016 | Woehr et al. |
| 9,370,651 B2 | 6/2016 | Zollinger et al. |
| 9,375,551 B2 | 6/2016 | Harding |
| 9,375,552 B2 | 6/2016 | Tremblay |
| 9,381,324 B2 | 7/2016 | Fuchs et al. |
| 9,381,337 B2 | 7/2016 | Carter et al. |
| 9,393,398 B2 | 7/2016 | Truitt et al. |
| 9,399,116 B2 | 7/2016 | Goral et al. |
| 9,399,119 B2 | 7/2016 | Kuracina et al. |
| 9,399,120 B2 | 7/2016 | Burkholz |
| 9,408,632 B2 | 8/2016 | Erskine |
| 9,409,007 B2 | 8/2016 | Yeh |
| 9,415,192 B2 | 8/2016 | Kuracina et al. |
| 9,421,345 B2 | 8/2016 | Woehr et al. |
| 9,421,352 B2 | 8/2016 | Butts et al. |
| 9,427,549 B2 | 8/2016 | Woehr et al. |
| 9,433,708 B2 | 9/2016 | Eddy |
| 9,433,758 B2 | 9/2016 | Farley et al. |
| 9,522,255 B2 | 12/2016 | Knutsson |
| 9,592,366 B2 | 3/2017 | White et al. |
| 9,809,355 B2 | 11/2017 | Solomon et al. |
| 9,827,398 B2 | 11/2017 | White et al. |
| 9,962,526 B2 | 5/2018 | White et al. |
| 10,086,170 B2 | 10/2018 | Chhikara et al. |
| 10,159,818 B2 | 12/2018 | Farrell et al. |
| 10,569,057 B2 | 2/2020 | White et al. |
| 10,668,252 B2 | 6/2020 | White et al. |
| 2001/0041871 A1* | 11/2001 | Brimhall ............ A61M 25/0631 604/167.02 |
| 2002/0045843 A1 | 4/2002 | Barker et al. |
| 2002/0165497 A1 | 11/2002 | Greene et al. |
| 2002/0169418 A1 | 11/2002 | Menzi et al. |
| 2002/0177814 A1* | 11/2002 | Meng ................ A61M 25/0606 604/164.07 |
| 2003/0032922 A1 | 2/2003 | Moorehead |
| 2003/0073956 A1 | 4/2003 | Hoffman et al. |
| 2003/0083620 A1 | 5/2003 | Luther et al. |
| 2003/0083621 A1 | 5/2003 | Shaw et al. |
| 2003/0120222 A1 | 6/2003 | Vaillancourt |
| 2003/0181871 A1 | 9/2003 | Wilkinson et al. |
| 2003/0195479 A1 | 10/2003 | Kuracina et al. |
| 2003/0199827 A1 | 10/2003 | Thorne |
| 2004/0010227 A1 | 1/2004 | Riesenberger et al. |
| 2004/0030294 A1 | 2/2004 | Mahurkar |
| 2004/0064102 A1 | 4/2004 | Yamada |
| 2004/0097888 A1 | 5/2004 | Gutierrez |
| 2004/0102735 A1 | 5/2004 | Moulton et al. |
| 2004/0106903 A1 | 6/2004 | Shue et al. |
| 2004/0111059 A1 | 6/2004 | Howlett et al. |
| 2004/0116855 A1 | 6/2004 | Popov et al. |
| 2004/0127856 A1 | 7/2004 | Johnson |
| 2004/0143216 A1 | 7/2004 | Douglas et al. |
| 2004/0181192 A1 | 9/2004 | Cuppy |
| 2004/0206416 A1 | 10/2004 | Paradis |
| 2004/0267210 A1 | 12/2004 | Popovsky |
| 2005/0027263 A1 | 2/2005 | Woehr et al. |
| 2005/0043709 A1 | 2/2005 | Brimhall et al. |
| 2005/0045192 A1 | 3/2005 | Fulton et al. |
| 2005/0059933 A1 | 3/2005 | Johnson |
| 2005/0113755 A1 | 5/2005 | Greene et al. |
| 2005/0131350 A1 | 6/2005 | Shaw et al. |
| 2005/0192535 A1 | 9/2005 | Takagi et al. |
| 2006/0015071 A1 | 1/2006 | Fitzgerald |
| 2006/0015075 A1 | 1/2006 | Blanco et al. |
| 2006/0030815 A1 | 2/2006 | Csincsura et al. |
| 2006/0060892 A1 | 3/2006 | Propp |
| 2006/0094983 A1 | 5/2006 | Burbank et al. |
| 2006/0106335 A1 | 5/2006 | Putter et al. |
| 2006/0116638 A1 | 6/2006 | Woehr et al. |
| 2006/0155258 A1 | 7/2006 | Rogers et al. |
| 2006/0189942 A1 | 8/2006 | Chang et al. |
| 2006/0247577 A1 | 11/2006 | Wright |
| 2006/0253076 A1 | 11/2006 | Butts et al. |
| 2006/0264833 A1 | 11/2006 | Moulton |
| 2006/0270994 A1 | 11/2006 | Bierman |
| 2007/0016149 A1 | 1/2007 | Hunn et al. |
| 2007/0038179 A1 | 2/2007 | Bialecki et al. |
| 2007/0038182 A1 | 2/2007 | Bialecki et al. |
| 2007/0038183 A1 | 2/2007 | Bialecki et al. |
| 2007/0038185 A1 | 2/2007 | Albert et al. |
| 2007/0038186 A1 | 2/2007 | Sutton et al. |
| 2007/0038187 A1 | 2/2007 | Albert et al. |
| 2007/0060892 A1 | 3/2007 | Propp |
| 2007/0066958 A1 | 3/2007 | Wright |
| 2007/0066960 A1 | 3/2007 | Jones et al. |
| 2007/0073221 A1 | 3/2007 | Bialecki et al. |
| 2007/0078400 A1 | 4/2007 | Gesler, III |
| 2007/0079894 A1 | 4/2007 | Krause et al. |
| 2007/0129689 A1 | 6/2007 | Woehr et al. |
| 2007/0142785 A1 | 6/2007 | Lundgaard et al. |
| 2007/0161950 A1 | 7/2007 | Carlyon et al. |
| 2007/0173768 A2 | 7/2007 | Bierman |
| 2007/0179446 A1 | 8/2007 | Carrez et al. |
| 2007/0185454 A1 | 8/2007 | Fangrow |
| 2007/0185455 A1 | 8/2007 | Fangrow |
| 2007/0191776 A1 | 8/2007 | Bialecki et al. |
| 2007/0191777 A1 | 8/2007 | King |
| 2007/0244438 A1 | 10/2007 | Perez |
| 2007/0250011 A1 | 10/2007 | Lee |
| 2007/0250057 A1 | 10/2007 | Nobis et al. |
| 2007/0255212 A1 | 11/2007 | Smith et al. |
| 2007/0265572 A1 | 11/2007 | Smith et al. |
| 2007/0270754 A1 | 11/2007 | Soderholm et al. |
| 2007/0270758 A1 | 11/2007 | Hanner et al. |
| 2008/0039796 A1 | 2/2008 | Nakajima |
| 2008/0051726 A1 | 2/2008 | Lee et al. |
| 2008/0097315 A1 | 4/2008 | Miner et al. |
| 2008/0108944 A1 | 5/2008 | Woehr et al. |
| 2008/0125717 A1 | 5/2008 | Shue et al. |
| 2008/0132846 A1 | 6/2008 | Shue et al. |
| 2008/0135443 A1 | 6/2008 | Frojd et al. |
| 2008/0140004 A1 | 6/2008 | Thorne et al. |
| 2008/0140011 A1 | 6/2008 | Hager et al. |
| 2008/0147009 A1 | 6/2008 | Nilsson et al. |
| 2008/0195033 A1 | 8/2008 | Eagleson et al. |

(56) References Cited

U.S. PATENT DOCUMENTS

| | | |
|---|---|---|
| 2008/0200791 A1 | 8/2008 | Simpson et al. |
| 2008/0215009 A1 | 9/2008 | Shaw et al. |
| 2008/0228144 A1 | 9/2008 | Liniger et al. |
| 2008/0262431 A1 | 10/2008 | Anderson et al. |
| 2008/0287876 A1 | 11/2008 | Shue et al. |
| 2008/0300543 A1 | 12/2008 | Abriles et al. |
| 2008/0300574 A1 | 12/2008 | Belson et al. |
| 2009/0012480 A1 | 1/2009 | Moulton et al. |
| 2009/0036836 A1 | 2/2009 | Nystrom et al. |
| 2009/0036914 A1 | 2/2009 | Houser |
| 2009/0043260 A1 | 2/2009 | Bierman |
| 2009/0069751 A1 | 3/2009 | Curtis et al. |
| 2009/0076435 A1 | 3/2009 | Melsheimer et al. |
| 2009/0082732 A1 | 3/2009 | Hillman |
| 2009/0082733 A1 | 3/2009 | Fujii |
| 2009/0124981 A1 | 5/2009 | Evans |
| 2009/0131870 A1 | 5/2009 | Fiser |
| 2009/0131872 A1 | 5/2009 | Popov |
| 2009/0137958 A1 | 5/2009 | Erskine |
| 2009/0137961 A1 | 5/2009 | Bracken |
| 2009/0157013 A1 | 6/2009 | Wong |
| 2009/0163861 A1 | 6/2009 | Carlyon |
| 2009/0177167 A1 | 7/2009 | Kuracina et al. |
| 2009/0221961 A1 | 9/2009 | Tal et al. |
| 2009/0227896 A1 | 9/2009 | Tan et al. |
| 2009/0247952 A1 | 10/2009 | Weilbacher et al. |
| 2009/0299295 A1 | 12/2009 | Rubinstein et al. |
| 2009/0306602 A1 | 12/2009 | Elwell et al. |
| 2010/0004604 A1 | 1/2010 | Stearns |
| 2010/0016804 A1 | 1/2010 | Muskatello et al. |
| 2010/0036331 A1 | 2/2010 | Sen |
| 2010/0094310 A1 | 4/2010 | Warring et al. |
| 2010/0106135 A1 | 4/2010 | Radmand |
| 2010/0114063 A1 | 5/2010 | Recinella et al. |
| 2010/0137815 A1 | 6/2010 | Kuracina et al. |
| 2010/0137833 A1 | 6/2010 | Glynn |
| 2010/0168675 A1 | 7/2010 | Cindrich et al. |
| 2010/0204648 A1 | 8/2010 | Stout et al. |
| 2010/0210934 A1 | 8/2010 | Belson |
| 2010/0222746 A1 | 9/2010 | Burkholz |
| 2010/0234804 A1 | 9/2010 | Hiejima et al. |
| 2010/0241088 A1 | 9/2010 | Ranalletta et al. |
| 2010/0262038 A1 | 10/2010 | Tan et al. |
| 2010/0262083 A1 | 10/2010 | Grunhut et al. |
| 2010/0268156 A1 | 10/2010 | Milacek et al. |
| 2010/0274199 A1 | 10/2010 | Weston |
| 2010/0286615 A1 | 11/2010 | Gyrn et al. |
| 2010/0286620 A1 | 11/2010 | Edginton et al. |
| 2010/0286623 A1 | 11/2010 | Liversidge |
| 2010/0292673 A1 | 11/2010 | Korogi et al. |
| 2010/0305519 A1 | 12/2010 | McKinnon et al. |
| 2010/0318063 A1 | 12/2010 | Soll |
| 2011/0015573 A1 | 1/2011 | Maan et al. |
| 2011/0021994 A1 | 1/2011 | Anderson et al. |
| 2011/0040281 A1 | 2/2011 | White et al. |
| 2011/0054404 A1 | 3/2011 | Tanabe et al. |
| 2011/0060288 A1 | 3/2011 | Carlyon et al. |
| 2011/0077592 A1 | 3/2011 | Takemoto |
| 2011/0125096 A1 | 5/2011 | Baid |
| 2011/0125097 A1 | 5/2011 | Shaw et al. |
| 2011/0166475 A1 | 7/2011 | Crawford et al. |
| 2011/0178427 A1 | 7/2011 | Tan et al. |
| 2011/0178464 A1 | 7/2011 | Rawls |
| 2011/0178478 A1 | 7/2011 | Huet et al. |
| 2011/0196260 A1 | 8/2011 | Melsheimer et al. |
| 2011/0208124 A1 | 8/2011 | Rhad et al. |
| 2011/0213307 A1 | 9/2011 | Kawai et al. |
| 2011/0224617 A1 | 9/2011 | Miner |
| 2011/0306933 A1 | 12/2011 | Djordjevic et al. |
| 2011/0319859 A1 | 12/2011 | Zeytoonian et al. |
| 2012/0010577 A1 | 1/2012 | Liska et al. |
| 2012/0016312 A1 | 1/2012 | Brown et al. |
| 2012/0022464 A1 | 1/2012 | Zivkovic et al. |
| 2012/0191010 A1 | 1/2012 | Cabot |
| 2012/0035552 A1 | 2/2012 | Woehr |
| 2012/0041371 A1 | 2/2012 | Tal et al. |
| 2012/0041377 A1 | 2/2012 | Haak |
| 2012/0056746 A1 | 3/2012 | Kaigler et al. |
| 2012/0065612 A1 | 3/2012 | Stout et al. |
| 2012/0109077 A1 | 5/2012 | Ryan |
| 2012/0123381 A1 | 5/2012 | Krause et al. |
| 2012/0143151 A1 | 6/2012 | Low et al. |
| 2012/0150117 A1 | 6/2012 | Andino |
| 2012/0150121 A1 | 6/2012 | Silverman et al. |
| 2012/0153201 A1 | 6/2012 | Larose et al. |
| 2012/0184910 A1 | 7/2012 | Woehr |
| 2012/0191071 A1 | 7/2012 | Butts et al. |
| 2012/0197200 A1 | 8/2012 | Belson |
| 2012/0197205 A1 | 8/2012 | Peters |
| 2012/0220944 A1 | 8/2012 | Charlez |
| 2012/0220955 A1 | 8/2012 | Maseda et al. |
| 2012/0220956 A1 | 8/2012 | Kuracina et al. |
| 2012/0220984 A1 | 8/2012 | Christensen et al. |
| 2012/0226240 A1 | 9/2012 | Bedford et al. |
| 2012/0259293 A1 | 10/2012 | Bialecki et al. |
| 2012/0316536 A1 | 12/2012 | Carrez et al. |
| 2012/0323181 A1 | 12/2012 | Shaw et al. |
| 2012/0330248 A1 | 12/2012 | Woehr |
| 2013/0030370 A1 | 1/2013 | Walker et al. |
| 2013/0041313 A1 | 2/2013 | Chung |
| 2013/0053781 A1 | 2/2013 | Woehr et al. |
| 2013/0053815 A1 | 2/2013 | Mucientes et al. |
| 2013/0060197 A1 | 3/2013 | Woehr et al. |
| 2013/0060198 A1 | 3/2013 | Woehr et al. |
| 2013/0060199 A1 | 3/2013 | Baid |
| 2013/0060201 A1 | 3/2013 | Popov |
| 2013/0060205 A1 | 3/2013 | Mansour et al. |
| 2013/0066276 A1 | 3/2013 | Ito et al. |
| 2013/0079730 A1 | 3/2013 | Mosler et al. |
| 2013/0096504 A1 | 4/2013 | Walker et al. |
| 2013/0110036 A1 | 5/2013 | Fojtik |
| 2013/0116598 A1 | 5/2013 | Howell et al. |
| 2013/0150784 A1 | 6/2013 | Rodriguez Lelis et al. |
| 2013/0158506 A1 | 6/2013 | White et al. |
| 2013/0178798 A1 | 7/2013 | Pearson et al. |
| 2013/0178825 A1 | 7/2013 | Helm, Jr. |
| 2013/0211325 A1 | 8/2013 | Wang et al. |
| 2013/0226144 A1 | 8/2013 | Milligan |
| 2013/0231630 A1 | 9/2013 | Krause et al. |
| 2013/0261554 A1 | 10/2013 | Baid |
| 2013/0296808 A1 | 11/2013 | Triplett et al. |
| 2014/0012196 A1 | 1/2014 | Zivkovic et al. |
| 2014/0012206 A1 | 1/2014 | Shaw et al. |
| 2014/0025036 A1 | 1/2014 | Bierman et al. |
| 2014/0039399 A1 | 2/2014 | Burkholz |
| 2014/0052065 A1 | 2/2014 | Woehr et al. |
| 2014/0058329 A1 | 2/2014 | Walker et al. |
| 2014/0058357 A1 | 2/2014 | Keyser et al. |
| 2014/0074032 A1 | 3/2014 | Bornhoft |
| 2014/0081210 A1 | 3/2014 | Bierman et al. |
| 2014/0100528 A1 | 4/2014 | Finnestad et al. |
| 2014/0107619 A1 | 4/2014 | Butts et al. |
| 2014/0135702 A1 | 5/2014 | Woehr et al. |
| 2014/0135703 A1 | 5/2014 | Yeh et al. |
| 2014/0163470 A1 | 6/2014 | Baid |
| 2014/0163523 A1 | 6/2014 | Constantineau et al. |
| 2014/0171876 A1 | 6/2014 | Shaw et al. |
| 2014/0174578 A1 | 6/2014 | Bonnal et al. |
| 2014/0180212 A1 | 6/2014 | Baid |
| 2014/0180219 A1 | 6/2014 | Ho et al. |
| 2014/0180250 A1 | 6/2014 | Belson |
| 2014/0180258 A1 | 6/2014 | Ho et al. |
| 2014/0188003 A1 | 7/2014 | Belson |
| 2014/0209197 A1 | 7/2014 | Carrez et al. |
| 2014/0221931 A1 | 8/2014 | Kuracina et al. |
| 2014/0257202 A1 | 9/2014 | Woehr |
| 2014/0261860 A1 | 9/2014 | Heath et al. |
| 2014/0276453 A1 | 9/2014 | Woehr |
| 2014/0276455 A1 | 9/2014 | Yeh et al. |
| 2014/0276458 A1 | 9/2014 | Mansour et al. |
| 2014/0276459 A1 | 9/2014 | Yeh et al. |
| 2014/0276462 A1 | 9/2014 | Vincent et al. |
| 2014/0276463 A1 | 9/2014 | Mansour et al. |
| 2014/0276466 A1 | 9/2014 | Yeh et al. |

(56) References Cited

U.S. PATENT DOCUMENTS

| | | |
|---|---|---|
| 2014/0296794 A1 | 10/2014 | Li |
| 2014/0296829 A1 | 10/2014 | White et al. |
| 2014/0303561 A1 | 10/2014 | Li |
| 2014/0316350 A1 | 10/2014 | Yamaguchi et al. |
| 2014/0323980 A1 | 10/2014 | Cronenberg et al. |
| 2014/0336582 A1 | 11/2014 | Tisci et al. |
| 2014/0336583 A1 | 11/2014 | Morrissey et al. |
| 2014/0358033 A1 | 12/2014 | Lynn |
| 2014/0364809 A1 | 12/2014 | Isaacson et al. |
| 2014/0371686 A1 | 12/2014 | Sano et al. |
| 2015/0005718 A1 | 1/2015 | Walker et al. |
| 2015/0038943 A1 | 2/2015 | Warring et al. |
| 2015/0045746 A1 | 2/2015 | Macy, Jr. et al. |
| 2015/0073304 A1 | 3/2015 | Miller |
| 2015/0080801 A1 | 3/2015 | Tanabe et al. |
| 2015/0148748 A1 | 5/2015 | Shluzas et al. |
| 2015/0148749 A1 | 5/2015 | Cohn |
| 2015/0148756 A1 | 5/2015 | Lynn |
| 2015/0151083 A1 | 6/2015 | White et al. |
| 2015/0157799 A1 | 6/2015 | Chen et al. |
| 2015/0157800 A1 | 6/2015 | Chen et al. |
| 2015/0157848 A1 | 6/2015 | Wu et al. |
| 2015/0165132 A1 | 6/2015 | Perot et al. |
| 2015/0174339 A1 | 6/2015 | Bokelman et al. |
| 2015/0174374 A1 | 6/2015 | Woehr |
| 2015/0190168 A1 | 7/2015 | Bierman et al. |
| 2015/0190627 A1 | 7/2015 | Ueda et al. |
| 2015/0196737 A1 | 7/2015 | Baid |
| 2015/0196749 A1 | 7/2015 | Ziv et al. |
| 2015/0196750 A1 | 7/2015 | Ueda et al. |
| 2015/0202424 A1 | 7/2015 | Harton |
| 2015/0209508 A1 | 7/2015 | Constantineu et al. |
| 2015/0258325 A1 | 9/2015 | Panian et al. |
| 2015/0265829 A1 | 9/2015 | Truitt et al. |
| 2015/0290431 A1 | 10/2015 | Hall et al. |
| 2015/0297817 A1 | 10/2015 | Guala |
| 2015/0297880 A1 | 10/2015 | Ogawa et al. |
| 2015/0313523 A1 | 11/2015 | Chelak et al. |
| 2015/0328438 A1 | 11/2015 | Baid |
| 2015/0352331 A1 | 12/2015 | Helm, Jr. |
| 2015/0352333 A1 | 12/2015 | Arellano Cabrera et al. |
| 2016/0000364 A1 | 1/2016 | Mendels et al. |
| 2016/0001057 A1 | 1/2016 | Lopez et al. |
| 2016/0015943 A1 | 1/2016 | Belson et al. |
| 2016/0015945 A1 | 1/2016 | Warring et al. |
| 2016/0015958 A1 | 1/2016 | Ueda et al. |
| 2016/0015961 A1 | 1/2016 | Mansour et al. |
| 2016/0022963 A1 | 1/2016 | Belson |
| 2016/0022977 A1 | 1/2016 | Ueda et al. |
| 2016/0022978 A1 | 1/2016 | Ueda |
| 2016/0030730 A1 | 2/2016 | Mosler et al. |
| 2016/0038730 A1 | 2/2016 | Zollinger |
| 2016/0088995 A1 | 3/2016 | Ueda et al. |
| 2016/0114136 A1 | 4/2016 | Woeher |
| 2016/0114137 A1 | 4/2016 | Woehr et al. |
| 2016/0114147 A1 | 4/2016 | Siopes et al. |
| 2016/0121082 A1 | 5/2016 | Emmert et al. |
| 2016/0129180 A1 | 5/2016 | Roman et al. |
| 2016/0135841 A1 | 5/2016 | Albert et al. |
| 2016/0136051 A1 | 5/2016 | Lavi |
| 2016/0158498 A1 | 6/2016 | White et al. |
| 2016/0158499 A1 | 6/2016 | Helm |
| 2016/0158524 A1 | 6/2016 | Quach et al. |
| 2016/0183976 A1 | 6/2016 | Bertoli et al. |
| 2016/0199575 A1 | 7/2016 | Belley et al. |
| 2016/0206813 A1 | 7/2016 | Abe et al. |
| 2016/0206858 A1 | 7/2016 | Ishida |
| 2016/0220270 A1 | 8/2016 | Tamura et al. |
| 2016/0235944 A1 | 8/2016 | Ma |
| 2016/0235949 A1 | 8/2016 | Baid |
| 2016/0235961 A1 | 8/2016 | Maffei |
| 2016/0256667 A1 | 9/2016 | Ribelin et al. |
| 2016/0263353 A1 | 9/2016 | Kuracina et al. |
| 2016/0271370 A1 | 9/2016 | Keyser et al. |
| 2016/0296724 A1 | 10/2016 | Goral et al. |
| 2016/0325078 A1 | 11/2016 | Burkholz |
| 2017/0000983 A1 | 1/2017 | Woehr |
| 2017/0182293 A1 | 6/2017 | Chhikara |
| 2017/0239443 A1 | 8/2017 | Abitabilo et al. |
| 2018/0154119 A1 | 6/2018 | White |
| 2019/0091448 A1 | 3/2019 | Chhikara |

FOREIGN PATENT DOCUMENTS

| | | |
|---|---|---|
| EP | 0 821 980 | 4/2003 |
| EP | 1 323 442 | 7/2003 |
| JP | 56-130161 | 10/1981 |
| JP | H06-78999 A | 3/1994 |
| JP | 10-015075 | 1/1998 |
| JP | 2901915 B2 | 6/1999 |
| JP | 2005-261931 | 9/2005 |
| JP | 2008-528225 A | 7/2008 |
| JP | 4211858 B2 | 1/2009 |
| WO | WO 1990/01351 | 2/1990 |
| WO | WO 1997/015342 | 5/1997 |
| WO | WO 2006/082350 | 8/2006 |
| WO | WO 2006/090148 | 8/2006 |
| WO | WO 2007/008511 | 1/2007 |
| WO | WO 2007/052656 | 5/2007 |
| WO | WO 2007/143555 | 12/2007 |
| WO | WO 2008/042285 | 4/2008 |
| WO | WO 2009/032008 | 3/2009 |
| WO | WO 2009/092076 | 7/2009 |
| WO | WO 2011/146764 | 11/2011 |
| WO | WO 2011/146769 | 11/2011 |
| WO | WO 2015/119940 | 8/2015 |
| WO | WO 2018/009653 | 1/2018 |

OTHER PUBLICATIONS

U.S. Appl. No. 15/951,509, filed Apr. 12, 2018, White et al.
BD Nexvia Closed IV Catheter System, http://www.bd.com/infusion/products/ivcatheters/nexiva/index.asp, downloaded Sep. 6, 2013 in 19 pages.
International Preliminary Report on Patentability, re PCT Application No. PCT/US2011/037242, dated Nov. 20, 2012.
International Search Report and Written Opinion, re PCT Application No. PCT/US2011/037242, dated Nov. 2, 2011.

* cited by examiner

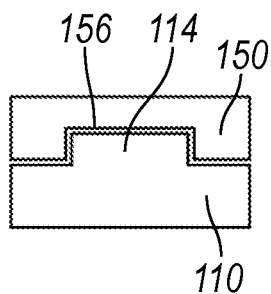 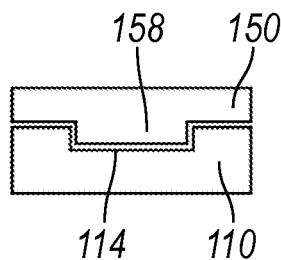 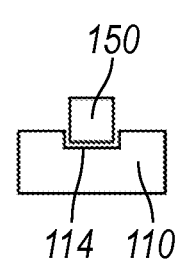 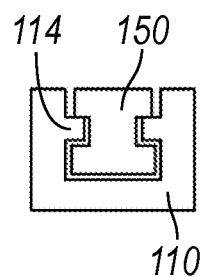
FIG. 3A    FIG. 3B    FIG. 3C    FIG. 3D
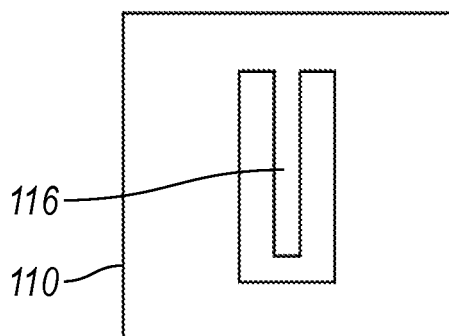
FIG. 4
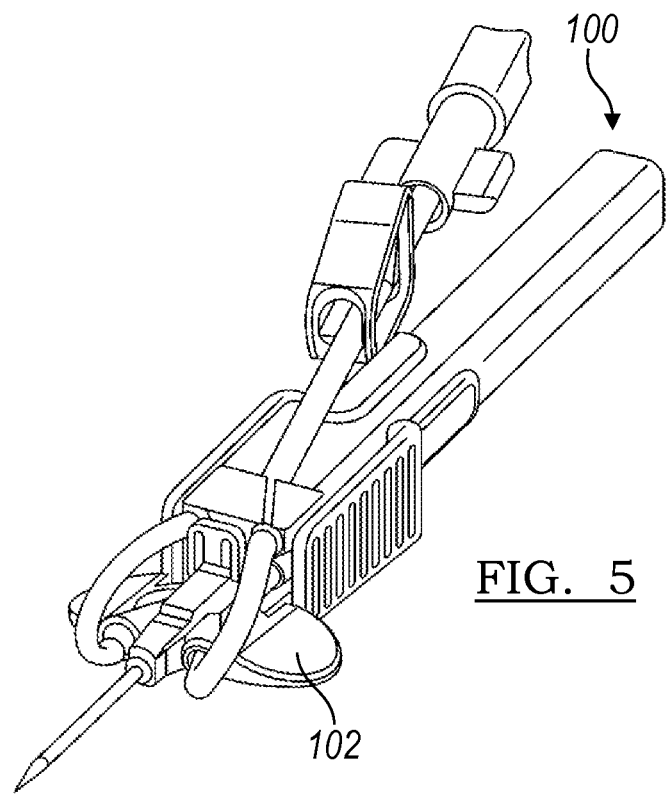
FIG. 5
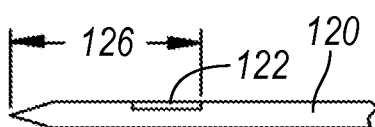 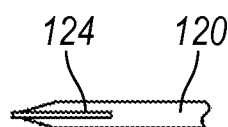 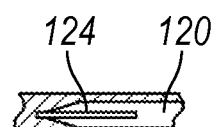
FIG. 6A    FIG. 6B    FIG. 6C

DETAIL A

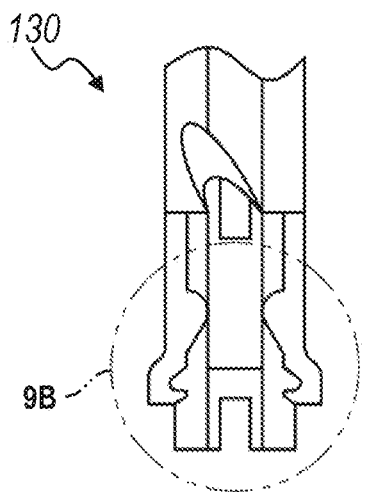
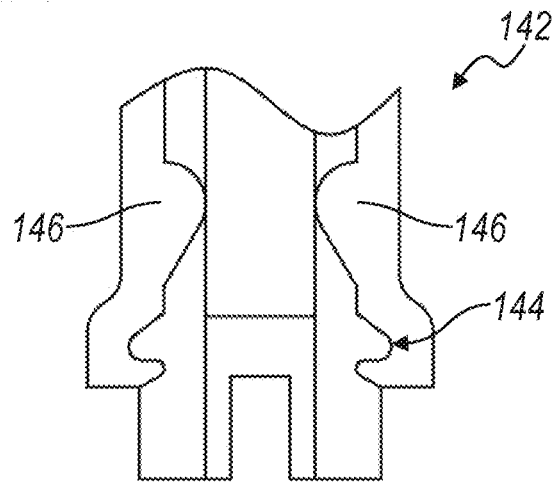
FIG. 9A  FIG. 9B
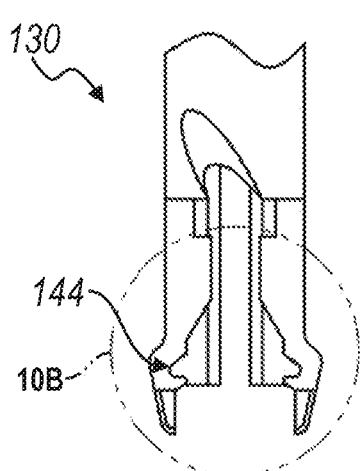
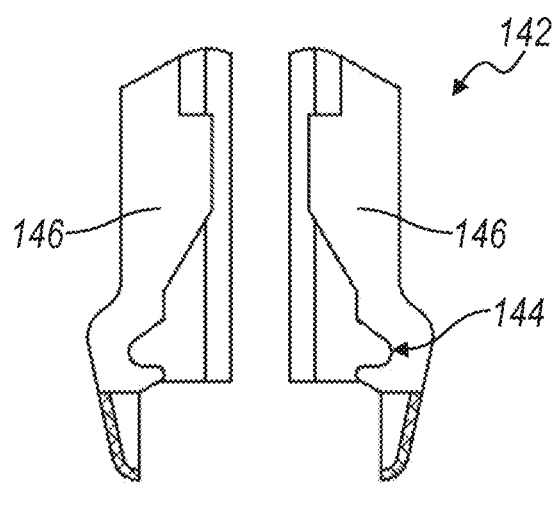
FIG. 10A  FIG. 10B
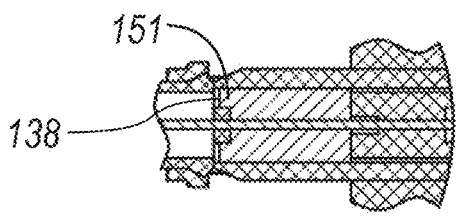
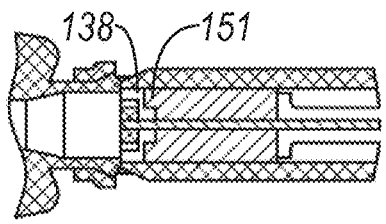
FIG. 11A  FIG. 11B
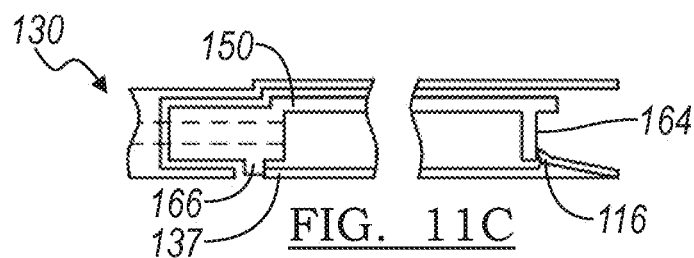
FIG. 11C

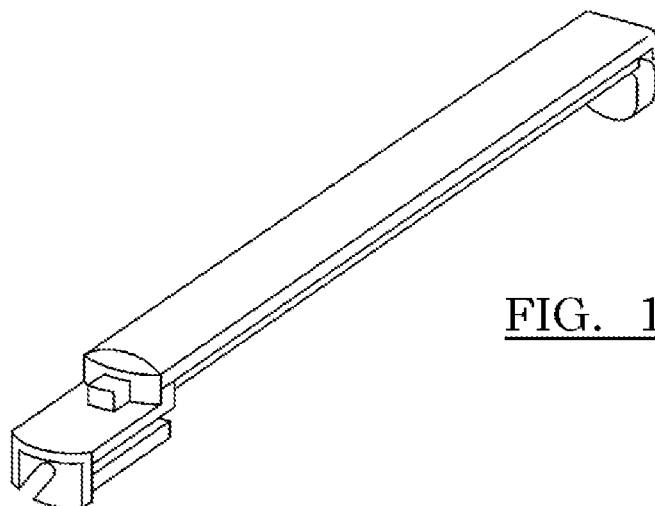
FIG. 13A
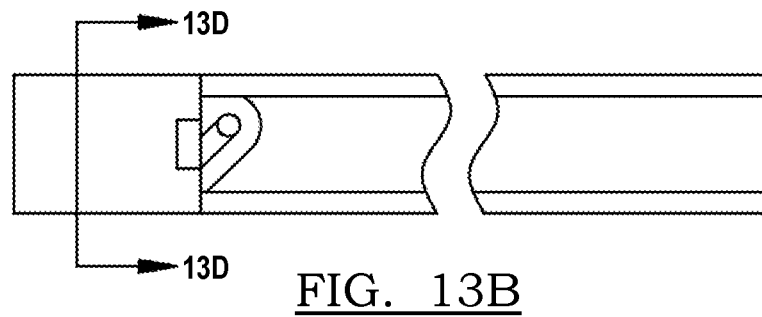
FIG. 13B
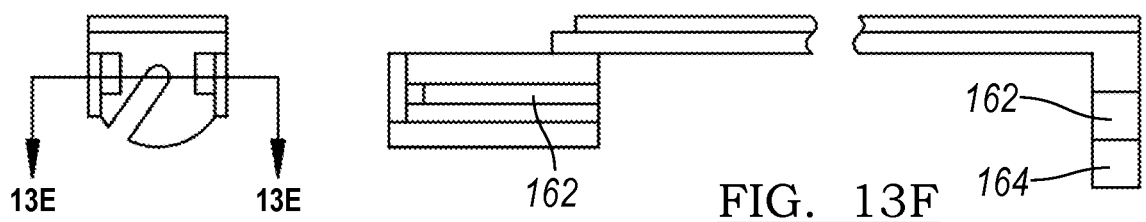
FIG. 13C
FIG. 13F
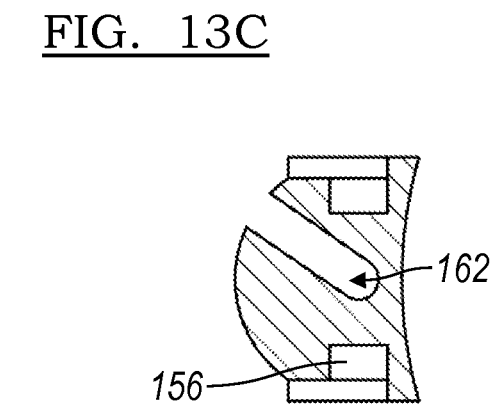
FIG. 13D
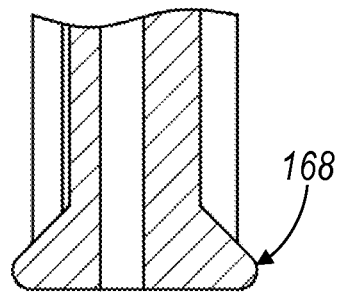
FIG. 13E

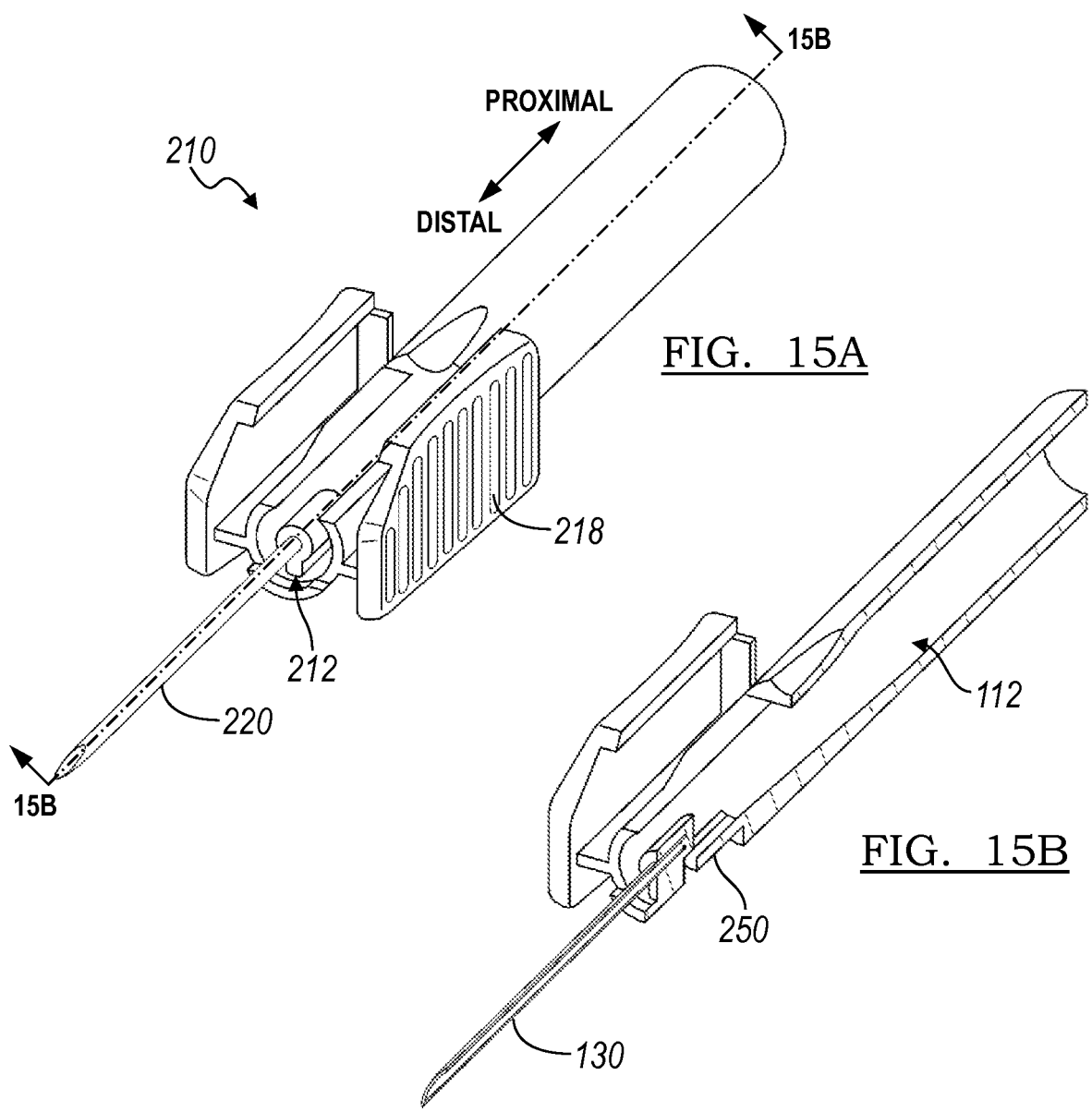
FIG. 15A
FIG. 15B
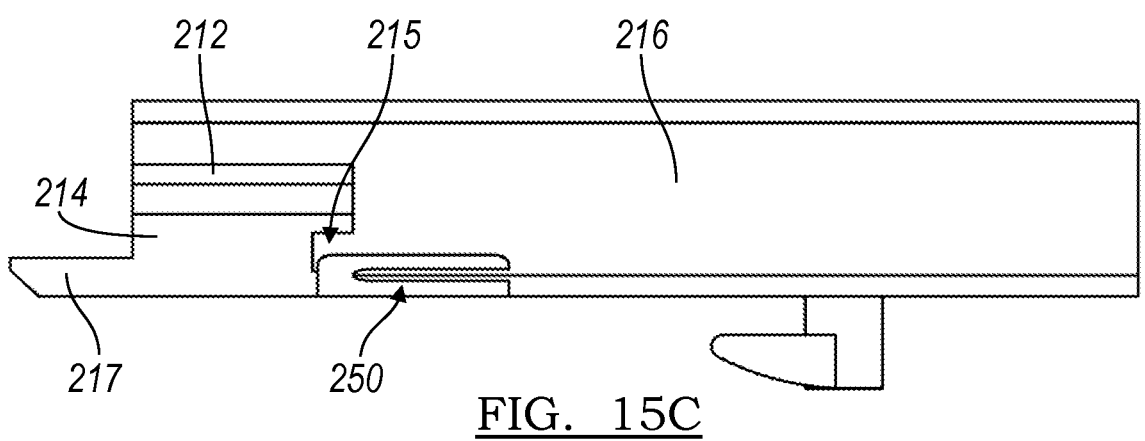
FIG. 15C

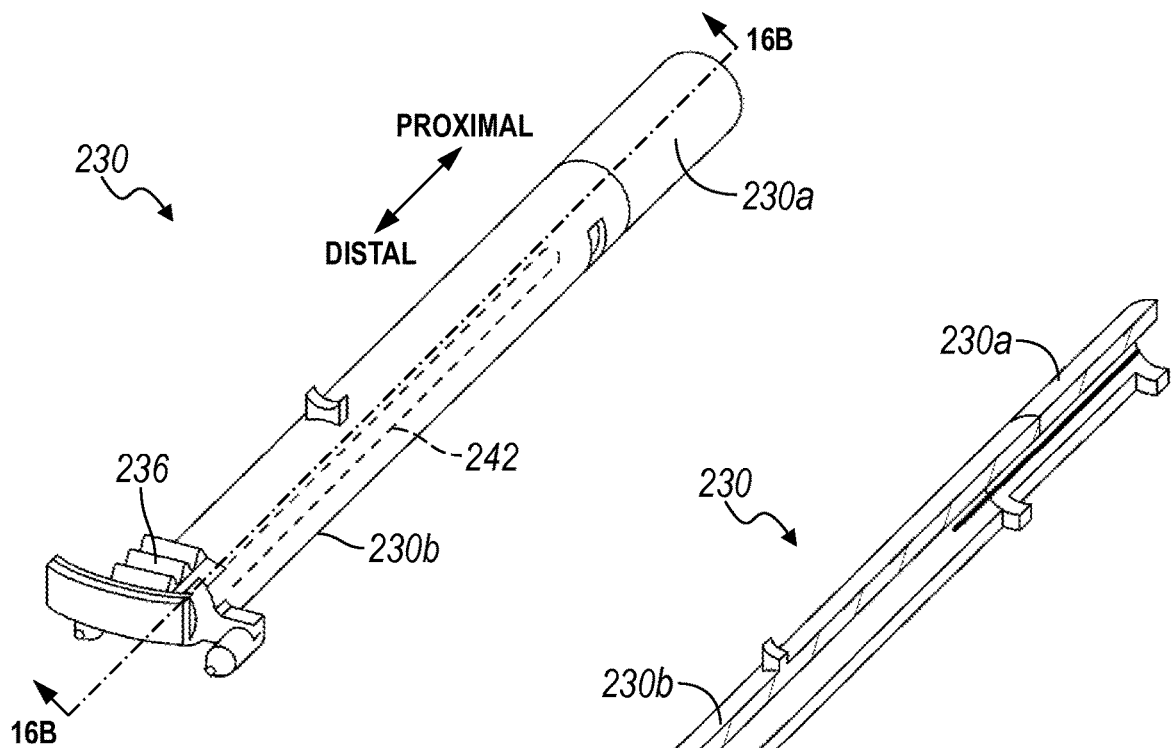
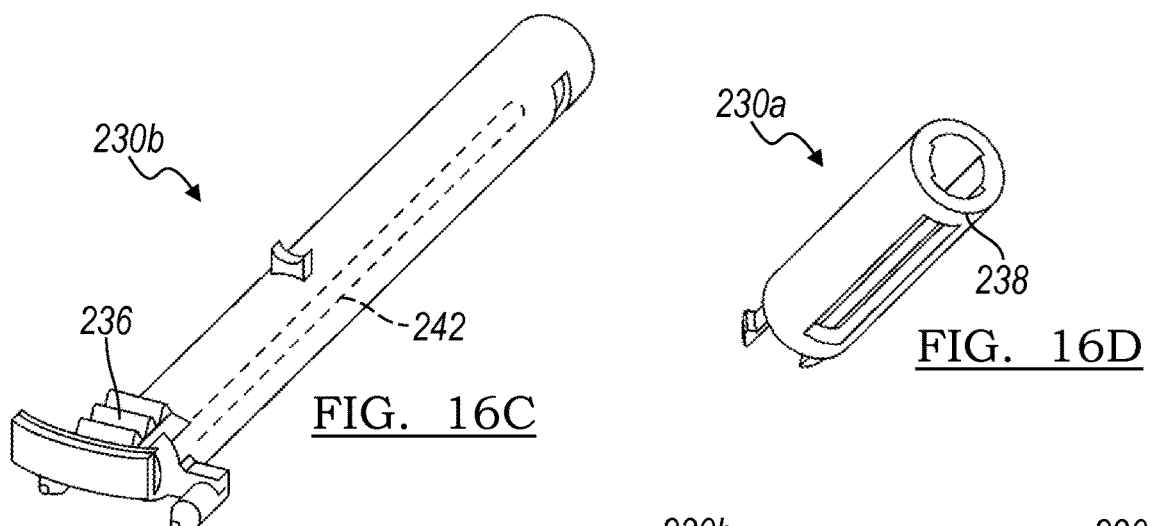
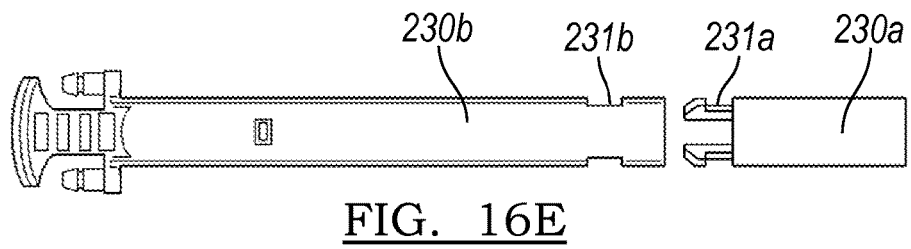

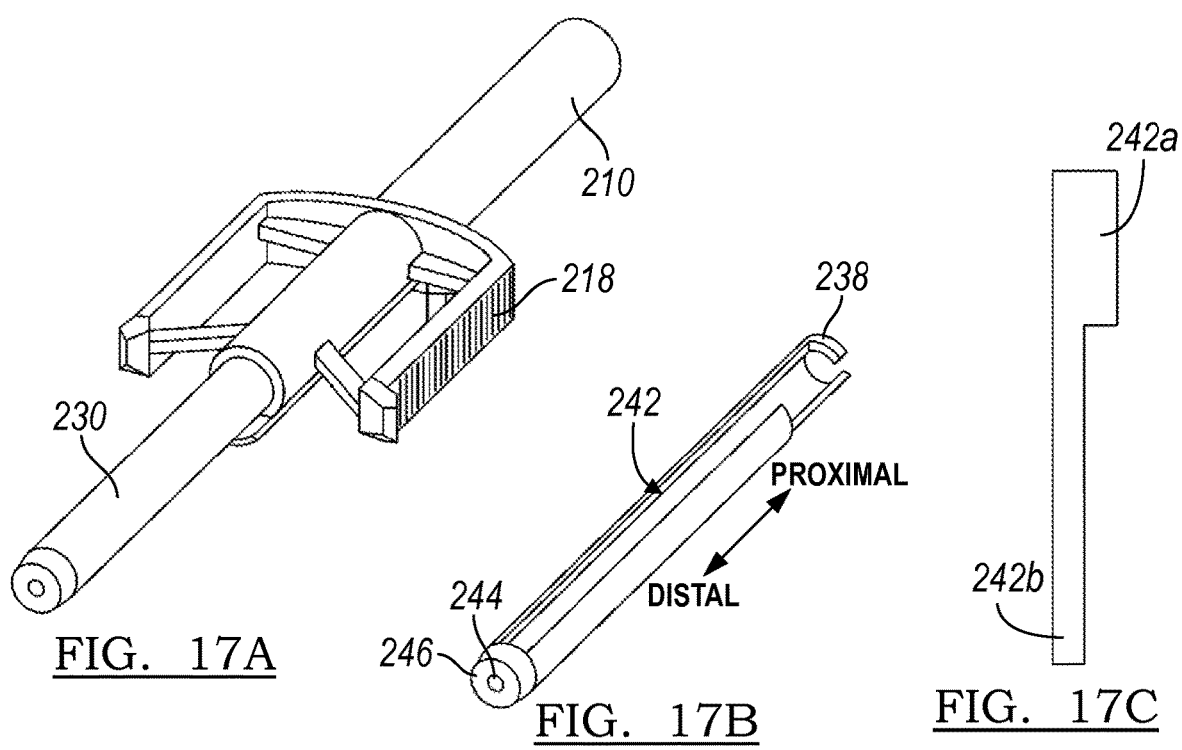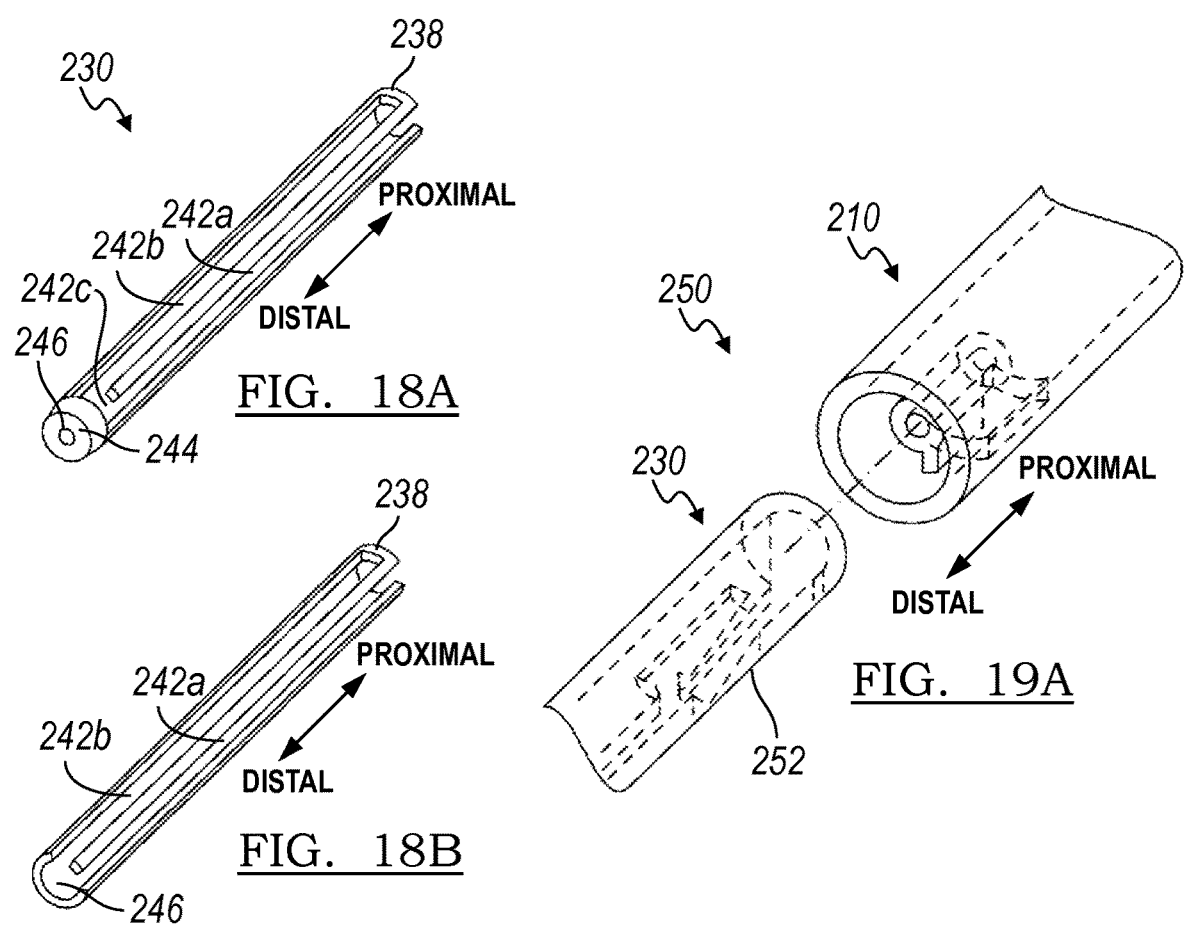

SAFETY NEEDLE SYSTEM OPERABLE WITH A MEDICAL DEVICE

CROSS-REFERENCE TO RELATED APPLICATIONS

This application is a continuation of U.S. patent application Ser. No. 14/299,872, filed 9 Jun. 2014, now issued as U.S. Pat. No. 10,159,818, which is a continuation of U.S. patent application Ser. No. 13/111,716, filed 19 May 2011, now issued as U.S. Pat. No. 8,814,833 which claims the benefit of U.S. Provisional Applications Nos. 61/352,220 filed 7 Jun. 2010, 61/407,777 filed 28 Oct. 2010, 61/448,132 filed 1 Mar. 2011, 61/346,292 filed 19 May 2010, 61/407,797 filed 28 Oct. 2010, 61/418,354 filed 30 Nov. 2010, 61/438,781 filed 2 Feb. 2011, and 61/442,456 filed 14 Feb. 2011, the entirety of all of which is incorporated in their entirety by this reference.

TECHNICAL FIELD

This invention relates generally to the medical field, and more specifically to an improved safety needle system in the medical field.

BACKGROUND

Many medical devices, such as catheter systems for establishing intravenous therapy, include needles that are inserted into patients. By contacting body tissue and fluids such as blood, such needles carry biohazard risks including cross-contamination and transmission of blood-borne diseases, as well as accidental needle sticks or punctures inflicted on a user of the medical device or any other handlers of used medical instruments. Thus, there is a need in the medical field to create an improved safety needle system. This invention provides such an improved safety needle system operable with a medical device.

BRIEF DESCRIPTION OF THE FIGURES

FIGS. 3A-3D are schematics of variations of interactions between the housing and the slider in the safety needle system of a first preferred embodiment;

FIG. 4 is an "unwrapped" illustration of the housing stop in the safety needle system of a first preferred embodiment;

FIG. 5 is an example of the safety needle system in use with a medical device;

FIGS. 6A-6C are variations of the needle in the safety needle system of a preferred embodiment;

FIGS. 9A-9B and 10A-10B are schematics of variations of the sheath in the safety needle system of a first preferred embodiment;

FIGS. 11A-11C are schematics of the coupling between the sheath, slider, and housing during use of the safety needle system of the first preferred embodiment;

FIGS. 13A-13F are schematics of a variation of the slider in the safety needle system of a first preferred embodiment;

FIGS. 15A-15C are schematics of a perspective view, cross-sectional perspective view, and cross-sectional side view, respectively, or the housing in the safety needle system of a second preferred embodiment;

FIGS. 16A-18B are schematics of variations of the sheath in the safety needle system of a second preferred embodiment;

DESCRIPTION OF THE PREFERRED EMBODIMENTS

Figure 1A:
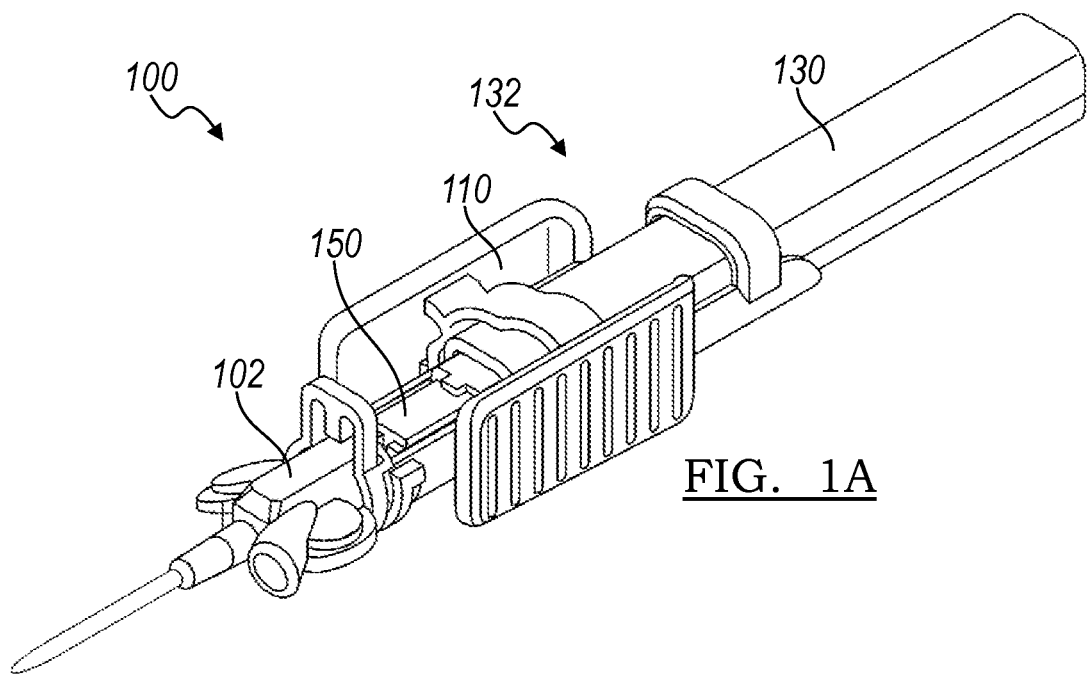
FIGS. 1A and 1B are schematics of the safety needle system of a first preferred embodiment with the sheath in the retracted position and in the extended position, respectively.

The following description of preferred embodiments of the invention is not intended to limit the invention to these preferred embodiments, but rather to enable any person skilled in the art to make and use this invention.

The safety needle system is preferably used with a catheter with a catheter hub, such as an intravenous catheter. In one embodiment, the safety needle system is operated with a vascular delivery system such as that described in U.S. patent application Ser. Nos. 12/855,013 and 13/111,693, which are each hereby incorporated in its entirety by this reference. In particular, the safety needle system may be operable with a vascular delivery system adapted to be placed about a catheter insertion site on a patient, in which the vascular delivery system includes a frame with a catheter hub providing a first anchoring point on the patient, a stabilization hub providing a second anchoring point on the patient, and at least one lateral member extending between the catheter hub and the stabilization hub, such that the first and second anchoring points are distributed around the insertion site to anchor the frame to the patient and stabilize the catheter. The frame preferably operates in a folded configuration in which the catheter and stabilization hubs may be coupled, and in an unfolded configuration in which the first and second anchoring points are distributed around the insertion site to anchor the frame to the patient, thereby stabilizing the catheter. For instance, in a preferred embodiment the first and second anchoring points are on opposite sides of the insertion site, such as proximal and distal to the side, or on opposite lateral sides of the insertion site. In alternative embodiments of the frame, the frame may include any suitable number of hubs and any suitable number of lateral members, such that the frame forms an enclosed or partial, non-enclosed perimeter of any suitable shape and size around the insertion site. Each lateral member may be flexible, such as to allow the catheter and stabilization hubs to move relative to one another with a significant number of degrees of freedom, including displacement in the compression direction (and subsequent displacement in the tension direction) along the axis of the catheter, displacement in both directions along the other two axes, twisting in both directions along the axis of the catheter, and bending in both directions along the other two axes. In particular, the lateral member may be reversibly bendable to allow the frame to be in a folded configuration in which the catheter and stabilization hubs are coupleable. However, the safety needle system may alternatively be used with any other suitable kind of catheter, a syringe, or other medical needle devices or devices used with a medical needle. Use of the safety needle system with such medical devices may reduce risk of cross-contamination and infection from bodily fluids and other biohazards, and reduce risk of accidental needle injuries to a user handling the medical device.

Safety Needle System of a First Embodiment

Figure 1B:
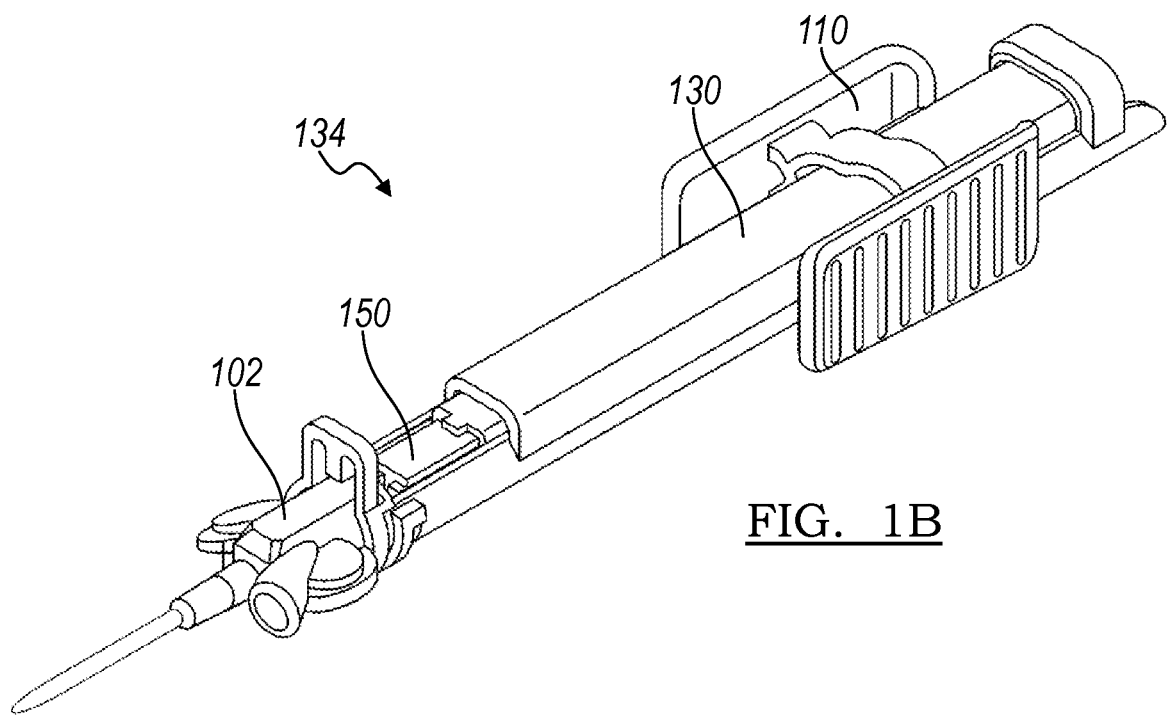

In a first preferred embodiment, as shown in FIGS. 1 and 2, the safety needle system 100 operable with a medical device 102 includes: a housing 110 having a needle mount 112; a needle 120 having a distal end insertable through the medical device 102 and a proximal end coupled to the needle mount 112; a sheath 130 telescopically engaged with the housing 110 and circumferentially surrounding at least a portion of the needle 120, in which the sheath 130 operates in a retracted position 132 and an extended position 134; and a slider 150 longitudinally engaged with the sheath and/or housing and including a restraint that selectively engages with the sheath. In the retracted position 132 of the sheath, the sheath exposes the distal end of the needle. In the extended position 134 of the sheath, the sheath substantially surrounds the distal end of the needle. The sheath is coupleable to the medical device such that removal of the needle from the medical device draws the sheath over the needle, thereby transitioning the sheath from the retracted position to the extended position. In a preferred embodiment, the restraint is selectively engaged with the sheath such that (1) the restraint is coupled to the sheath when the sheath is in the retracted position and coupled to the medical device, and the restraint reinforces the coupling of the sheath to the medical device, and (2) the restraint is uncoupled from the sheath when the sheath is in the extended position, and the restraint weakens the coupling of the sheath to the medical device, thereby reducing the force required to uncouple the sheath from the medial device. In other variations, during removal of the needle from the medical device as the sheath is drawn over the needle, the slider automatically triggers the full uncoupling of the sheath and the medical device. Removal of the needle is preferably performed by pulling the needle away from the medical device, but alternatively removal of the needle may be performed by pulling the medical device away from the needle. In other words, to draw the sheath from its retracted position to its extended position and to decouple the safety needle system from the medical device, the user (e.g., medical practitioner) may pull the needle away in a proximal direction (or pull the medical device away in a distal direction away from the safety needle system) thereby allowing the sheath to slide from its retracted position to its extended position to cover the distal end of the needle. In a preferred embodiment, the slider further includes a proximal articulation and a distal articulation, When the sheath is in the extended position the proximal articulation is coupled to the housing and the distal articulation is coupled to the sheath, thereby locking the sheath in the extended position; however, the system may include any suitable locking mechanism to lock the sheath in the extended position.

Figure 2A:
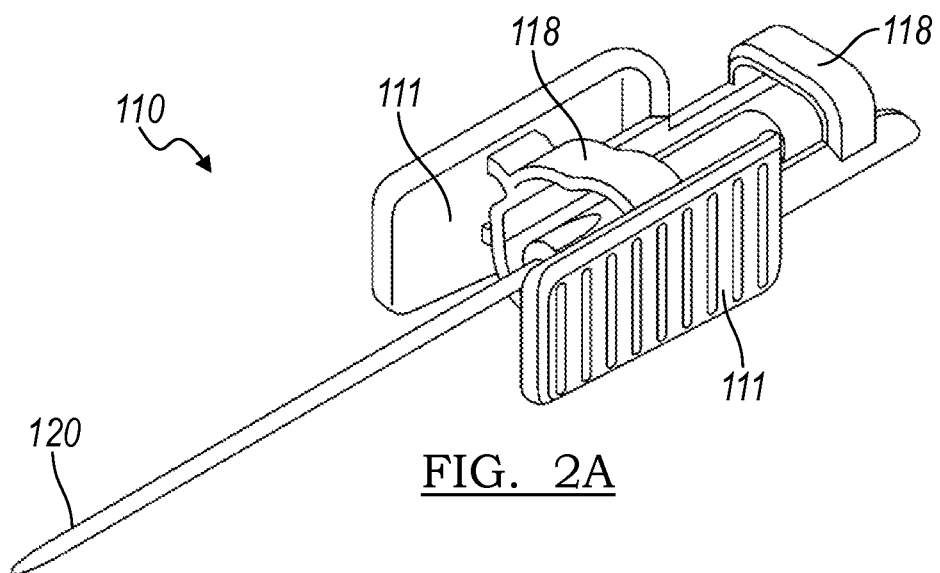
FIGS. 2A-2C are schematics of the housing in the safety needle system of a first preferred embodiment.
Figure 2B:
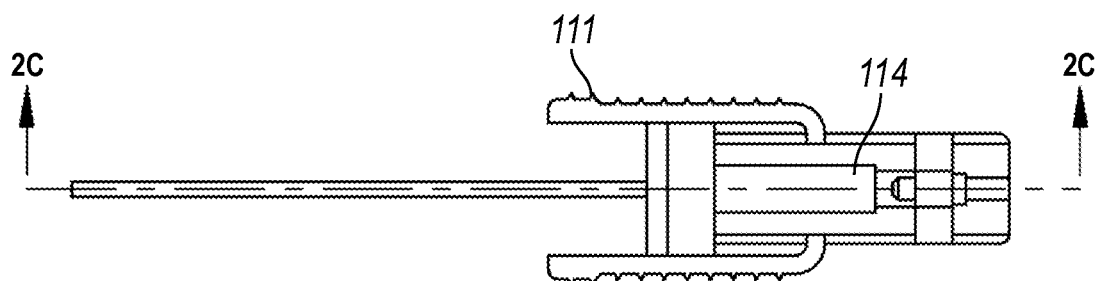
Figure 2C:
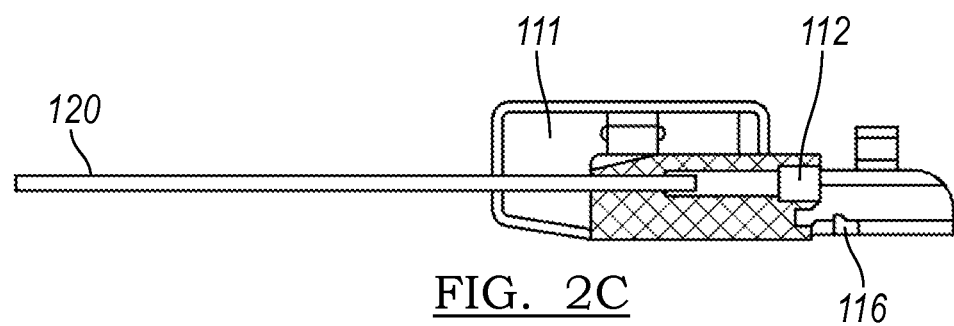

The housing 110 functions to support the sheath 130 and the slider 150, to support the needle and/or to provide a user interface. As shown in FIGS. 2A-2C, the housing 110 includes a needle mount 112 to which the needle is coupled. The needle mount is preferably on a distal end of the housing and axially centered on the housing, but may alternatively be on any suitable portion of the housing. The needle may be molded into the needle mount such that the distal end of the needle extends out of the distal end of the housing, but the needle may alternatively be coupled to the needle mount with a snap fit, friction fit, threads, epoxy, or in any suitable manner.

The housing 110 is slidingly or telescopically engaged with the sheath 130 and/or slider 150. The housing no includes an inner portion that is contained within the sheath, such that the housing slides within the sheath. However, alternatively the housing may be tubular or otherwise configured such that the sheath slides within the housing. The inner portion of the housing may include a track 114 along which the slider 150 is slidingly engaged. The track is preferably longitudinal along the housing body, and may be a projected track such as a ridge (FIGS. 3A and 3D), and/or a recessed track (FIGS. 3B-3D). In one variation, as shown in FIG. 3A, the housing includes one or more arches 118 that form an outer framework around the sheath and/or slider, such as brackets.

The housing 110 preferably includes a housing stop 116 that is configured to abut the proximal articulation of the slider 150 when the sheath is in the extended position. In a preferred embodiment, the abutment of the housing stop 116 against the proximal articulation 164 (or other portion of the slider) functions to fix the relative positions of the housing and slider, thereby contributing to locking the sheath in the extended position. In one variation, as best shown in FIGS. 2C and 4, the housing stop 116 includes a snap lock cantilevered arm whose free end abuts the proximal articulation of the slider. The housing stop 116 may be biased or radially deflected towards the slider such as to allow the slider to pass the housing stop in one direction (e.g. as the slider passes in a distal direction relative to the housing) but to prevent the slider from passing the housing stop in the opposite direction (e.g. as the slider passes in a proximal direction relative to the housing). Alternatively, other housing stop may include a sliding latch, lever, push button, another protrusion of the housing that interacts with the slider, or another suitable mechanism that abuts any suitable portion of the slider. As another alternative, the housing stop may include an aperture that receives the proximal articulation or any suitable portion of the slider. The housing stop is preferably integrally formed with the housing, but may alternatively be a separate piece coupled to the housing during assembly of the safety needle device.

In some embodiments, as best shown in FIG. 1, the housing 110 may have one or more handles 111 that a user can grip and manipulate to operate the safety needle system. The handle 111 preferably includes two side grips on opposite sides of the housing that enable secure grasping with one hand. The handle 111 may include features such as ergonomic contours, ridges to improve friction in the grip, cushioning material such as silicone, or any suitable additions. Furthermore, other variations of the handle may include fewer or more grips (such as a single bulbous handle), and may be particular for specific applications. In some embodiments, as shown in FIG. 5, the handle may further function as a hub cradle, such as for receiving a catheter hub or stabilization hub such as that described in U.S. patent application Ser. No. 12/855,013, or any suitable hub or other portion of a medical device.

The housing 110 is preferably plastic and may be made of one singular piece, such as by an injection molding that forms the needle mount, arches, and/or handles integrally with the rest of the housing. The housing may alternatively include multiple pieces that are separately manufactured and attached to the tubular portion of the housing in a secondary process such as with adhesive, locking joints, or other fasteners. However, the housing may be in made in any suitable manufacturing process such as milling, turning, or stereolithography, and be made of any suitable material.

The needle 120 of the safety needle system is preferably a medical grade needle with a cannula, such as those used to aid insertion of catheters. The needle may have a gauge or size that is selected from a group of available needle gauges, such as standard diameter sizes. In one variation, as shown in FIG. 6A, the needle 120 may include a notch 122 along a portion of the length of the needle. The notch 122 is positioned at a notch extent distance 126 defined as the distance between the distal end of the needle and the proximal edge of the notch. In an exemplary embodiment used with a catheter, during catheter placement within a blood vessel, the needle 120 is typically telescopically engaged within the catheter, forming an annular space between the outer wall of the needle and inner wall of the catheter. When the needle is placed within the blood vessel, blood or other fluids pass along the length of the needle, and the notch in the needle allows a small amount of the fluid (known as "flash") to pass into the annular space between the needle and catheter. This "flash" becomes visible to the user through the catheter, and the appearance of the flash signifies needle placement within the blood vessel.

In another variation of the needle 120, as shown in FIG. 6B, the needle may be a substantially solid needle rather than a hollow needle with a cannula. For example, the needle 120 may include a trocar as a catheter introducer. In this variation, the needle may include a sharp distal tip and a groove running from the distal tip of the needle. The groove 124 preferably receives the flash upon needle insertion into the vessel (FIG. 6C), and the flash may be visible to the user through the catheter tubing and/or catheter hub.

The sheath 130 of the safety needle system preferably functions to cover the distal end of the needle 120 after the needle tip is no longer needed, to help protect the user from fluid contamination and accidental needle punctures. The sheath 130 operates in a retracted position 132 and an extended position 134, such that in the retracted position 132 the sheath exposes the distal end of the needle 120, and in the extended position 134 the sheath is extended from the housing and substantially surrounds or covers the distal end of the needle 120. In the extended position, the sheath may cover the entire needle body, or only a portion of the needle body including the distal end.

Figure 7A:
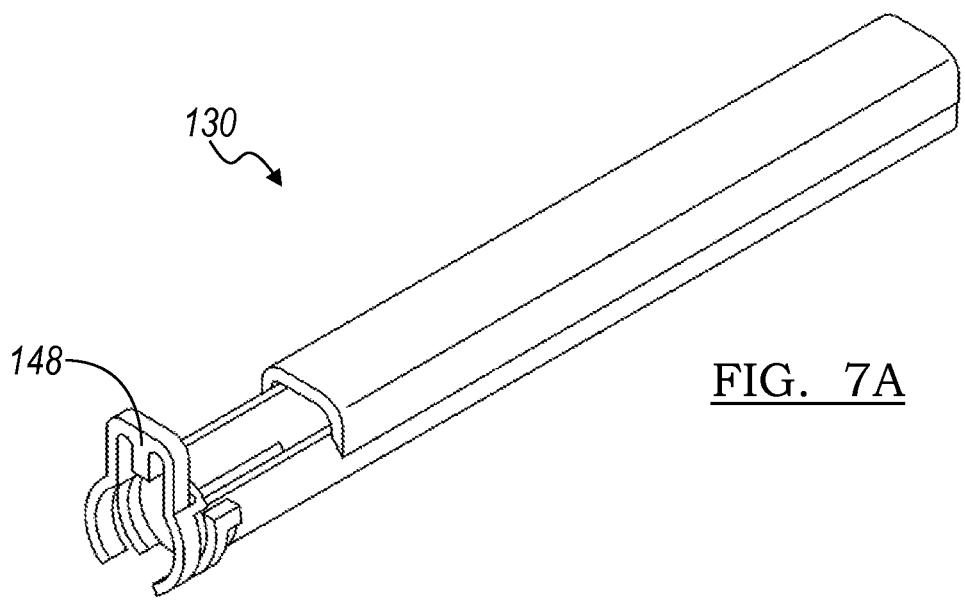
FIGS. 7A-7F are schematics of the sheath in the safety needle system of a first preferred embodiment.
Figure 7B:
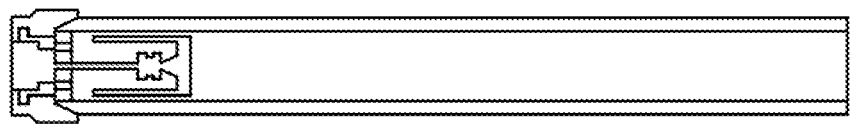
Figures 7C, 7D:
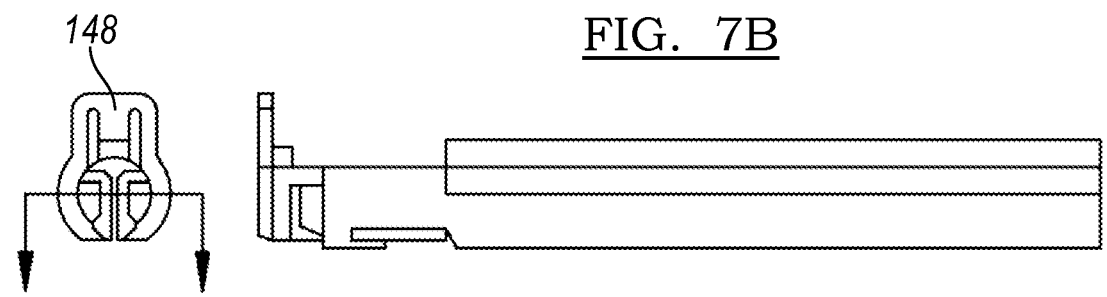
Figures 7E, 7F:
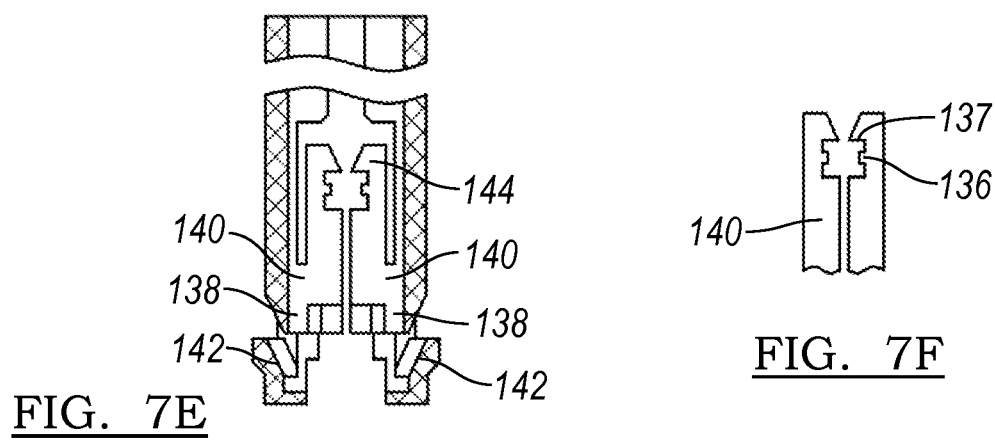

As best shown in FIG. 7F, the sheath 130 preferably includes a set of sheath stops including a first stop 136 and a second stop 137. The first stop 136 is configured to abut the distal articulation of the slider 150 when the restraint 151 is engaged with the split portion 140 of the sheath. The second stop 137 is configured to abut the distal articulation of the slider 150 when the sheath is in the extended position which prevents substantial relative longitudinal motion of the sheath and housing, thereby contributing to locking the sheath in the extended position. The sheath stops may additionally and/or alternatively abut against any suitable part of the slider. In one variation the sheath stops 136 and 137 may include an aperture defined in a side wall of the sheath. The aperture may have a partial perimeter defined by the gap between two or more split portions 140 in a side wall of the sheath. For example, the split portions 140 may be opposing members with each member having an angled or toothed tip 142. The opposing angled tips 142 define an aperture with a surface for abutting the distal articulation of the slider. Alternatively, the aperture may be a hole with an enclosed perimeter defined in the side wall of the sheath. In other variations, the sheath stops may include a projection or other extension, such as one similar to any of the variations of the housing stop, on any suitable portion of the sheath.

Figure 8F:
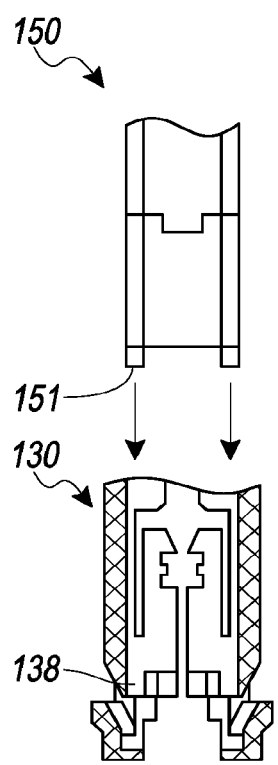
FIGS. 8A-8F are schematics of the slider in the safety needle system of a first preferred embodiment.
Figure 8A:
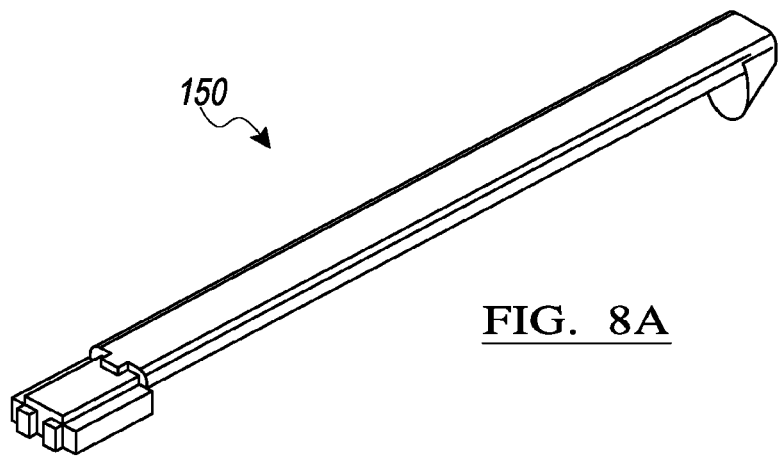
Figure 8C:
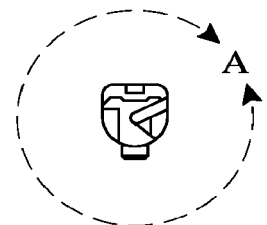
Figure 8B:
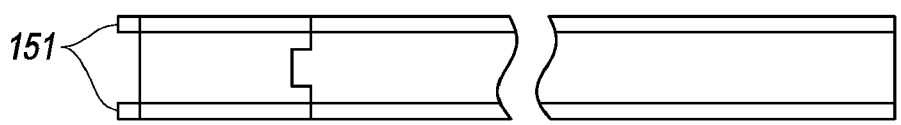

The sheath 130 may include a mating feature that enables the sheath to couple to the medical device. In one variation, the distal end of the sheath is adapted to mechanically couple to the medical device. In one preferred embodiment, as shown in FIGS. 7A-7E, the mating feature includes jaws 142 extending longitudinally from a distal end of the sheath 130. The jaws 142 are preferably flexible and couple to corresponding mating features (e.g., external articulations, cutouts or pockets) on the medical device 102. Each jaw may be coupled to a split portion 140 of the distal end of the sheath, and preferably couples to the restraint tab 151 of the slider. For example, as shown in FIG. 8F, each split portion or jaw may define a restraint slot 138 that receives a respective restraint tab 151 of the sheath. In one variation, the jaws may have an approximately arcuate profile (FIG. 7A) to conform to an approximately circular portion of the medical device. In other variations, the jaws may include hooked tips 144 (FIGS. 9A and 10B) and/or platforms 146 (FIGS. 10A and 10B) configured to particular corresponding features on the medical device 102 and/or slider 150. In other variations of mechanically coupling to the medical device, the sheath 130 may extend beyond the distal end of the housing when the sheath is in the retracted position to enable the distal end of the sheath to seat within a channel (e.g. a septum or other receptacle) of the medical device. For example, the medical device may retain the distal end of the sheath. As another example, the distal end of the sheath 130 may include extensions that mate with a corresponding recess in the medical device, or the medical device may include extensions that mate with a corresponding recess on the sheath 130. The distal end of the sheath 130 may include other features for sating within the septum or another receiving portion of the medical device, such as having a slight taper to a narrower diameter that fits within the septum, frictional features like ribs or ridges that may includes retention of the sheath 130 within the septum. The distal end of the sheath may additionally and/or alternatively couple to the medical device with magnets, adhesive, snap locks, fasteners, or any suitable mechanical means.

In another variation, the distal end of the sheath 130 is adapted to manually couple to the medical device 102. For example, as shown in FIG. 7A, the sheath may include a holding tab 148 extending from the distal end of the sheath that provides a finger rest for the user to press the holding tab against the medical device, thereby manually coupling the sheath and the medical device. The holding tab may extend laterally outwards or be a projection from the sheath extending in any suitable direction. The holding tab 148 may provide assistance for the user to hold the sheath against the medical device as a counterforce while pulling the housing and needle 120 away from the medical device. As shown in FIG. 7D, the holding tab 148 may include a bridge that connects the split portions of the sheath stop. Alternatively, the sheath may include multiple holding tabs, such as one holding tab 148 extending from each split portion 140 or jaw 142 of the sheath. The holding tab 148 may include features to help the user hold the holding tab against the medical device, such as a lip, ridges 236 (as shown by way of example in FIGS. 16A and 16C) that increase friction, or a friction coating such as silicone. The holding tab may include adhesive and/or a mechanical attachment such as a pin, snap or latch that couples the holding tab to the medical device.

Figure 8D:
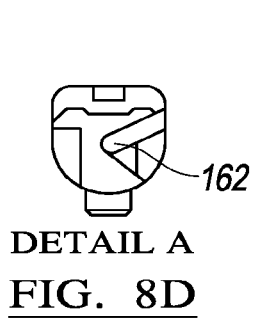

In a preferred embodiment, the slider 150 functions to selectively modulate the coupling force between the sheath and the medical device. The slider 150 may further contribute to locking the sheath 130 in the extended position over the distal end of the needle 120. The slider 150 longitudinally extends along at least a portion of the sheath 130 and/or housing and is slidingly engaged with the sheath and/or housing, such that the housing, sheath and slider are longitudinally movable relative to one another. The slider 150 may be directly coupled to the sheath, housing, needle, or any suitable portion of the system. As shown in FIGS. 8A-8E, the slider 150 may include a planar portion 152 and a sheath insert portion 143. The planar portion is preferably substantially flat and is slidingly engaged with the track of the housing, although may alternatively be contoured. The planar portion 152 may include a groove 156 (FIG. 3A) and/or a ridge 158 (FIG. 3B) complementary to the track 114 of the housing no, or any suitable profile. The sheath insert portion 154 is preferably located on a distal section of the slider, and is telescopically engaged in the sheath 130. As shown in FIG. 8D, the sheath insert portion may have an approximately arcuate cross-section profile, or any suitable profile complementary to the cross-sectional profile of the sheath to allow the sheath insert portion to be slidingly engaged with the sheath. The sheath insert portion 154 preferably defines an aperture 162 that allows the needle 120 to pass within the sheath insert. The aperture 162 may be a round hole, a slot, or any suitable opening to allow relative longitudinal translation of the slider 150 and the needle 120.

The sheath insert portion 154 preferably includes a restraint that selectively engages with the sheath, such that when the restraint is engaged with the sheath, the restraint reinforces the coupling of the sheath to the medical device, and when the restraint is disengaged from the sheath, the restraint weakens the coupling of the sheath to the medical device. In a preferred embodiment, as shown in FIG. 8F, the slider 150, in particular the sheath insert portion 154, may include at least one restraint tab 151 that is insertable into a restraint slot 138 on split portion 140 or jaw 142 of the sheath. In this embodiment, when the sheath is retracted and jaws 142 are surrounding and gripping the medical device, the restraint tabs 151 are coupled to the restraint slots 138 and the restraint tabs substantially prevent the jaws from moving relative to each other, thereby strengthening the grip of flexible jaws 142 on the medical device. When the sheath is extended (e.g. the housing is moved in a proximal direction away from the medical device), the restraint tabs become uncoupled from the restraint slots 138, leaving the flexible jaws 142 to more freely move relative to other, thereby weakening the grip of flexible jaws 142 on the medical device. In other words, the selective coupling of the restraint tabs 151 on the slider to the restraint slots 138 on the sheath effectively modulates the amount of force required to flex the jaws and uncouple the sheath from the medical device.

Figure 8E:
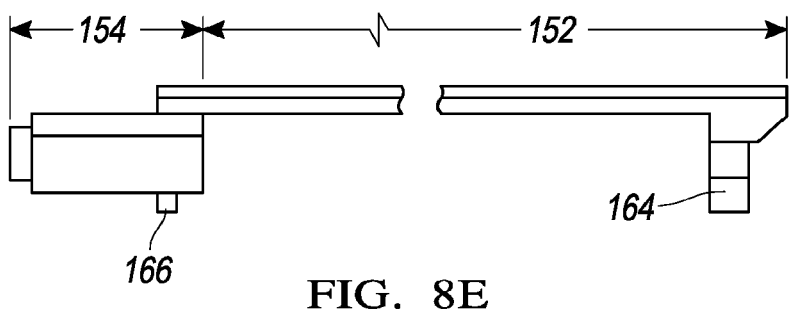

The slider 150 preferably includes a proximal articulation 164 that abuts the housing stop and/or a distal articulation 166 that abuts the sheath stop when the sheath 130 is in the extended position. When the sheath 130 is in the extended position, the proximal and distal articulations preferably fix the slide position relative to both the housing and sheath, respectively, which indirectly fixes the sheath 130 relative to the housing, thereby locking the sheath 130 in the extended position. Alternatively, the system may include any suitable locking mechanism to lock the sheath in the extended position. As best shown in FIG. 8E, the proximal articulation 164 of the slider 150 is preferably on a proximal portion of the slider and is a laterally outward extension, such as a tab, that abuts the housing stop. The proximal articulation 164 may or may not include an aperture similar to the aperture 162 of the sheath insert portion to allow passage of the needle 120 through the proximal articulation. The distal articulation 166 of the slider 150 is preferably an extension, such as a nub or catch on the sheath insert portion that catches in the aperture 136 of the sheath stop. Alternatively, the distal articulation 166 may be on any suitable distal portion of the slider. The proximal and distal articulations may project towards the bottom of the slider 150, although they may project in any suitable direction corresponding to the locations of the housing stop on the housing and the sheath stop on the sheath. In other variations, the proximal and distal articulations may be in any suitable locations on the slider and may each be an aperture or extension corresponding to the kinds of housing stop on the housing and sheath stop on the sheath.

Overall in a preferred embodiment, coupling a distal portion of the sheath to the portion of the medical device involves coupling flexible jaws (which are extensions of split portions on the sheath) around the medical device. As shown in FIG. 11A, the sheath is preferably retracted, and restraint tabs 151 on the slider are inserted in restraint slots 138 on the split portions. While the restraint tabs are inserted the restraint slots, the restraint tabs strengthen or lock the coupling between the jaws and the medical device, by substantially preventing the jaws from moving laterally apart. When the housing and slider are pulled away from the medical device, thereby drawing the sheath over the needle, the distal articulation of the slider temporarily abuts the first sheath stop 136 so that the restraint tabs 151 remain engaged in restraint slots 138 and the sheath remains coupled to the medical device. In this intermediate step, the abutment of the distal articulation of the slider against the first sheath stop is preferably overcomes the shear force due to friction between the housing and slider. As shown in FIG. 11C, when the housing is further pulled away from the medical device, the housing pulls the slider away from the medical device until the distal articulation 166 overcomes first stop 136 and abuts the second sheath stop 137, while the proximal articulation 164 of the slider abuts the housing stop 116. Furthermore, as shown in FIG. 11B, when the distal articulation abuts the second sheath stop, the restraint tabs 151 disengage from the restraint slots 138, thereby weakening the coupling between the jaws and the medical device. For instance, after this final step the user can easily provide enough force to separate the extended sheath (surrounding the needle) and the medical device.

Figure 12A:
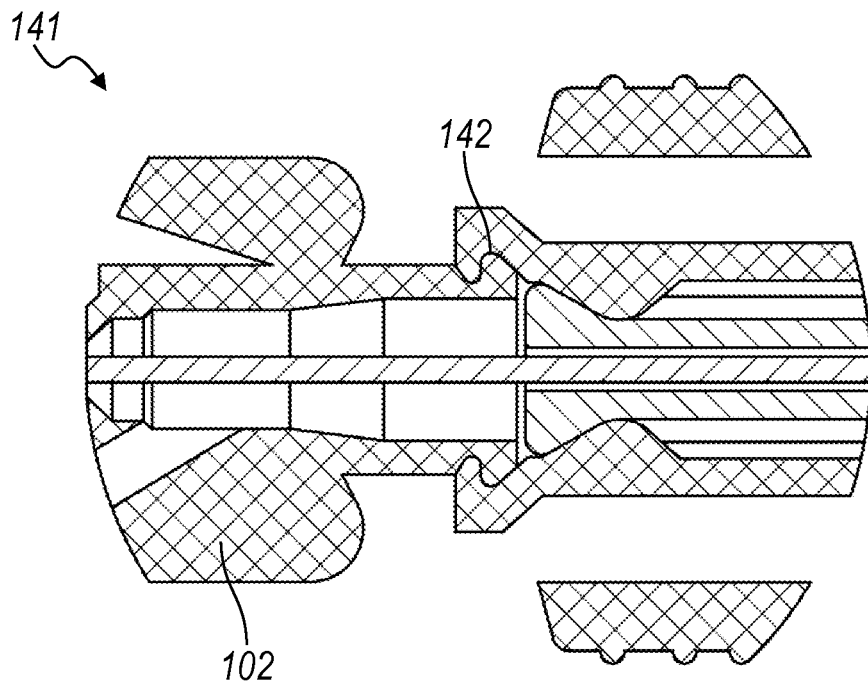
FIGS. 12A and 12B are schematics of the "closed" and "open" configurations of the jaws in the sheath of a variation of the safety needle system of the first preferred embodiment.
Figure 12B:
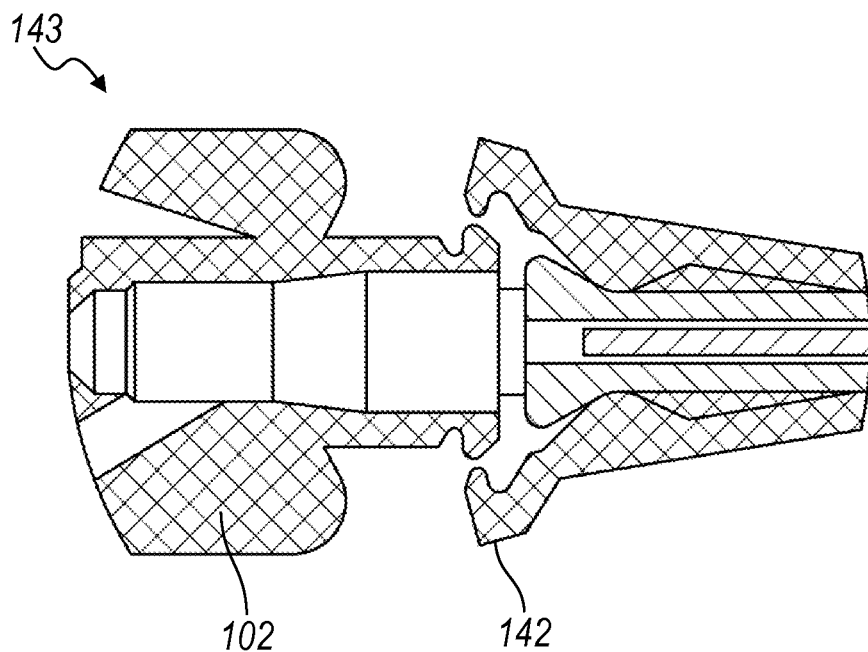

In an alternative embodiment, the slider functions to automatically trigger the decoupling between the sheath 130 and the medical device when the needle is withdrawn from the medical device. In this embodiment, as shown in FIG. 12A, the jaws 142 may be biased into a "closed" configuration 141 in which the jaws tend to grip the mating features on the medical device. As shown in FIG. 12B, the jaws 142 may be manipulated to flex, swing, or otherwise move into an "open" configuration 143 in which the jaws move laterally apart, thereby enabling decoupling of the sheath 130 and medical device 102, such as after the sheath has been drawn into its extended position. The jaws 143 may be manipulated into the "open" configuration automatically when the housing and/or slider 150 is pulled in a proximal direction away from the medical device, thereby automatically decoupling the sheath 130 from the medical device. In this embodiment, as shown in FIG. 13, the slider 150 include protrusions 156 that interfere with the flexible jaws of the sheath 130, such that when the slider is withdrawn from the medical device the protrusions 168 trigger the jaws into the "open" configuration, thereby automatically decoupling the sheath 130 and the medical device.

Safety Needle System of a Second Embodiment

Figure 14A:
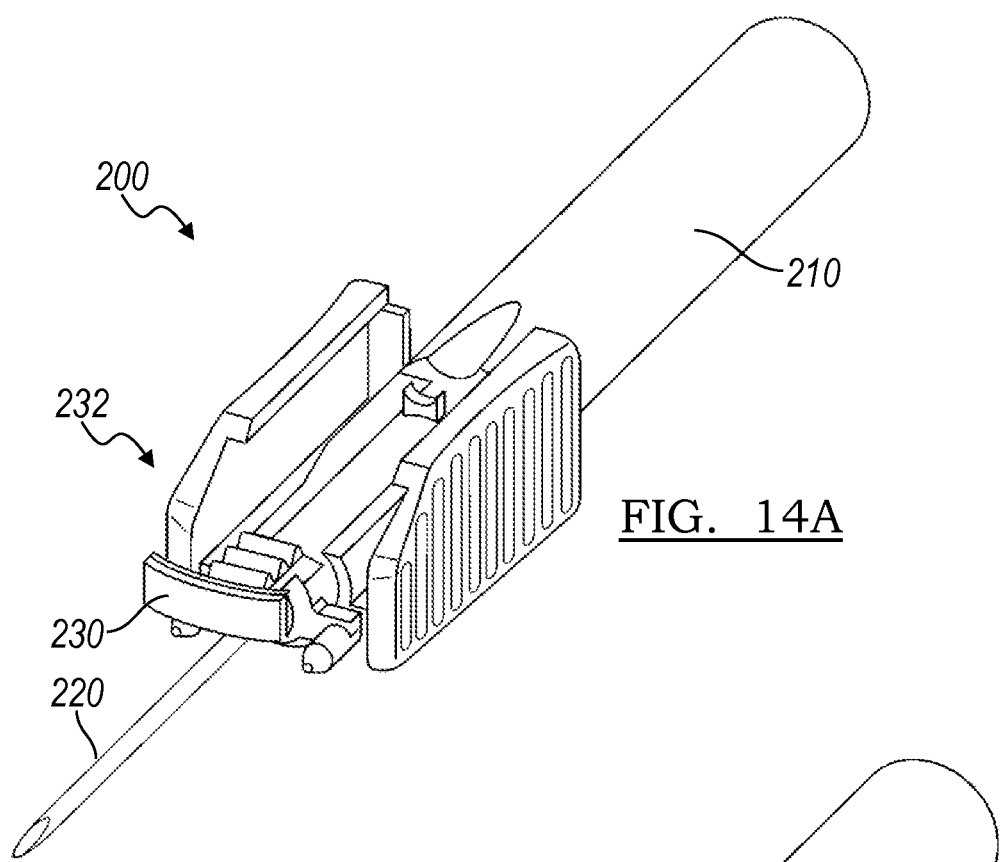
FIGS. 14A and 14B are schematics of the safety needle system of a second preferred embodiment with the sheath in the retracted position and in the extended position, respectively.
Figure 14B:
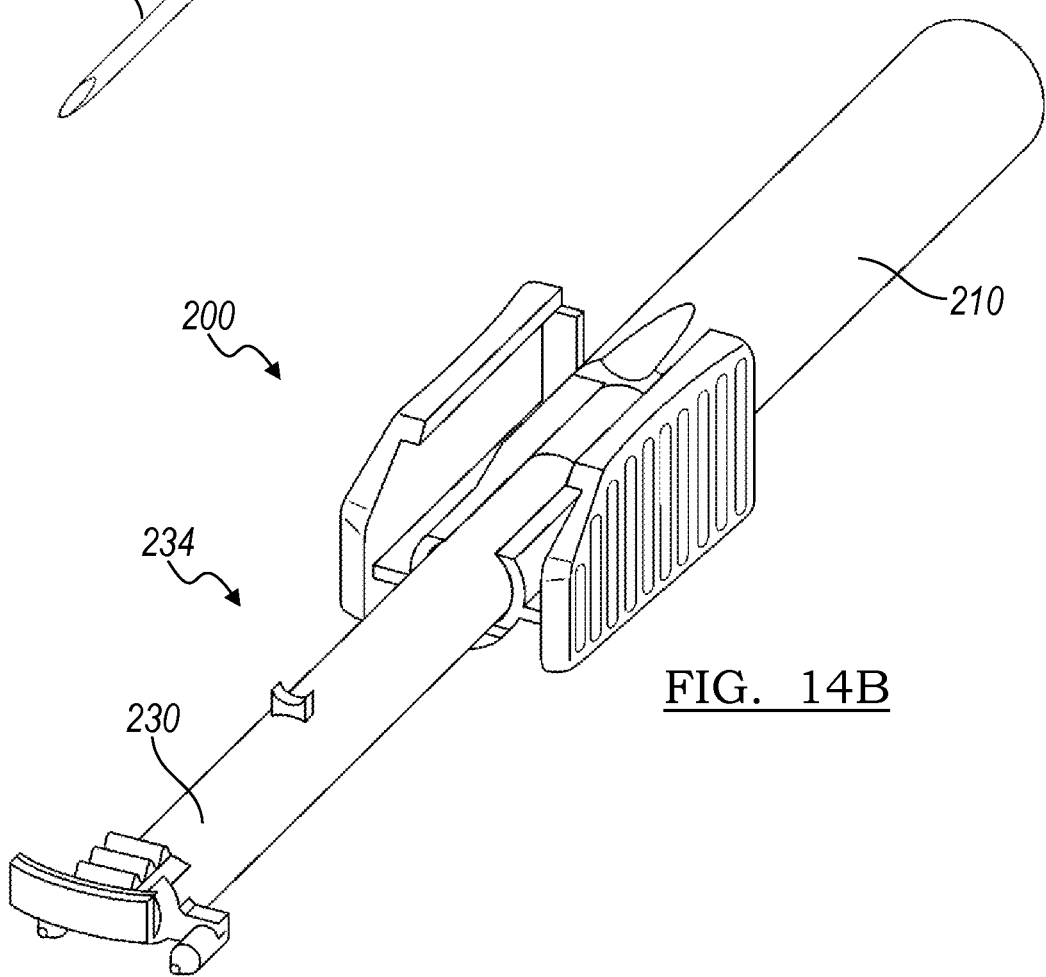

In a second preferred embodiment, as shown in FIGS. 14A and 14B, the safety needle system 200 includes a housing 210 including a needle mount 212 coupled to a setting 214 that approximately axially centers the needle mount 212 within the housing 210; a needle having a distal end insertable through the medical device and a proximal end coupled to the needle mount 212; and a sheath 230 telescopically engaged with the housing 210 and having a distal wall 244 defining a needle aperture 246 and a longitudinal track 242 that is slidingly engaged with the setting 214 of the housing 210. The sheath 230 operates in a retracted position 232 in which the sheath exposes the distal end of the needle and an extended position 234 in which the sheath substantially surrounds the distal end of the needle Like the sheath of the first preferred embodiment of the safety needle system, the sheath 230 is preferably coupleable to the medical device such that removal of the needle from the medical device draws the sheath 230 over the needle, thereby transitioning the sheath from the retracted position to the extended position. The safety needle system preferably further includes a locking mechanism 250. In a preferred embodiment of the safety needle system, when the sheath is in the extended position, a proximal portion of the sheath 230 abuts a housing stop or catch in the housing, and the locking mechanism 250 restrains the sheath in the extended position. In one variation, the locking mechanism 250 is a housing stop including a snap lock cantilevered arm with a free end that is configured to abut the proximal portion of the sheath when the sheath is in the extended position. However, any suitable locking mechanism may be used.

The housing 210 of the second embodiment of the safety needle system functions similarly to the housing of the first embodiment of the system. As shown in FIGS. 15A-15C, the housing 210 is preferably tubular, defining a channel 216 that telescopically engages the sheath 230, and the housing 210 and/or channel 216 is preferably elongated and cylindrical, but may alternatively have any suitable cross-section, such as an oval or an approximate rectangle. Like the housing in the first embodiment, the housing 210 of the second embodiment includes a needle mount 212 to which the needle 220 (which is preferably similar to that of the first embodiment) is coupled. The housing preferably further includes a setting 214 that anchors the needle mount 212 in the housing. The needle mount 212 of the housing is preferably located on a distal end of the housing and is preferably approximately axially centered within the housing. However, the needle mount may alternatively be offset from the center of the housing, or located in any suitable position in or on the housing. The setting is preferably a peg, protrusion, or other inwardly, radially extending feature coupled to an internal wall of the housing. The setting 214 preferably slidingly engages with the sheath 230 to facilitate assembly and/or operability of the sheath in the retracted and extended positions. The setting 214 may have any suitable cross-sectional shape to guide the sliding sheath, such as a square or rectangle. Furthermore, the setting 214 may have a cross-sectional shape that may particularly help reduce lateral movement of the sheath 230 within the housing, such as a dovetail. The housing 210 may also have multiple settings arranged within the channel 216 of the housing that slidingly engage and guide the sheath. For example, the housing may have a first setting on one side of the channel to guide an upper side of the sheath 230, and a second setting on an opposite side of the channel relative to the first setting to guide a lower side of the sheath 230. The needle mount 212 is preferably coupled to the setting 214 such that the setting anchors the needle mount to the housing, but the needle mount and setting may alternatively be independent of one another and located in any suitable position in or on the housing. For example, the setting 214 may be a guide located along the same longitudinal line as the needle mount 212, or on an opposite wall of the needle mount 212, or any suitable location. As shown in FIG. 15C, the relative dimensions of the needle mount and setting preferably form an overhang that defines an alcove space 215 or recess between the needle mount and the housing. The alcove space 215 is preferably dimensioned to accommodate the thickness of the sheath when the sheath is in the extended mode, without permitting the sheath to wobble extensively within the housing.

In some embodiments, the housing 210 further includes one or more handles 218 that a user can grip and manipulate to operate the safety needle system. The handle preferably includes two side grips on opposite sides of the housing that enable secure grasping with one hand. The side grips may be relatively short and narrow along the length of the housing (FIG. 15A) or may be relatively wide and extend along a substantial length of the housing (FIG. 17A). Like the handle of the first preferred embodiment of the system, the handle 218 may include features such as ergonomic contours, ridges to improve friction in the grip, cushioning material such as silicone, or any suitable additions. Furthermore, other variations of the handle may include fewer or more grips (such as a single bulbous handle), and may be particular for specific applications. In some embodiments, the handle may further function as a hub cradle, such as for receiving a catheter hub or stabilization hub such as that described in U.S. patent application Ser. No. 12/855,013, or any suitable hub or other portion of a medical device.

As shown in FIG. 15C, the distal end of the housing 210 may further include a ledge 217 that helps support the sheath 230 when the sheath is in the extended position. The ledge 217 preferably extends beyond the distal end of the housing, preferably on at least an underside of the housing to support the extended sheath against gravity, and may be flat, curved, or any geometry to support the sheath. The ledge may include additional features such as rubberized grips or teeth, or fasteners such as magnets, clips, or adhesive to help secure or support the extended sheath. Furthermore, the ledge may be hingedly attached to the housing, such as for folding to make the system more compact during storage before and/or after use. However, the ledge may have any other suitable geometry and/or arrangement.

The sheath 230 of the safety needle system of the second preferred embodiment of the safety needle system functions similarly to the sheath of the first embodiment of the system.

As best shown in FIG. 17A, the sheath 230 is preferably slidably engaged with the housing 210 such that the sheath passes telescopically within the channel of the housing. The sheath 230 is operable in at least one of a retracted position 232 in which the sheath is at least partially retracted within the housing 210 and exposes the distal end of the needle, and an extended position 234 in which the sheath 230 is extended from the housing 210 and substantially surrounds the distal end of the needle. As shown in FIGS. 16-17, the sheath includes a longitudinal track 242 that slidingly engages with the setting or other portion of the housing, and a distal wall 244 that contributes to covering the distal end of the needle when the sheath is in the extended position.

In one preferred embodiment, the sheath 230 is comprised of two pieces, including a proximal sheath portion 230a and a distal sheath portion 230b. As shown in FIGS. 16A-16E, the proximal sheath portion 230a and the distal sheath portion 230b are assembled to form an integrated sheath body. As shown in FIG. 16E, the proximal sheath portion 230a preferably includes snap latches 231a and the distal sheath portion preferably includes snap holes 231b that receive snap latches 231a in a snap fit fastening manner. However, additionally and/or alternatively, the distal sheath portion may include snap latches and the proximal sheath portion may include snap holes, or the proximal and distal sheath portions may be attached by threads, an interference fit, magnets, adhesive, or in any suitable manner. The proximal and distal sheath portions are preferably assembled within the housing 210, joined around the setting and/or other internal projections inside the housing. During assembly, the distal sheath portion may enter the housing 210 from the distal end of the housing and the proximal sheath portion may enter the housing from the proximal end of the housing. In another variation, the sheath includes one sheath portion and includes features, preferably in the longitudinal track as described below, that facilitates assembly into the housing.

The longitudinal track 242 of the sheath 230 functions to guide transition of the sheath between the retracted and extended positions. The longitudinal track is preferably a slot, but may alternatively be a groove that slidingly engages the setting, or may include a combination of single or multiple slots and/or grooves. The longitudinal track 242 is preferably substantially parallel to a longitudinal axis of the sheath, from a proximal end of the sheath towards a distal end of the sheath, and slidingly engages with the setting and/or needle mount or another feature of the housing 210.

As shown in FIGS. 17 and 18, in the one-piece sheath variation, the longitudinal track preferably includes a series of arcuately offset, adjacent slotted portions, and more preferably two such portions that at least partially overlap to form a single track of varying width. In a preferred embodiment, as best shown in the "unwrapped" view of the track in FIG. 17C, the first track portion 242a runs longitudinally along the sheath 230 from the proximal end of the sheath to a point partially along the length of the sheath. In this embodiment, the second track portion 242b is preferably parallel to and circumferentially offset by an offset angle from the first track portion and runs along substantially the entire length of the sheath 230. Each of the two track portions are preferably approximately as wide, or slightly wider than, the width of the setting of the housing, such that as the sheath 230 telescopically moves within the housing 210 with the setting slidingly engaged with the track 242, the setting 214 freely passes within the longitudinal track. In a preferred embodiment, the first track portion 242a slidingly engages the setting to allow the sheath 230 to pass in a proximal direction up to the end of the first track portion, particularly to at least partially retract the sheath in the housing, such as during assembly of the safety needle system. The second track portion 242b preferably slidingly engages the setting at a different circumferential angle around the sheath 230, to allow the sheath to pass farther in the proximal direction towards the fully retracted position. The second track portion 242b preferably also engages the setting 214 to allow the sheath to pass in a distal direction towards the extended position of the sheath, such as during use of the safety needle system to cover the needle. Although the first and second track portions preferably at least partially share an edge, in other variations the track 242 may include any suitable number of track portions in any suitable arrangement. For example, the first and second track portions may be offset by a relatively large offset angle such that the first and second track portions do not share an edge. Furthermore, as shown in FIG. 18A, the longitudinal track portions may be joined by a lateral track 242c or other open passageway (such as an open distal end of the sheath as shown in FIG. 18B) so that rotation of the sheath within the housing enables the setting to travel between the track portions.

As shown in FIGS. 17B, 18A and 18B, the longitudinal track 242 and/or other portion of the sheath 230 preferably also defines a catch 238 at the proximal portion of the sheath that functions to prevent the extended sheath from fully exiting the housing 210. The catch 238 is preferably arranged at the proximal portion of the sheath and abuts the setting and/or needle mount when the sheath is in the extended position. The catch 238 may fit into the alcove space 215 of the housing. Another catch mechanism, such as springs or latches, may additionally and/or alternatively be used to prevent the sheath from fully exiting the housing. In one or more of these variations, the sheath is preferably restrained from sliding beyond a particular point in the extension (distal) direction.

The distal wall 244 of the sheath 230 functions to substantially cover the distal end of the needle when the sheath is in the extended position, and further functions as a stop against the needle mount and/or setting when the sheath 230 is in the retracted position, to prevent the sheath from fully retracting into the housing 210. The distal wall 244 forms a substantially full or partial face on the distal end of the sheath, and defines a needle aperture 246 or hole large enough to receive and allow passage of at least a portion of the needle. The needle aperture 246 may be an opening in the distal wall of the sheath (FIG. 18B) or may be in a guide or partial needle covering that extends beyond the distal wall (FIG. 16). To limit sheath retraction up to a point (such as less than fully retracted within the housing 210, such that the distal end of the sheath is still extending beyond the distal end of the housing), the distal wall 244 may abut the needle mount and/or setting when the sheath is in the retracted position, or additionally and/or alternatively the proximal end of the sheath may butt against a proximal wall or another stop in the housing 210. In at least one of these manners, the sheath is preferably retraining from sliding beyond a particular point in the retraction (proximal) direction.

The distal end of the sheath 230 is adapted to mechanically and/or manually couple to the medical device, similar to the sheath of the first preferred embodiment of the system.

Figure 19B:
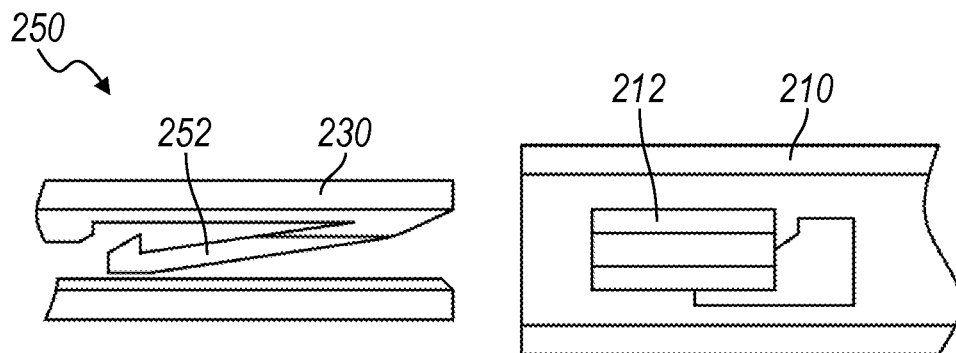
FIGS. 19A-20D are schematics of variations of the locking mechanism in the safety needle system of a second preferred embodiment.
Figure 19C:
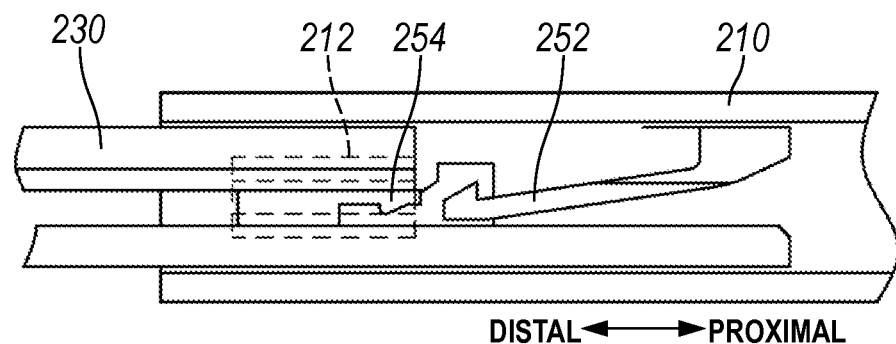
Figure 19D:
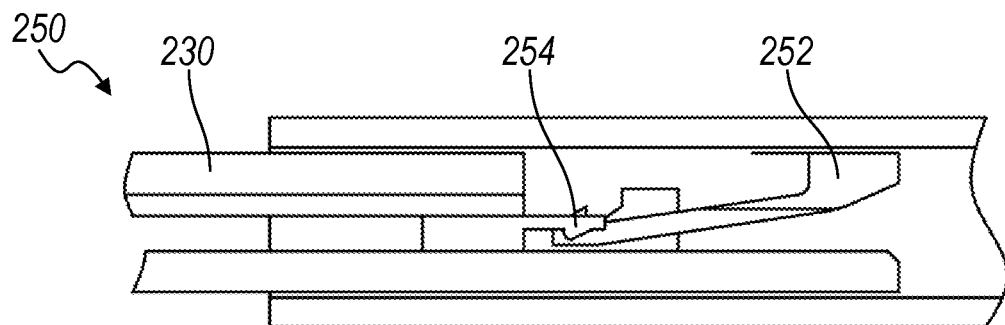

The locking mechanism 250 of the safety needle system functions to restrain the sheath 230 in the extended position and prevent the sheath from returning from the extended position to the retracted position. In some embodiments, the safety needle system may include two or more locking mechanisms in the sheath 230 and/or housing 210. In one variation, as shown in FIGS. 19A-19D, the locking mechanism 250 may be coupled to the sheath 230 and/or housing 210. For example, the locking mechanism 250 may be a tab 252, coupled to the sheath, that engages a corresponding catch 254 or other stop in the housing 210 such as near the setting and needle mount (or other suitable location in the housing), to substantially lock the sheath in the extended position. In a one-piece sheath, the tab 252 is preferably near the proximal end of the sheath. In a two-piece sheath, the tab may be located on the proximal sheath portion or the distal sheath portion. The tab preferably enables passage of the sheath 230 within the housing 210 in a proximal direction (e.g. only in assembly), while substantially preventing passage of the sheath in the proximal direction when the tab engages the catch when the sheath is in the extended position. For instance, as shown in FIG. 19B, during assembly when the sheath 230 is passed in the proximal direction into the housing 210, the sheath may be rotated to a particular angle such that the setting and/or needle mount preferably deflect the tab towards the wall of the housing 210, enabling the sheath to free pass in the proximal direction within the housing 210. As shown in FIGS. 19C and 19D, during operation of the safety needle system, when the sheath is drawn out to its extended position, a barbed end of the tab engages and stops on the catch of the housing, thereby substantially preventing movement of the sheath in the proximal direction and restraining the sheath in its extended position.

Figure 20A:
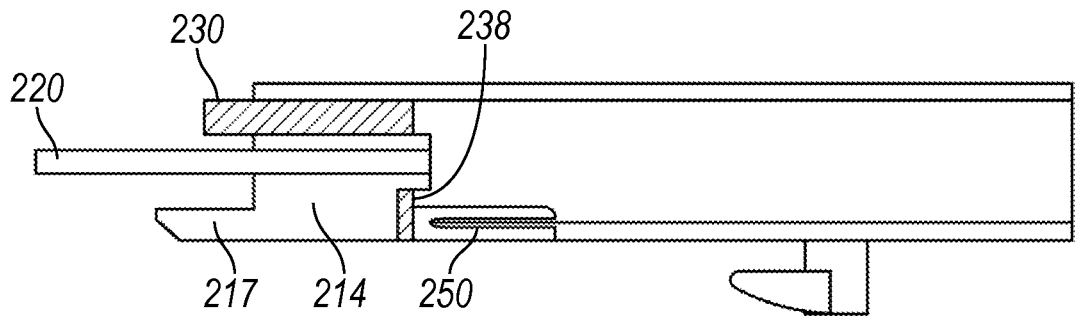
Figure 20B:
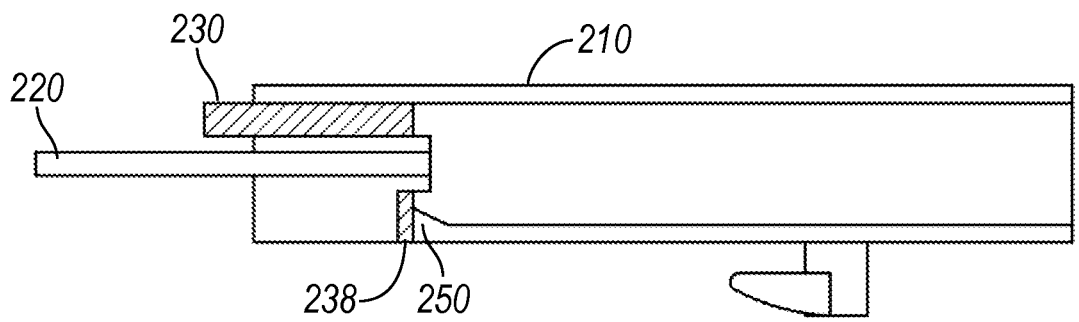
Figure 20C:
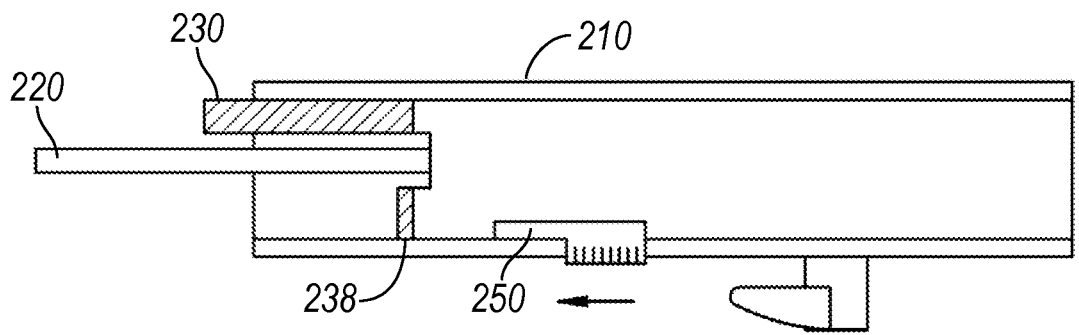
Figure 20D:
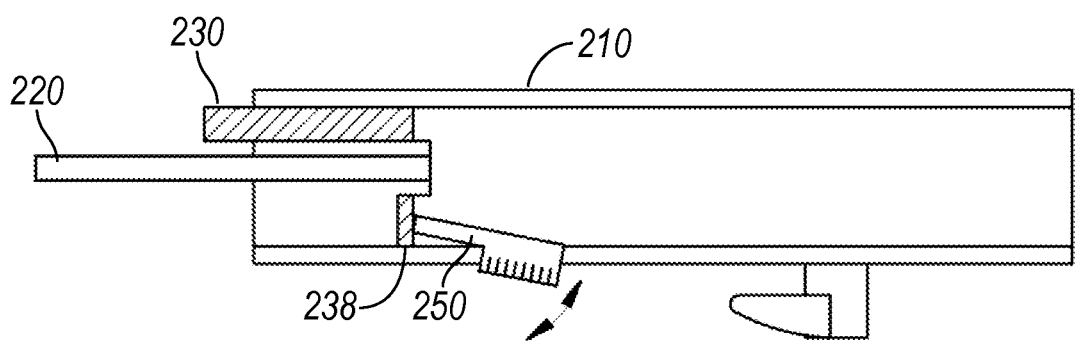

In another variation, as shown in FIGS. 20A-20D, the locking mechanism 250 includes a housing stop coupled to the housing 210. In the extended position of the sheath 230, the catch of the sheath preferably abuts the setting or other stop of the housing 210 and the housing stop abuts a proximal face of the catch, thereby trapping the catch between the setting and the housing stop. The housing stop is preferably a snap lock cantilevered arm or tab on a wall of the housing 210 that is radially deflectable inwards (FIG. 20A) and/or have a projection that extends radially inwards. (FIG. 20B). In other variations, the locking mechanism 250 may be a sliding latch (FIG. 20C), lever, (FIG. 20D), push button, or another suitable mechanism that is engageable to trap the catch of the sheath 230 against the setting of the housing, thereby locking the sheath in the extended position. In further variations, the locking mechanism 250 may additionally and/or alternatively abut a distal portion, central portion, or any suitable portion of the sheath. The locking mechanism is preferably integrally formed with the housing 210, but may alternatively be a separate piece that is coupled to the housing during assembly of the safety needle device.

Preferably, the locking mechanism 250 is disengaged or otherwise does not interfere with the ability of the sheath 230 to pass in a proximal direction to its retracted position during assembly of the safety needle, or before extended position of the sheath 230 is desired for covering the needle tip. For example, the free end of the cantilever arm may extend into the alcove space 238 adjacent to the setting of the housing 210 out of the assembly path of the sheath, such that during assembly the cantilever arm does not accidentally abut the catch of the sheath 230 and prematurely lock the sheath in the extended position. In other variations, the locking mechanism may be selectively disengaged according to its mechanical nature, such as by sliding a latch or pivoting a lever out of the way of the sheath when the sheath is to be retracted (e.g. during assembly or if the needle is to be uncovered).

In either preferred embodiment, the safety needle system may further include a protective cap 260 that covers the distal end of the needle prior to use of the safety needle system or whenever the sheath is in the retracted position, such as during transport or storage. The protective cap 260 may be a sleeve that surrounds at least a portion of the exposed needle, and/or include a blunt stopper that occludes or blunts the distal end of the needle. However, any other suitable type of cap may be used.

Figure 21A:
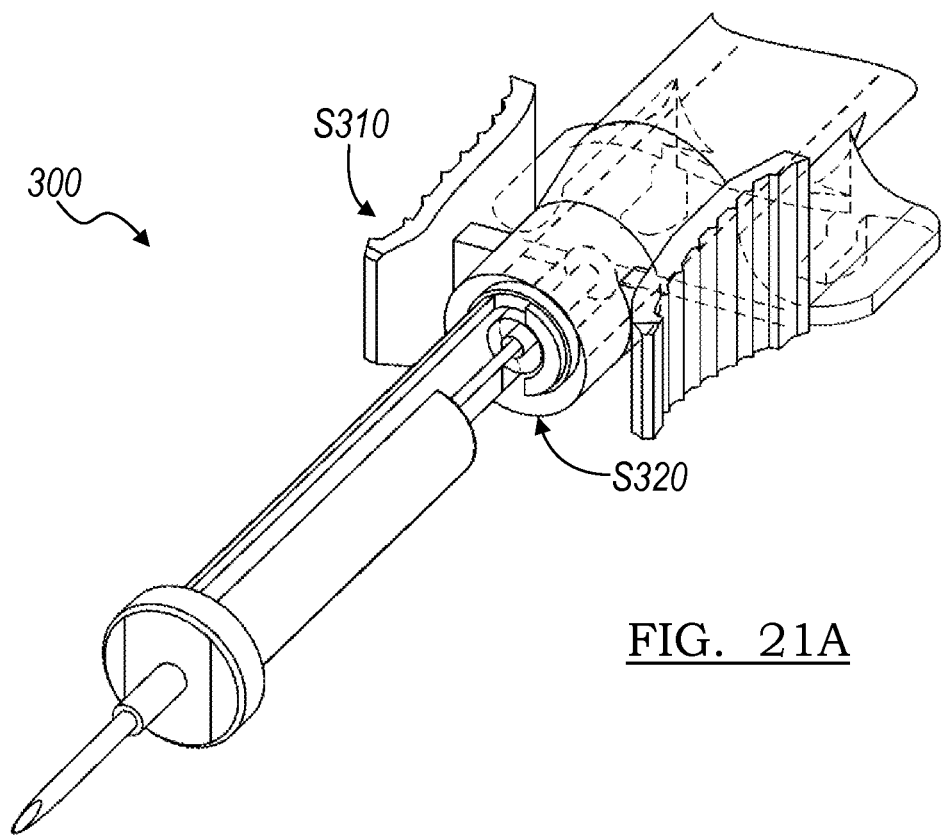
FIGS. 21A-22B are schematics of the method of assembling the safety needle system of a second preferred embodiment.
Figure 21B:
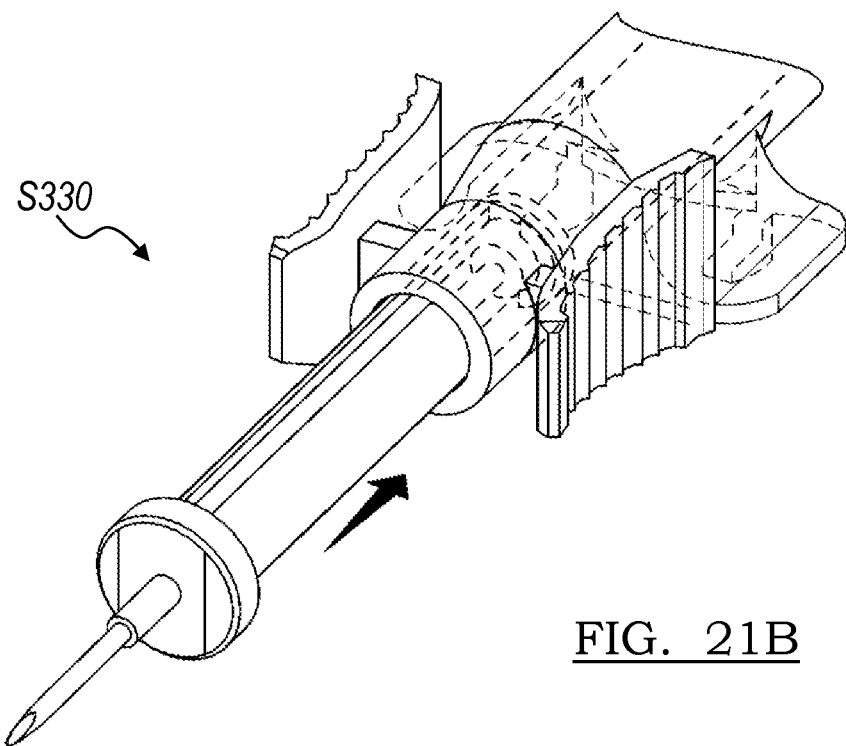
Figure 21C:
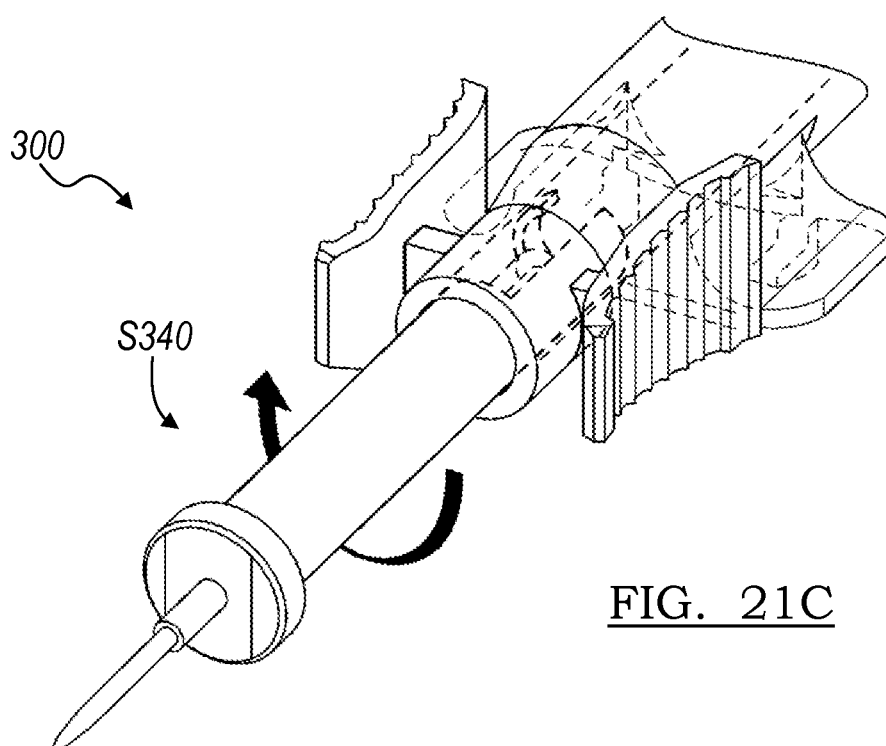
Figure 21D:
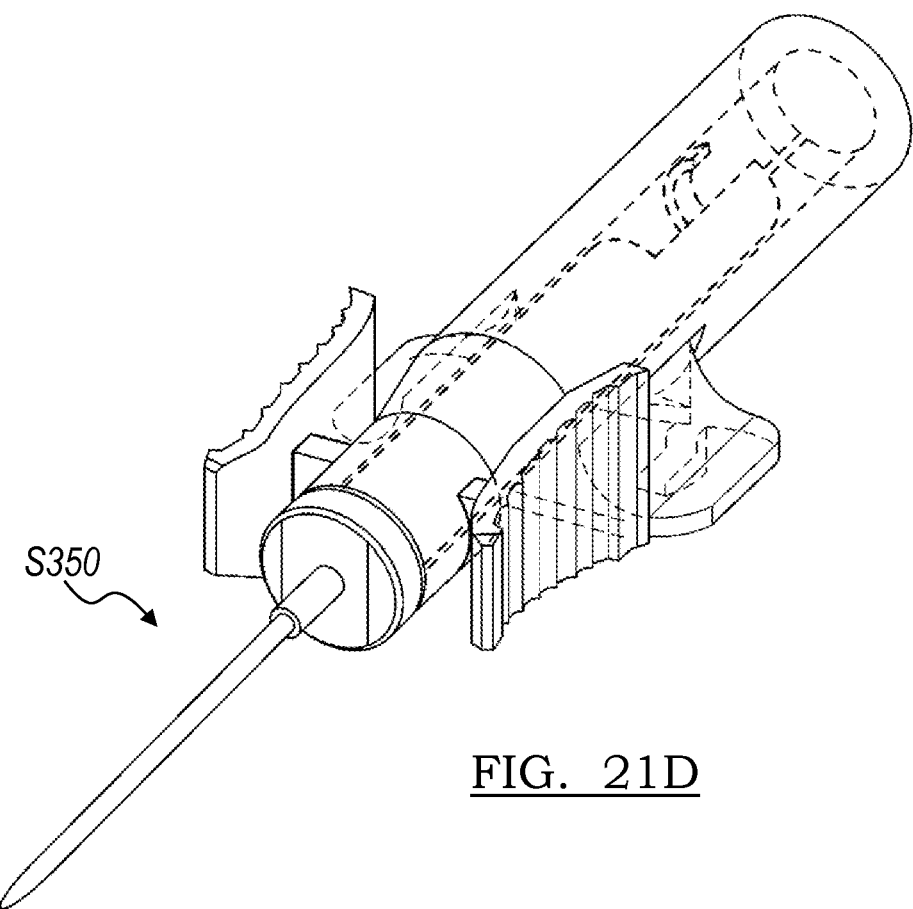
Figure 21E:
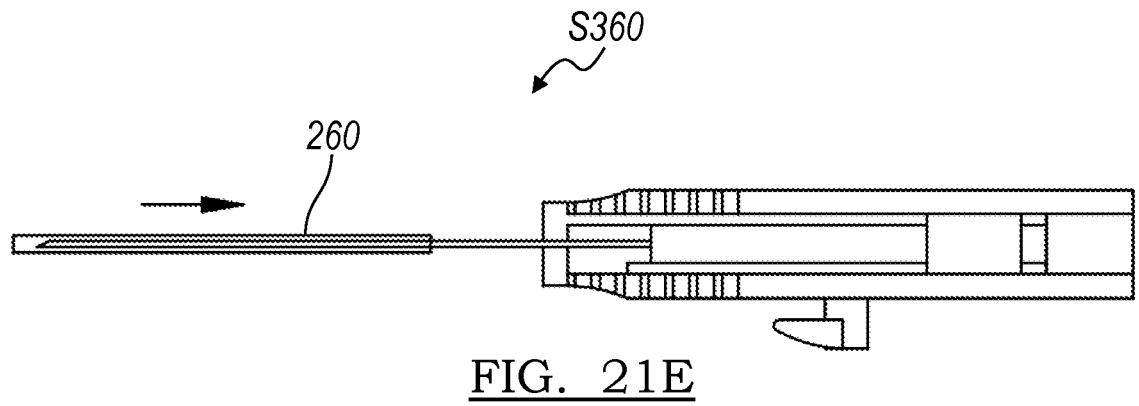
Figure 22A:
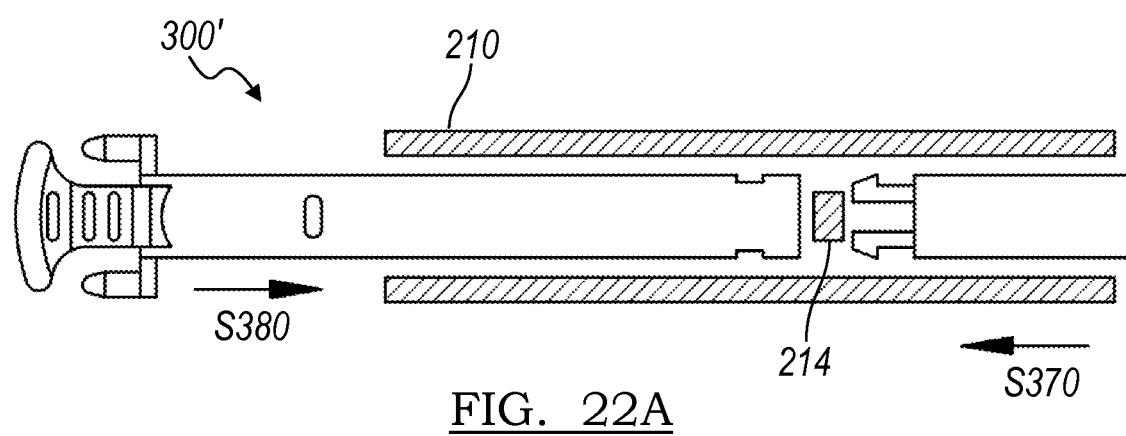
Figure 22B:
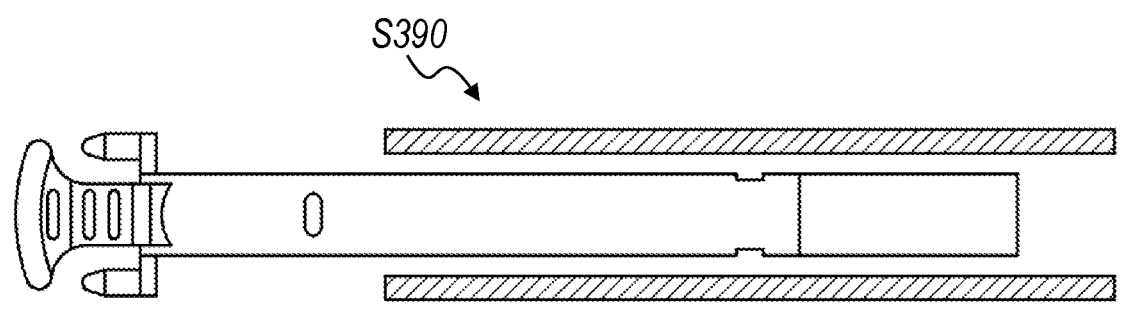

As shown in FIGS. 21A-21D, the method of assembling the safety needle system 300 of the second embodiment includes: inserting a proximal end of the sheath into a distal end of the housing (Step S310); engaging the setting of the housing within the first track portion of the longitudinal track (Step S320); sliding the sheath telescopically to at least a partial retracted position in the housing (Step S330), with the setting of the housing traveling within the first track portion of the longitudinal track; rotating the sheath within the housing by the offset angle (Step S340) to engage the setting of the housing within the second track portion of the longitudinal track; and sliding the sheath into a full retracted position in the housing (Step S350), with the setting of the housing traveling within the second track portion of the longitudinal track. As shown in FIG. 21E, the method may also include sterilizing the needle and/or placing a protective cap (Step S360) onto a distal end of the needle that helps maintain sterility and protect users from accidental needle pricks during transport and storage. This method may be used to assemble an embodiment of the safety needle system with a one piece sheath, but a variation 3oo' may similarly be used to assemble a safety needle system with a sheath having two or more pieces. In another variation 300', to assemble a two-piece sheath variation of the system, the proximal sheath portion and the distal sheath portion are preferably coupled to one another around the setting or other housing stop of the housing. For instance, method 300' may include inserting the proximal sheath portion into the proximal end of the housing (Step S370), inserting the distal sheath portion into a distal end of the housing (Step S380), and coupling the proximal sheath portion and distal sheath portion to one another (Step S390), preferably around the setting. After assembly, the sheath is preferably approximately concentrically nested within the housing. The safety needle system may be assembled during manufacture and supplied to the user with the sheath in its retracted position, or with the sheath in its extended position. Alternatively, the safety needle system may be assembled by the user prior to use.

Safety Needle System—Septum

In either preferred embodiment, the safety needle system may further include one or more instances of a septum 400 that functions to seal any body fluids, such as blood, or other potential biohazards within the sheath as the sheath passes over the needle into the extended position, as the needle is withdrawn from the medical device. Although the safety needle system with septum is primarily shown with the system of the first preferred embodiment, the second preferred embodiment of the system may also include a septum 400. The septum 400 is preferably coupled to the sheath 130 and more preferably within the sheath. The septum 400 in the safety needle system is configured to couple to the medical device (e.g. a septum in the catheter hub or other portion of any medical device) in a fluid-tight manner, to help prevent fluid leakage through the joint between the medical device and the safety needle system. For example, the end of the safety needle system septum may be circumferentially enclosed by the medical device, or the medical device may be circumferentially enclosed by the safety needle system septum. As another example, the joint between the safety needle system and the medical device may include a fluid-tight butt joint or other sealant.

Figure 23:
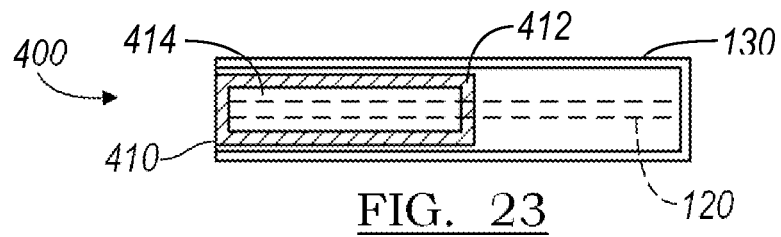
FIGS. 23-26B are schematics of the safety needle system of a preferred embodiment with a septum.

As shown in FIG. 23, the septum preferably includes a first seal 410 and a second seal 420. The first seal 410 is a defense against fluid escaping from one end of the septum, and the second seal 420 functions as a defense against fluid escaping from another end of the septum. In some embodiments, the septum 400 may include fewer or more seals similar to the first and second seals, which may be suitable for some applications to modify the amount of fluid leakage protection. The septum 400 preferably defines a cavity 414 between the first and second seals that may contain trapped fluid. The cavity 414 may be larger than the diameter of the needle to reduce frictional force as the septum passes over the needle. However, the cavity may alternatively be closely fit over the needle, and/or include a material with a lower friction coefficient and/or fluid absorbent material. As shown in FIG. 24-26, the septum length, and more preferably the cavity length, is at least a long as the notch extent distance of the needle and positioned as such that when the sheath is in the extended mode, the notch is fully contained within the septum. In some embodiments, the needle may include additional fluid exit points such as multiple notches along its length, and the safety needle system may include a longer septum or multiple septa to contain the multiple fluid exit points on the needle.

Figure 24A:
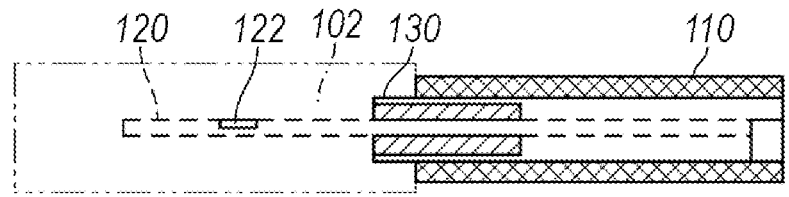
Figure 24B:
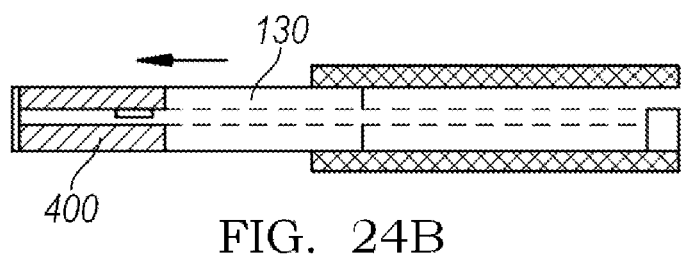
Figure 25A:
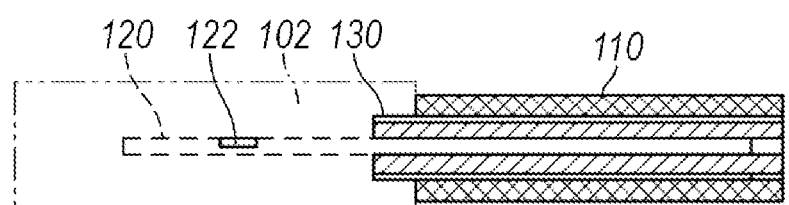
Figure 25B:
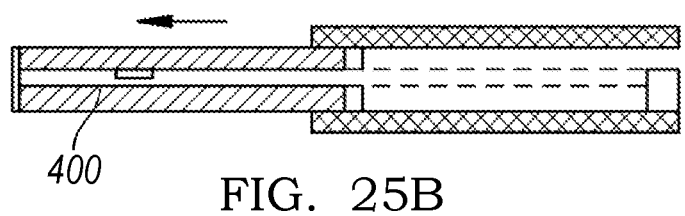
Figure 26A:
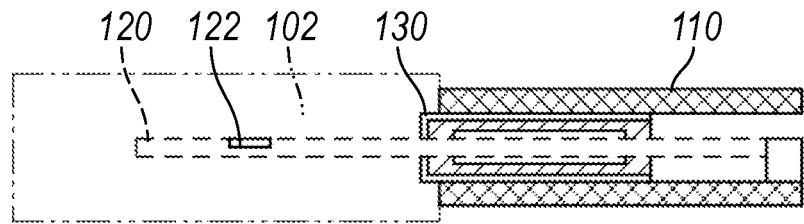
Figure 26B:
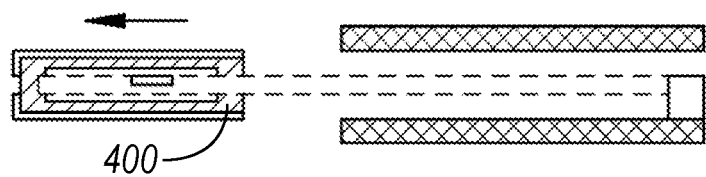
Figure 27A:
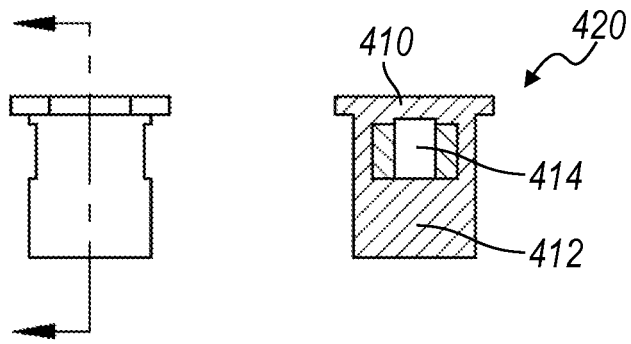
FIGS. 27A-31E are schematics of septum variations in the safety needle system of a preferred embodiment.
Figure 27B:
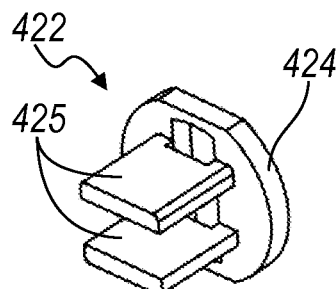
Figure 27C:
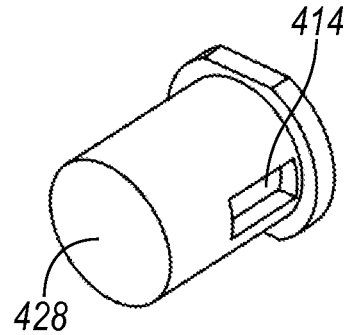
Figure 27D:
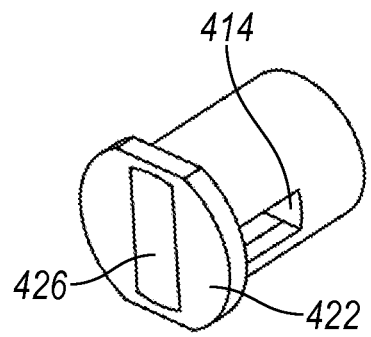

As shown in FIGS. 24A and 24B, the safety needle septum 400 may be shorter than the length of the sheath 130, such as near the distal end of the sheath so that when the sheath is in the extended position, the septum contains a portion of the needle body including the distal end of the needle and the notch. Alternatively, the safety needle septum may be at least substantially the same length as the sheath. For example, as shown in FIGS. 25A and 25B, the septum may be nearly the same length as the sheath such that when the sheath is in the extended position, the septum contains a large portion needle body. In another example, as shown in FIGS. 26A and 26B, the sheath and septum may be at least as long as the notch extent to contain the notch, but shorter than the overall needle length.

The septum 400 may include an elastomeric material, and may have a diameter slightly larger than the diameter of the sheath, such that compression of the septum, when assembled in the sheath, seals the annular gap between the outer circumferential edges of the septum and the walls of the sheath, thereby preventing fluid from escaping through the annular gap, and further maintaining the coupling between the septum and the sheath, similar to a press fit. The septum may additionally and/or alternatively include a sealant material applied between the outer surface of the septum and the sheath, and/or be temporarily or permanently bonded to the sheath such as with sonic welding, chemical welding, or adhesive.

As shown in FIGS. 27A-27D, in a preferred embodiment of the septum, the septum 420 includes a rigid core 422 and a compressible plug 428 coupled to the rigid core 422. The rigid core 422 is a framework that preferably includes a back wall 424 with aperture 426 and wall members 425 extending from the back wall. The back wall 424 may provide a flange that helps seat the septum 420 within the sheath 130. The wall members 425 are preferably substantially parallel, but may be in any suitable relative orientation that defines a gap between the wall members. The compressible plug 428 is coupled partially or wholly around the rigid core 422, covering or filling the aperture 426 and surrounding the wall members 425 to define a cavity 414 in a central portion of the septum. One end of the compressible plug 428 forms the first seal 410, and the other end of the compressible plug covering the aperture of the back wall forms the secondary seal 412. The aperture 426 of the back wall allows needle puncture access through the rigid core into the septum cavity. The rigid core is preferably made of a rigid plastic such as polycarbonate, acrylonitrile butadiene styrene (ABS) or other styrene, and the compressible plug preferably includes an elastomeric material such as isoprene or silicone. However, the rigid core and compressible plug may include any suitable materials. The compressible plug is preferably coupled to the rigid core in an overmolding manufacturing process, but may additionally and/or alternatively include other coupling mechanisms such as adhesive.

Figure 28A:
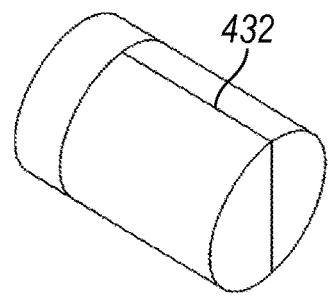
Figure 28B:
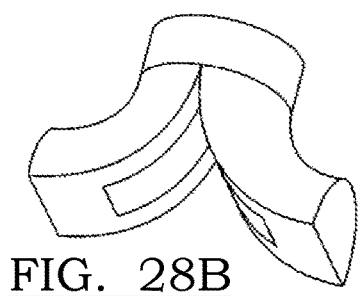
Figure 28C:
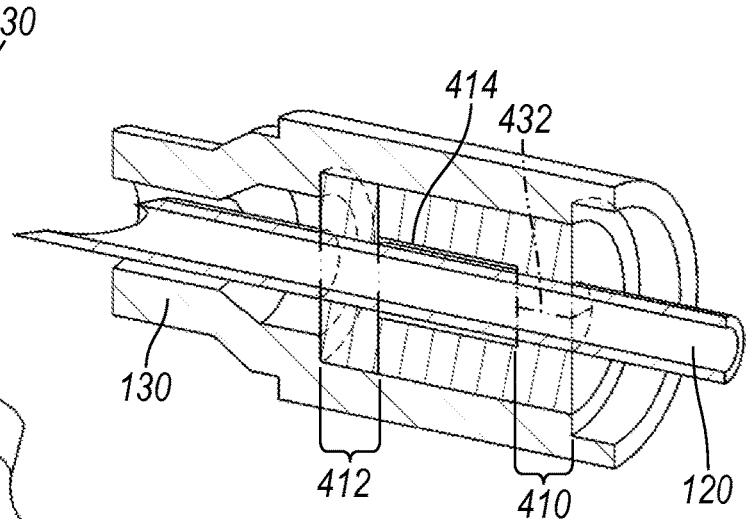

In a first alternative variation, as shown in FIGS. 28A-28C, the septum is a split septum 430 that includes a split 432 along a portion of its length. The split longitudinally divides the septum into approximately two halves or other multiple portions. The split 432 may begin at the second seal 412 and terminate near the inner face of the first seal 410, such that the split travels along at least half of the length of the septum and is joined near the first seal, but the split 432 may alternatively be any suitable length, including along the entire length of the septum such that the septum includes two separate portions. As shown in FIG. 28C, when the septum is assembled into the sheath, the sheath preferably radially compresses the septum material to close the split, thereby forming the cavity and the second seal. The split septum may be manufactured through injection molding, such as with a mold having a cavity as shown in FIG. 28B. In another example of this variation, the split 432 may begin at the first seal and terminate at the second seal. In yet another example of this variation, the septum may be split longitudinally along two or more lines, forming three or more split portions.

Figure 29A:
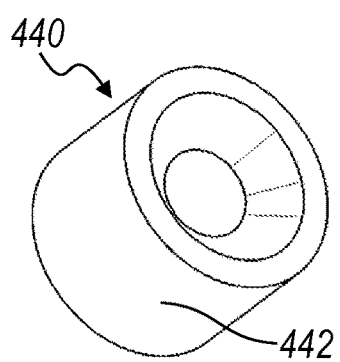
Figure 29B:
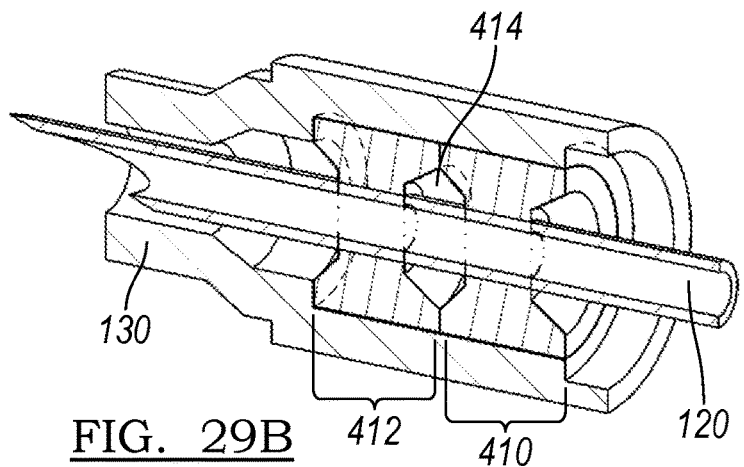

In a second alternative variation, as shown in FIGS. 29A and 29B, the septum is a dual grommet septum 440 that includes at least two septum pieces 442 or "grommets" placed serially within the sheath. One of the septum pieces 442 forms the first seal 410 and another septum piece 442 forms the second seal 412. The septum pieces are preferably immediately adjacent to each other such that part of their interior faces are contacting and form a fluid-tight seal against the sheath. The interior faces of the septum pieces may be chamfered or radiused to define the septum cavity 414 between the septum pieces, but the septum pieces may alternatively have any suitable geometry. Alternatively, the septum pieces may be separated by a distance, such that the septum cavity is at least partially formed by the walls of the sheath 130. In other examples of this variation, the septum may includes three or more septum pieces placed serially within the sheath, such as to provide three or more seals.

Figure 30A:
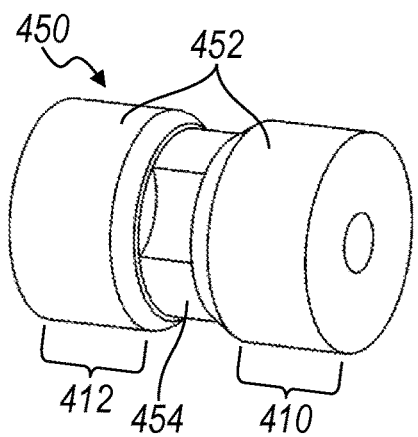
Figure 30B:
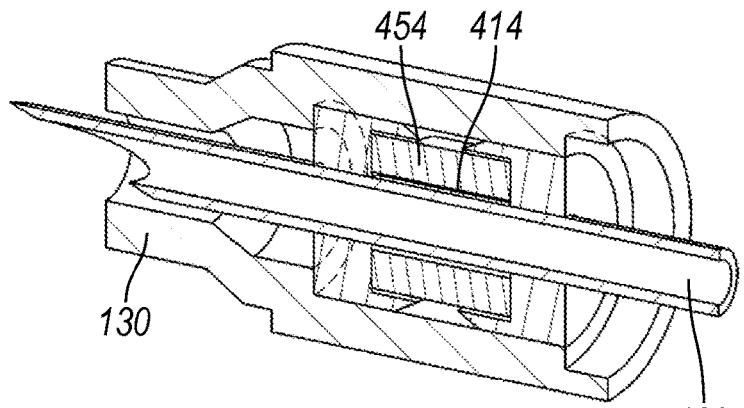

In a third alternative variation, as shown in FIGS. 30A and 30B, the septum 450 includes at least two separate septum pieces 452 and an inner sleeve 454 disposed between the septum pieces. In this variation, two septum pieces 452 are placed serially within the sheath 130, either directly adjacent to each other or separated by a distance. One of the septum pieces 452 forms the first seal 410 and another septum piece 452 forms the second seal 412. The interior faces of the septum pieces are preferably adapted to receive the inner sleeve 454, such as by defining axially aligned recesses. The inner sleeve 454 may be cylindrical and sized to fit within the recesses of the septum pieces, with an inner diameter large enough to form a cavity that accommodates the diameter of the needle. The inner sleeve is preferably rigid, and made of a thermoplastic material or any other suitable rigid material, although the inner sleeve may be made of any suitable material. In other examples of this variation, the septum may include more than two septum pieces, such as further including an outer sleeve-like septum part surrounding the inner sleeve.

Figure 31A:
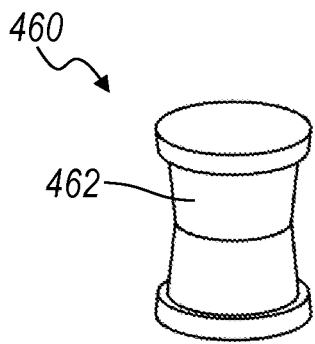
Figure 31B:
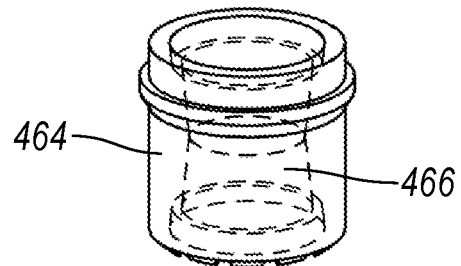
Figure 31C:
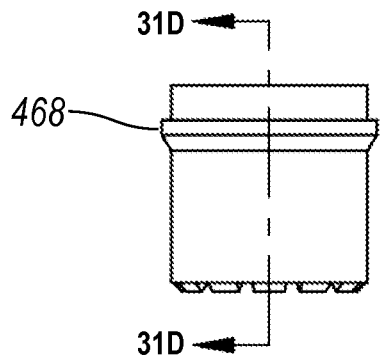
Figure 31D:
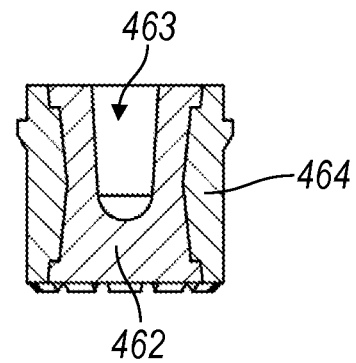
Figure 31E:
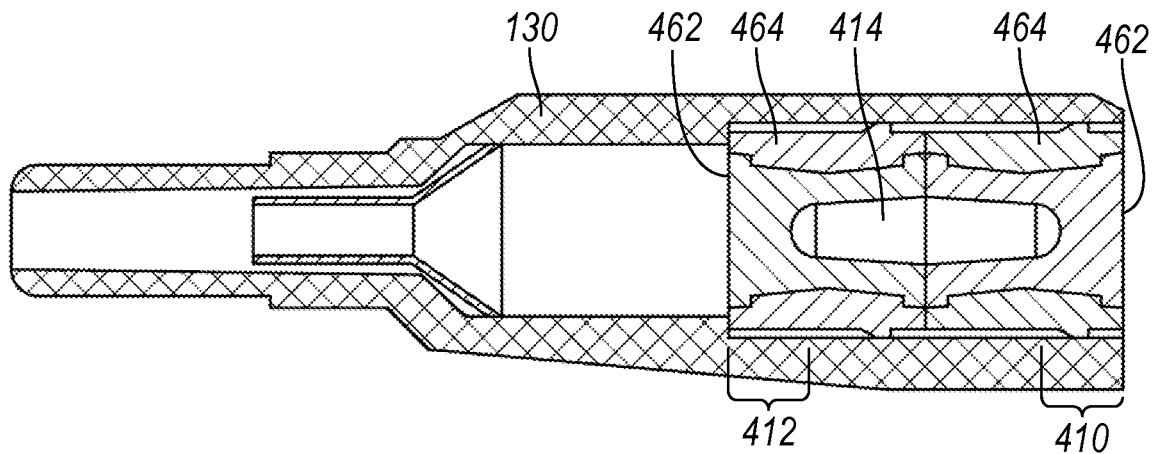

In a fourth alternative variation, as shown in FIGS. 31A-31E, the septum 460 includes a housing with first and second housing portions 464 and first and second septum pieces 462. In this variation, as shown in FIG. 31E, the septum includes a first half and a second half that is substantially a mirrored version of the first half, with each half including a housing portion 464 and a corresponding septum piece 462. As shown in FIG. 31A, each housing piece 464 includes a tapered, hourglass-shaped chamber 466 for receiving a corresponding septum piece. The taper in the chamber helps reduce relative movement such as translational movement between the septum piece and the housing. Each housing piece may further include an external annular flange 468 or other protrusion that helps reduce translational movement between the housing and the sheath. The two housing pieces 464 may be coupled together and/or to the sheath 130 through ultrasonic welding, epoxy or other adhesive, threads, and/or any suitable coupling mechanism. As shown in FIG. 31D, each septum piece preferably includes a cavity 463 that extends inward from one open end of the septum piece, and the septum pieces are preferably assembled such that the open ends of the septum pieces abut against each other. In this manner, as shown in FIG. 31E, the closed ends of the septum pieces form first and second seals, respectively, of the septum, and the joined open ends of the septum pieces form enclosed septum cavity 414. The housing and septum pieces are preferably combined, with a corresponding septum portion nested within (e.g. molded into or pressed into) each housing portion, and the combined housing and septum pieces are preferably mounted within the sheath.

In an alternative embodiment, the septum 400 may have only one seal. In a first alternative variation of this embodiment, the septum is made of a flexible material that self-seals to form a hermetic seal within the sheath. This self-sealing septum prevents fluid from passing out of the sheath, contributing to a closed system in which blood and other fluids will not exit the sheath after the needle is contained inside the sheath in the extended position. In a second alternative variation, the septum may be sealed with a plug, such as a stopper or sealant material applied to the septum by a user. The plug may include a separate stopped plug applied to the distal end of the sheath, a sliding piece that the user slides to gate off the distal end of the sheath, a hinged piece that the user swings over the distal end of the sheath, and/or any suitable septum piece. Any of these single seal variations of the septum may be repeated serially to form two seals or more seals.

The septum may be one or more of the embodiments and variations described above, and/or one or more of the embodiments described in U.S. Provisional Applications 61/346,292 filed 19 May 2010 and 61/407,797 filed 28 Oct. 2010, which is each incorporated in its entirety by this reference. Furthermore, the septum may be any suitable mechanism that helps prevent escape or leakage of fluid from the sheath.

Figure 32:
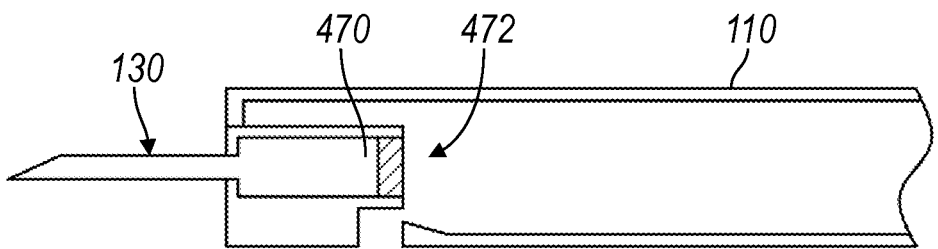
FIG. 32 is a schematic of a housing with vent chamber in the safety needle system of a preferred embodiment.

In either preferred embodiment, as shown in FIG. 32, the safety needle housing 110 may additionally and/or alternatively include a vent chamber 470 and a vent cap 472 that seals one end of the vent chamber. The vent chamber 470 may be coupled to the needle mount, such that the vent chamber receives blood or other body fluids through the needle. In one variation, the vent chamber includes a recess within the needle mount of the housing, and the proximal end of the needle is inserted into an entrance of the vent chamber to carry fluids into the vent chamber. In this variation, the interface between the needle and the vent chamber is sealed to further guard against release of fluids, such as with a filter, gasket, O-ring, epoxy, or any suitable seal material or mechanism. Furthermore, the housing may include a vent cap 472 that seals one end of the vent chamber to prevent passage of fluid throughout the rest of the housing and safety needle system. The vent cap is preferably hydrophobic, preventing fluid from exiting the vent chamber while allowing air to exit the vent chamber, thereby creating a pressure differential across the needle body due to the difference between vascular and atmospheric pressures. This pressure differential causes the blood in the needle to "flash back" into the vent chamber. In another variation, the proximal end of the needle includes an enlarged needle chamber volume that receives fluids, and the vent chamber of the housing receives the needle chamber. In this variation, the fluids are contained within the needle structure, which is in turn mounted in the housing.

Figure 33A:
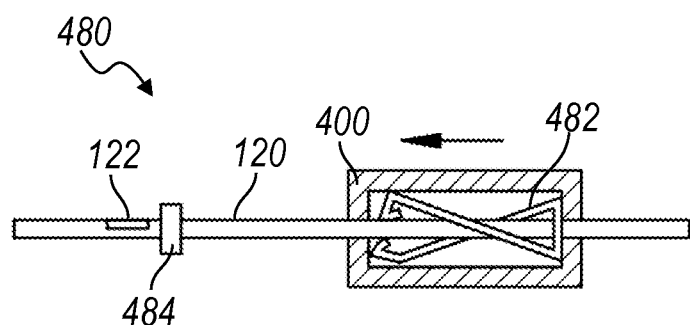
FIGS. 33A and 33B are schematics of catch variations in the safety needle system of a preferred embodiment.
Figure 33B:
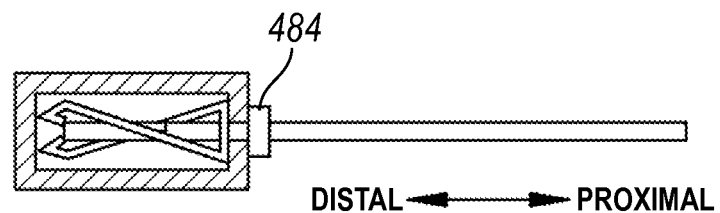

In either preferred embodiment, the safety needle system may further include a catch 480 that helps lock the septum 400 (or alternatively a portion of the sheath 130 without a septum) in place over the notch 122 and/or the distal end of the needle 120. The catch 380 may additionally and/or alternatively fix the sheath in the extended position. As shown in FIGS. 33A and 33B, in one variation the catch may be coupled to an internal portion of the septum, such as a spring clip within the septum cavity (or other portion of the septum or sheath) that engages the needle once the sheath is in its extended position. When the spring clip engages the needle, the spring clip prevents movement of the sheath in a proximal direction, thereby locking the septum in place. As also shown in FIGS. 33A and 33B, in another variation the catch is a compressible ring 484 or nub on an external surface of the needle 120 that compresses when the septum 400 passes over the catch in a distal direction, and expands again when the septum covers the notch and/or distal end of the needle, thereby preventing movement of the sheath in a proximal direction and locking the septum in place.

Method of Using the Safety Needle System

As shown in FIGS. 34-40, the method 500 of using the safety needle system of the embodiments described above with a medical device, such as with a catheter hub, preferably includes: inserting the needle into a patient (Step S510); coupling a distal portion of the sheath to the medical device (Step S520); pulling the housing away from the medical device (Step S530) in a proximal direction relative to the needle; allowing the sheath to slide in a distal direction towards the extended position (Step S540), thereby drawing the sheath into the extended position; locking the sheath in the extended position (Step S550); and uncoupling the distal portion of the sheath from the medical device (Step S560).

Figure 34A:
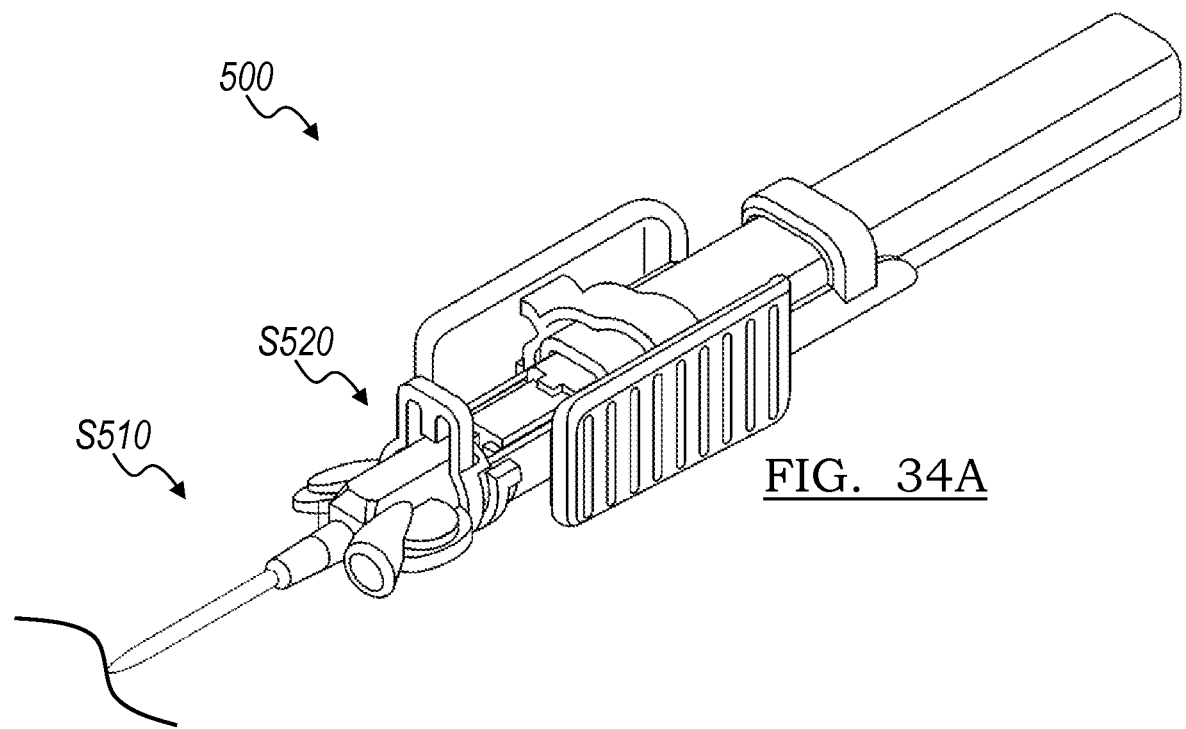
FIGS. 34A-40B are schematics of the steps of the method of using the safety needle system of a preferred embodiment.
Figure 34B:
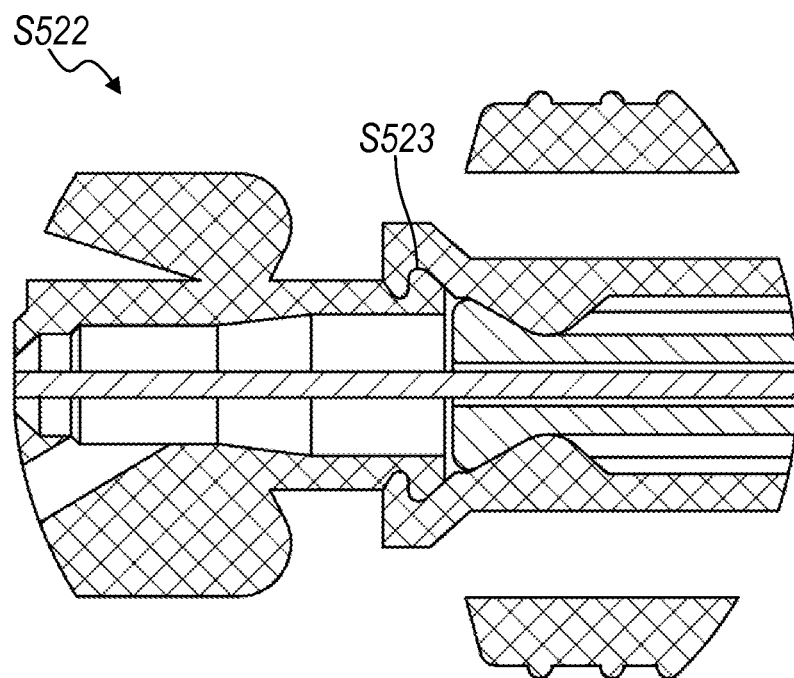

Inserting the needle into the patient (Step S510) preferably includes any suitable steps for particular applications, such as threading a catheter over the needle into a blood vessel and drawing blood through the needle. These steps are common and are familiar to one skilled in the art, although any suitable insertion step may be used. As shown in FIG. 34, the step of inserting the needle into the patient may further include inserting the needle through a portion of the medical device, such as a catheter hub.

Figure 35A:
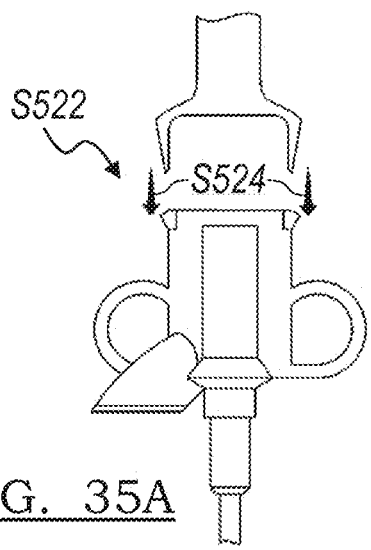
Figure 35B:
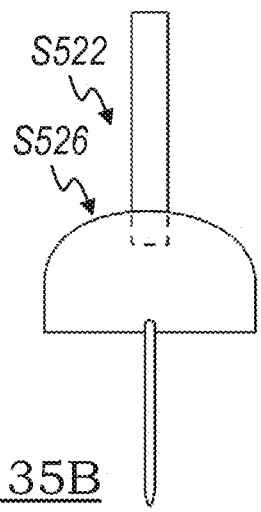

In one embodiment, as shown in FIGS. 34, 35A and 35B, coupling a distal portion of the sheath to the portion of the medical device includes mechanically coupling the sheath to the medical device (Step S522). In one variation, mechanically coupling the sheath to the medical device includes seating a portion of the medical device within the distal portion of the sheath, such as surrounding or gripping a portion of the medical device with flexible jaws (Step S523) or receiving a feature of the medical device in a receptacle of the sheath (Step S524). In another variation, mechanically coupling the sheath to the medical device (Step S522) includes seating the distal end of the sheath in a receptacle of the medical device (Step S526). In other variations, mechanically coupling the sheath to the medical device includes manipulating snaps, latches, tabs and slots, magnets, or any suitable fastener.

Figure 35C:
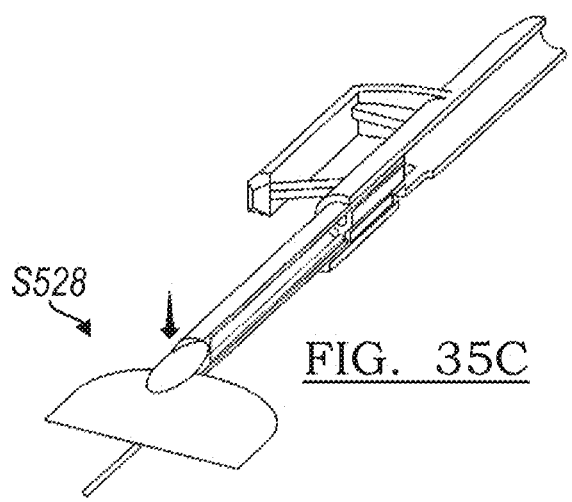

In another embodiment, as shown in FIG. 35C, coupling a distal portion of the sheath to the portion of the medical device includes manually coupling the sheath to the medical device, which may include manually pressing a holding tab (or other finger rest, extension, or other portion of the sheath) of the sheath over the medical device (Step S528). In other variations manually coupling the sheath to the medical device may include any suitable manual coupling step.

Figure 36:
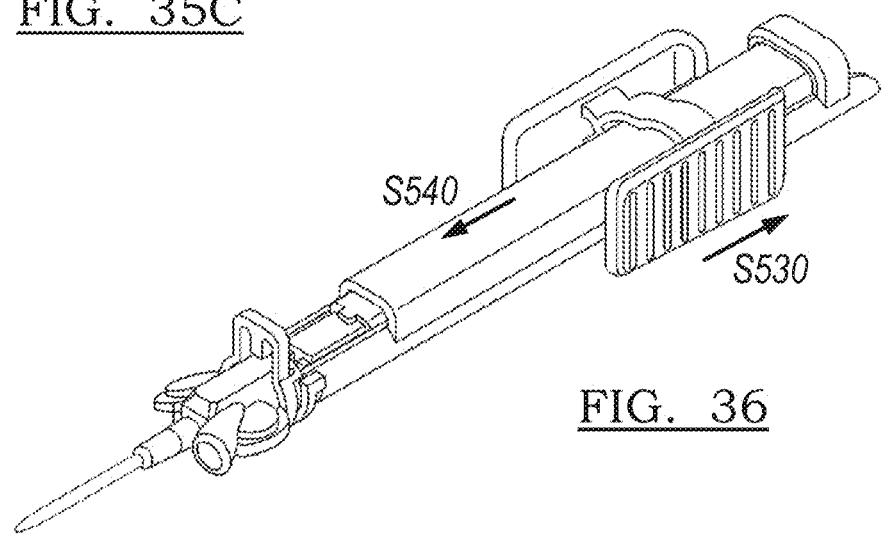
Figure 37:
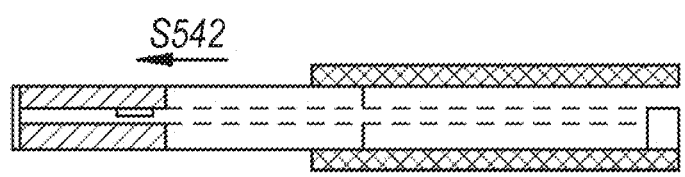

As shown in FIG. 36, pulling the housing away from the medical device (Step S530) initiates allowing the sheath to slide in a distal direction towards the extended position. Pulling the housing away from the medical device includes maintaining the coupling between the sheath and medical device, although in a preferred embodiment, the coupling between the sheath and the medical device may be weakened after the sheath is in the extended mode, thereby lowering the required amount of force to separate or decouple the sheath and the medical device. As also shown in FIG. 36, allowing the sheath to slide in a distal direction towards the extended position (Step S540) includes drawing the sheath into the extended position. In one embodiment, as shown in FIG. 37, allowing the sheath to slide in a distal direction includes drawing a septum over the needle (Step S542), which allows the sheath to contain fluid leakage from the needle. When the sheath is in the extended position, the septum preferably encloses the distal tip of the needle and the notch (if present). Steps S530 and S540 are preferably performed approximately simultaneously, but may alternatively be performed separately and sequentially.

Figure 38A:
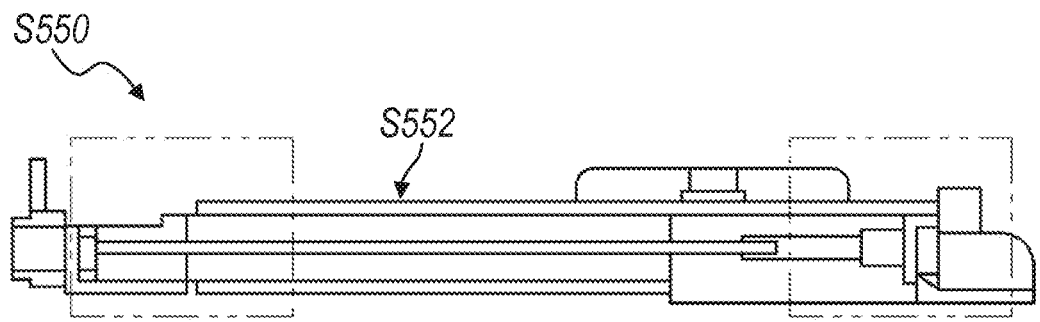
Figure 38B:
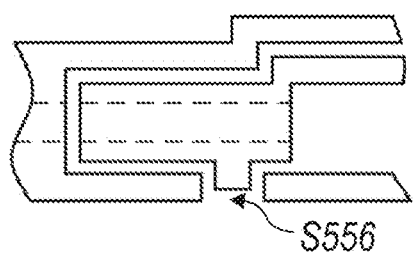
Figure 38C:
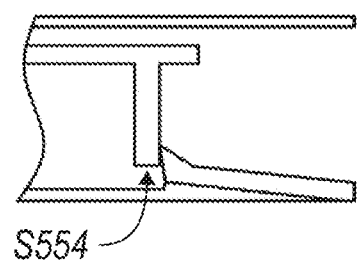
Figure 39A:
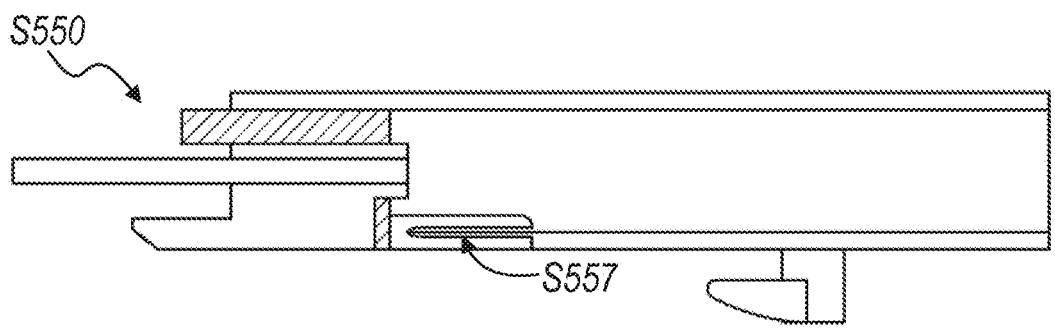
Figure 39B:
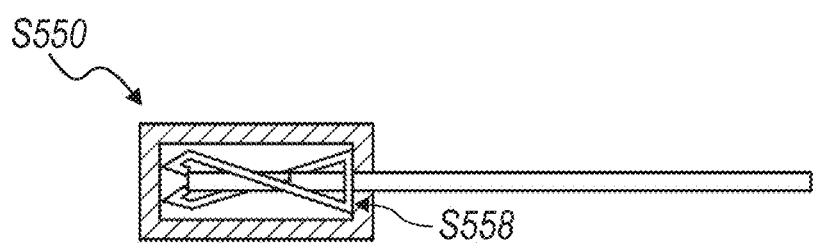
Figure 40A:
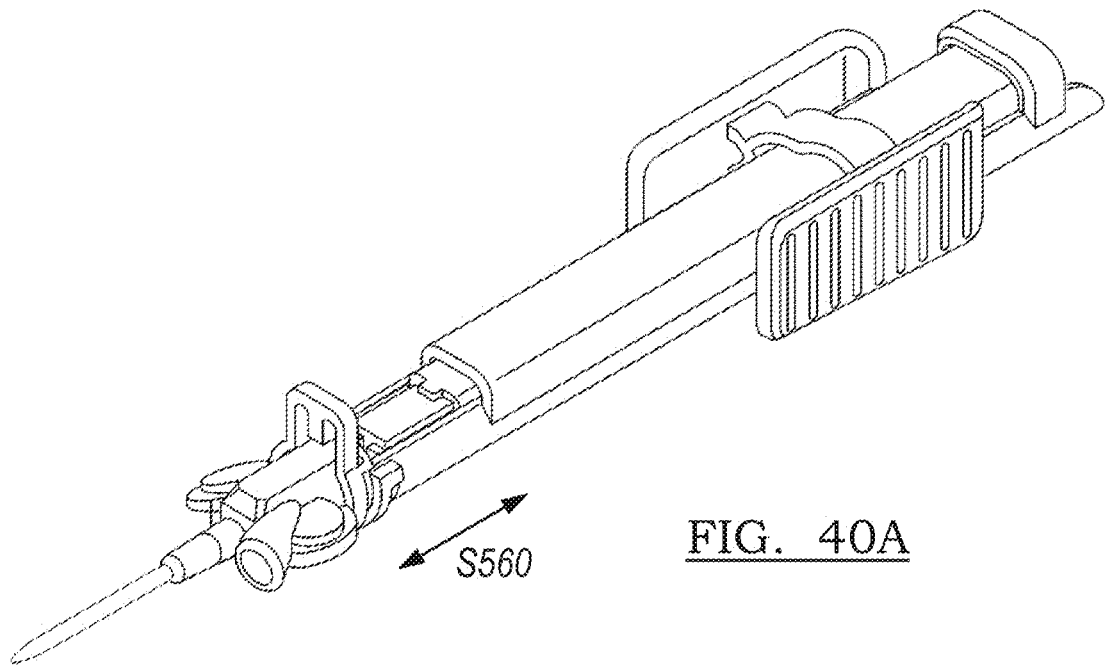
Figure 40B:
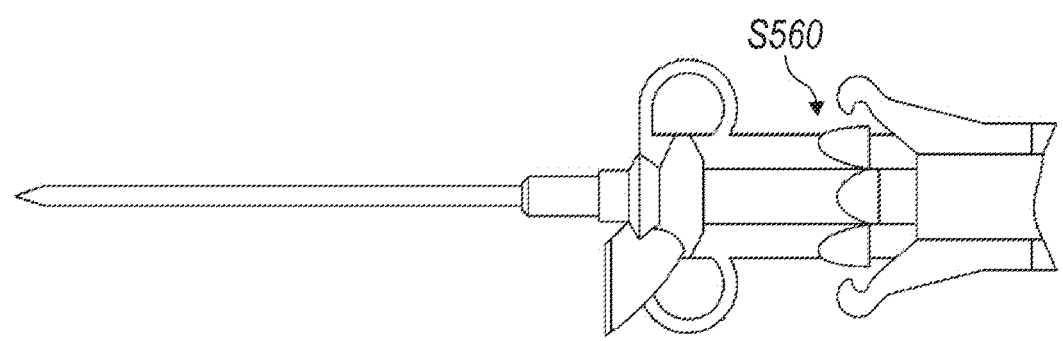

Locking the sheath in the extended position (Step S550) may be one of more of several variations. In one variation, such as with the safety needle system of the first embodiment as shown in FIGS. 38-38C, locking the sheath (Step S550) includes longitudinally wedging a slider between the extended sheath and the housing (Step S552). Wedging the slider (Step S552) preferably includes coupling a proximal end of the slider to the housing (Step S554) and coupling a distal end of the slider to the sheath (Step S5561, thereby preventing relative longitudinal movement between the sheath and the housing. In another variation, as shown in FIG. 39A, locking the sheath (Step S550) includes allowing a locking mechanism to abut a proximal portion of the sheath against a stop (Step S557). For example, a snap lock cantilever arm on the housing may abut the catch of the sheath against the setting of the housing, thereby trapping the catch in the alcove space adjacent to the setting. In a third variation, as shown in FIG. 39B, locking the sheath (Step S550) includes allowing the sheath and needle to engage with a catch (Step S558). The catch may be coupled to the sheath and engage with the needle (e.g., a spring clip within the septum or other portion of the sheath), and/or the catch may be coupled to the needle and engage with the sheath (e.g. a compressible ring around an external surface of the needle). However, locking the sheath in the extended position may include any suitable step.

Uncoupling the distal portion of the sheath from the medical device (Step S560) includes reversing the mechanical or coupling step performed when coupling the distal portion of the sheath to the medical device. Uncoupling may include unseating the medical device from within the sheath, unseating the sheath from the medical device, releasing a manual holding force coupling the medical device and sheath, or any suitable step. In some embodiments, the interaction of the sheath, slider, and housing triggers automatic decoupling of the sheath from the medical device. Following the uncoupling step, the needle is contained within the extended sheath and the safety needle system is fully disengaged from the medical device.

As a person skilled in the art will recognize from the previous detailed description and from the figures and claims, modifications and changes can be made to the preferred embodiments of the invention without departing from the scope of this invention defined in the following claims.

We claim:

1. A system comprising:
   a vascular delivery system adapted to be placed about a catheter insertion site on a patient, the vascular delivery system comprising:
   a catheter, a frame with a catheter hub providing a first anchoring point, a stabilization hub providing a second anchoring point, and at least one lateral member extending between the catheter hub and the stabilization hub;
   wherein the frame is configured to operate in a folded configuration and an unfolded configuration, the at least one lateral member being bendable such that the stabilization hub is movable relative to the catheter hub;
   wherein when the frame is in the unfolded configuration, the at least one lateral member extends distally directly from the catheter hub;
   wherein the first and second anchoring points are configured to be distributed around the catheter insertion site; and
   a safety needle system operable with the vascular delivery system, the safety needle system comprising:
   a housing;
   a needle having a distal end insertable through the vascular delivery system and a proximal end extending into the housing, the housing being configured to support the needle, the needle being insertable through both the catheter and the catheter hub; and
   a needle catch comprising a spring clip configured to engage a portion of the needle when the distal end of the needle is removed from the vascular delivery system.

2. The system of claim 1, further comprising an enclosure circumferentially surrounding the spring clip.

3. The system of claim 1, wherein the spring clip comprises a first arm and a second arm.

4. The system of claim 3, wherein the first arm extends further distally than the second arm.

5. The system of claim 3, wherein each of the first arm and the second arm comprises a curved portion.

6. The system of claim 1, wherein at least one of the stabilization hub and the catheter hub is configured to pass over the other of the stabilization hub and the catheter hub.

7. The system of claim 1, wherein the catheter hub is configured to couple to the stabilization hub.

8. The system of claim 1, wherein the at least one lateral member is configured to be reversibly bendable.

9. The system of claim 1, further comprising a septum configured to couple to the vascular delivery system, the septum having a first seal, a second seal, and a cavity between the first and second seals.

10. The system of claim 1, wherein when the frame is in the unfolded configuration, the first and second anchoring points are configured to be positioned on opposite sides of the catheter insertion site.

11. The system of claim 10, wherein when the frame is in the unfolded configuration, the first and second anchoring points are configured to be directly opposed from each other on the opposite sides of the catheter insertion site.

12. The system of claim 1, wherein when the frame is in the unfolded configuration, the frame is configured to form at least a partial perimeter around the catheter insertion site.

13. A system comprising:
a vascular delivery system adapted to be placed about a catheter insertion site on a patient, the vascular delivery system comprising:
a catheter, a frame with a catheter hub providing a first anchoring point, a stabilization hub providing a second anchoring point, and at least one lateral member extending between the catheter hub and the stabilization hub;
wherein the frame is configured to operate in a folded configuration and an unfolded configuration, the at least one lateral member being bendable such that the stabilization hub is movable relative to the catheter hub;
wherein when the frame is in the unfolded configuration, the at least one lateral member extends distally directly from the catheter hub;
wherein the first and second anchoring points are configured to be distributed around the catheter insertion site; and
a safety needle system operable with the vascular delivery system, the safety needle system comprising:
a housing;
a needle having a distal end insertable through the vascular delivery system and a proximal end extending into the housing, the housing being configured to support the needle, the needle being insertable through both the catheter and the catheter hub; and
a septum configured to couple to the vascular delivery system, the septum having a first seal, a second seal, and a cavity between the first and second seals.

14. The system of claim 13, wherein the septum is configured to be circumferentially enclosed by the vascular delivery system.

15. The system of claim 13, further comprising a compressible ring disposed on an external surface of the needle.

16. The system of claim 13, wherein the needle comprises a notch along a portion of a length of the needle.

17. The system of claim 16, wherein a length of the cavity of the septum is at least as long as a distance between the distal end of the needle and a proximal end of the notch along the portion of the length of the needle.

18. The system of claim 13, wherein the cavity of the septum is larger than a diameter of the needle.

19. The system of claim 13, wherein the septum is coupled to the vascular delivery system in a fluid-tight manner.

20. The system of claim 13, further comprising a spring clip configured to engage a portion of the needle when the distal end of the needle is removed from the vascular delivery system.

21. The system of claim 13, wherein at least one of the stabilization hub and the catheter hub is configured to pass over the other of the stabilization hub and the catheter hub.

22. The system of claim 13, wherein the catheter hub is configured to couple to the stabilization hub.

23. The system of claim 13, wherein when the frame is in the unfolded configuration, the first and second anchoring points are configured to be positioned on opposite sides of the catheter insertion site.

24. The system of claim 23, wherein when the frame is in the unfolded configuration, the first and second anchoring points are configured to be directly opposed from each other on the opposite sides of the catheter insertion site.

25. The system of claim 13, wherein when the frame is in the unfolded configuration, the frame is configured to form at least a partial perimeter around the catheter insertion site.

* * * * *